(12) United States Patent
Mulligan et al.

(10) Patent No.: US 10,233,447 B2
(45) Date of Patent: Mar. 19, 2019

(54) SELF-CLEAVING RIBOZYMES AND USES THEREOF

(71) Applicant: The Children s Medical Center Corporation, Boston, MA (US)

(72) Inventors: Richard Mulligan, Cambridge, MA (US); Laising Yen, Stoughton, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/397,210

(22) Filed: Jan. 3, 2017

(65) Prior Publication Data

US 2017/0253872 A1    Sep. 7, 2017

Related U.S. Application Data

(63) Continuation of application No. 13/471,255, filed on May 14, 2012, now abandoned, which is a continuation of application No. 12/715,104, filed on Mar. 1, 2010, now abandoned, which is a continuation of application No. 10/990,355, filed on Nov. 15, 2004, now abandoned.

(60) Provisional application No. 60/519,941, filed on Nov. 14, 2003.

(51) Int. Cl.
  *C12N 15/11* (2006.01)
  *C12N 15/113* (2010.01)
  *C12N 15/63* (2006.01)

(52) U.S. Cl.
  CPC ............ *C12N 15/113* (2013.01); *C12N 15/63* (2013.01); *C12N 2310/11* (2013.01); *C12N 2310/12* (2013.01)

(58) Field of Classification Search
  None
  See application file for complete search history.

(56) References Cited

U.S. PATENT DOCUMENTS

| 6,221,661 B1 | 4/2001 | Hampel et al. |
| 2002/0166132 A1 | 11/2002 | Scherman et al. |
| 2006/0121466 A1 | 6/2006 | Khvorova et al. |

FOREIGN PATENT DOCUMENTS

| WO | 2000/024912 | 5/2000 |
| WO | 2003/106625 | 12/2003 |

OTHER PUBLICATIONS

Aszalos et al., "Identification of antibiotic 1037 as toyocamycin," J. Antibiot., 19:285 (1966).
Beauvais et al., "In vitro model to assess effect of antimicrobial agents on Encephalitozoon cuniculi," Antimicrobial Agents and Chemotherapy, 38: 2440-2448 (1994).
Braasch et al., "Novel antisense and peptide nucleic acid strategies for controlling gene expression," Biochemistry, 41:4503-10 (2002).
Breaker et al., "In vitro selection of self-cleaving ribozymes and deoxyribozymes," Intracellular Ribozyme Applicaiotns: Principles and Protocols, Wymondham Horizon Scientific Press, GB, pp. 1-19 (1999).
Breaker, R R, "Engineered allosteric ribozymes as biosensor components," Curr. Opin. Biotechnol., 13:31-39 (2002).
Cech, T. R., "Nobel lecture. Self. splicing and enzymatic activity of an intervening sequence RNA from Tetrahymena," Biosci. Rep., 10:239-61 (1990).
Cech, T. R., "RNA finds a Simpler way," Nature, 428:263-4 (2004).
Chowrira et al., "In vitro and in vivo comparison of hammerhead, hairpin, and hepatitis delta virus self-processing ribozyme cassettes," J. Biol. Chem., 269:25856-64 (1994).
Communication in European Patent Application No. 04819142.3, dated Nov. 4, 2009 (3 pages).
Communication in European Patent Application No. 11187942.5, dated Apr. 5, 2013.
Communication issued in EP04819142.3 dated Feb. 8, 2011 (6 pages).
Communication issued in European Patent Application No. 04819142. 3, dated Jul. 5, 2010 (6 pages).
Conaty et al., "Selected classes of minimised hammerhead ribozyme have very high cleavage rates at low Mg2+ concentration," Nucleic Acids Res., 27:2400-7 (1999).
Contag et al., "Bioluminescent indicators in living mammals," Nat. Med., 4:245-7 (1998).
Drew et al., "RNA hairpin loops repress protein synthesis more strongly than hammerhead ribozymes," Eur. J. Biochem., 266:260-273
Examiner's First Report on Australian Patent Application No. 2004291911, dated Jun. 18, 2008.
Examiner's First Report on Australian Patent Application No. 2010201034, dated Jan. 16, 2012.
Extended European Search Report and Opinion in European Patent Application No. 11187942.5, dated Jun. 19, 2012.
Ferbeyre et al., "Schistosome satellite DNA encodes active hammerhead ribozymes," Mol. Cell. Biol., 18:3880-8 (1998).
Gossen et al., "Tight control of gene expression in mammalian cells by tetracycline responsive promoters," Proc. Natl. Acad. Sci. USA, 89:5547-51 (1992).
Hamada et al., "Comparison of In Vivo Activities of 5'-Connected and 3'-Connected cis-Acting Ribozymes: Selection of Intracellularly Active Ribozymes Using the Gene for Dihydrofolate Reductase (DHFR) as a Selective Marker in *Escherichia coli*," J. Biochem., 123:684-692 (1998).
Hammann et al., "Folding and activity of the hammerhead ribozyme," ChemBio Chem, 3: 690-700 (2002).
Hartig et al., Reporter ribozymes for real-time analysis of domain-specific interactions in biomolecules: HIV-1 reverse transcriptase and the primer-template complex, 2002, Angewandte Chemie International Edition, vol. 41, pp. 4263-4266.

(Continued)

*Primary Examiner* — Dana H Shin
(74) *Attorney, Agent, or Firm* — Fish & Richardson P.C.

(57) ABSTRACT

In certain embodiments, the disclosure relates to compositions and methods relating to a ribozyme-based gene regulation system that functions in mammalian cells. In certain specific embodiments, the disclosure relates to schistosome self-cleaving RNA mutant motifs.

34 Claims, 26 Drawing Sheets

Specification includes a Sequence Listing.

(56) References Cited

OTHER PUBLICATIONS

Hermann et al., "Aminoglycoside binding to the hammerhead ribozyme: a general model for the interaction of cationic antibiotics with RNA," J. Mol. Biol., 276:903-12 (1998).
Hertel et al., "Numbering system for the hammerhead," Nucleic Acids Res., 20:3252 (1992).
International Preliminary Report on Patentability for PCT/US2004/038199, dated May 15, 2006.
International Search Report issued in PCT/US2004/038199 dated Aug. 31, 2005 (7 pages).
Invitation Pursuant to Article 94(3) and Rule 71(1) EPC in European Patent Application No. 04819142.3, dated Jun. 18, 2013.
Jenne et al., "Rapid identification and characterization of hammerhead-ribozyme inhibitors using fluorescence-based technology," Nat. Biotechnol., 19:56-61 (2001).
Mandal et al., "Adenine riboswitches and gene activation by disruption of a transcription terminator," Nat. Struct. Mol. Biol., 11:29-35 (2004).
Morcos, P. A., "Achieving efficient delivery of morpholino oligos in cultured cells," Genesis, 30:94-102 (2001).
Murray et al., "Antibiotic interactions with the hammerhead ribozyme:tetracyclines as a new class of hammerhead inhibitor," Biochem. J., 317 (Pt 3):855-60 (1996).
Office Action in Canadian Patent Application No. 2,545,697, dated Apr. 19, 2012 (3 pages).
Office Action in Canadian Patent Application No. 2,545,697, dated Jan. 19, 2010 (7 pages).
Office Action in Canadian Patent Application No. 2,545,697, dated May 10, 2013 (3 pages).
Result of Consultation for European Patent Application No. 04819142.3, dated Jan. 14, 2013.
Rivera et al., "A humanized system for pharmacologic control of gene expression," Nat. Med., 2:1028-32 (1996).
Rogers et al., "Inhibition of the Self-cleavage Reaction of the Human Hepatitis Delta Virus Ribozyme by Antibiotics," J. Mol. Bio., 259:916-925 (1996).
Rojas et al., "Hammerhead-mediated processing of satellite pD0500 family transcripts from Dolichopoda cave crickets," Nucleic Acids Res., 28:4037-43 (2000).
Ruffner et al., "Sequence requirements of the hammerhead RNA self-cleavage reaction," Biochemistry, 29:10695-702 (1990).
Salehi-Ashtiani, K. et al., "In vitro evolution suggests multiple origins for the hammerhead ribozyme," Nature, 414(6859):82-84 (2001).
Shih et al., "Catalytic Strategies of the Hepatitis Delta Virus Ribozymes," Annu. Rev. Biochem., 71:887-917 (2002).
Silverman, S. K., "Rube Goldberg goes (ribo)nuclear? Molecular switches and sensors made from RNA," RNA, 9:377-83 (2003).
Stage et al., "Inhibition of the hammerhead ribozyme by neomycin," RNA, 1:95-101 (1995).
Suhr et al., "High level transactivation by a modified Bombyx ecdysone receptor in mammalian cells without exogenous retinoid X receptor," Proc. Natl. Acad. Sci. USA, 95:7999-8004 (1998).
Summons to Attend Oral Proceedings for European Patent Application No. 04819142.3, dated Sep. 14, 2012.
The Merck Index for "fluorouracil", CAS registry No. 51-21-8, The Merck Index, fourteenth edition, information retrieved by accessing http://themerckindex.cambridgesoft.com on Apr. 24, 2008.
The Merck Index for "toyocamycin", CAS registry No. 606-58-6, The Merck Index, fourteenth edition, information retrieved by accessing http://themerckindex.cambridgesoft.com on Apr. 28, 2008.
Thomson et al., "In vitro selection of hammerhead ribozymes containing a bulged nucleotide in stem II," Nucleic Acids Research, Oxford University Press, 24(22):4401-4406 (1996).
Tor et al., "Deciphering RNA recognition: aminoglycoside binding to the hammerhead ribozyme," Chem. Biol., 5:R277-83 (1998).
Vazquez-Tello et al., "Efficient trans-cleavage by the Schistosoma mansomi SMa1 hammerhead ribozyme in the extreme thermophile Thermus thermophilus," Nucleic Acids Research, 30: 1606-1612 (2002).
Von Ahsen et al., "Antibiotic inhibition of group I ribozyme function," Nature, 353:368-70 (1991).
Wang et al., "A regulatory system for use in gene transfer," Proc. Natl. Acad. Sci. USA, 91:8180-4 (1994).
Wilkinson et al., "Inhibition of ribosomal ribonucleic acid maturation in Novikoff hepatoma cells by 5-fluorouracil and 5-fluorouridine," The Journal of Biological Chemistry, 248: 63-68 (1973).
Wilson et al., "In vitro selection of functional nucleic acids," Annu. Rev. Biochem., 68:611-47 (1999).
Winkler et al., "Thiamine derivatives bind messenger RNAs directly to regulate bacterial gene expression," Nature, 419:952-6 (2002).
Winkler et al., C"ontrol of gene expression by a natural metabolite-responsive ribozyme," Nature, 428:281-6 (2004).
Written Opinion of the International Searching Authority for PCT/US2004/038199, completed Aug. 10, 2005, dated Aug. 31, 2005.
Yen et al., "Exogenous control of mammalian gene expression through modulation of RNA self-cleavage," Nature, 2844:1-6 (2004).
Yen, L., et al., "Exogenous control of mammalian gene expression through modulation of RNA self-cleavage," Nature, 431(7007):471-476 (2004).
Zhang et al., "The efficiency of a cis-cleaving ribozyme in an mRNA coding region is influenced by the translating ribosome in vivo," Nucleic Acids Research, 25(21),4301-4306 (1997).
Zillmann et al., "In vitro optimization of truncated stem-loop II variants of the hammerhead ribozyme for cleavage in low concentrations of magnesium under non-turnover conditions," RNA, 3:734-47 (1997).

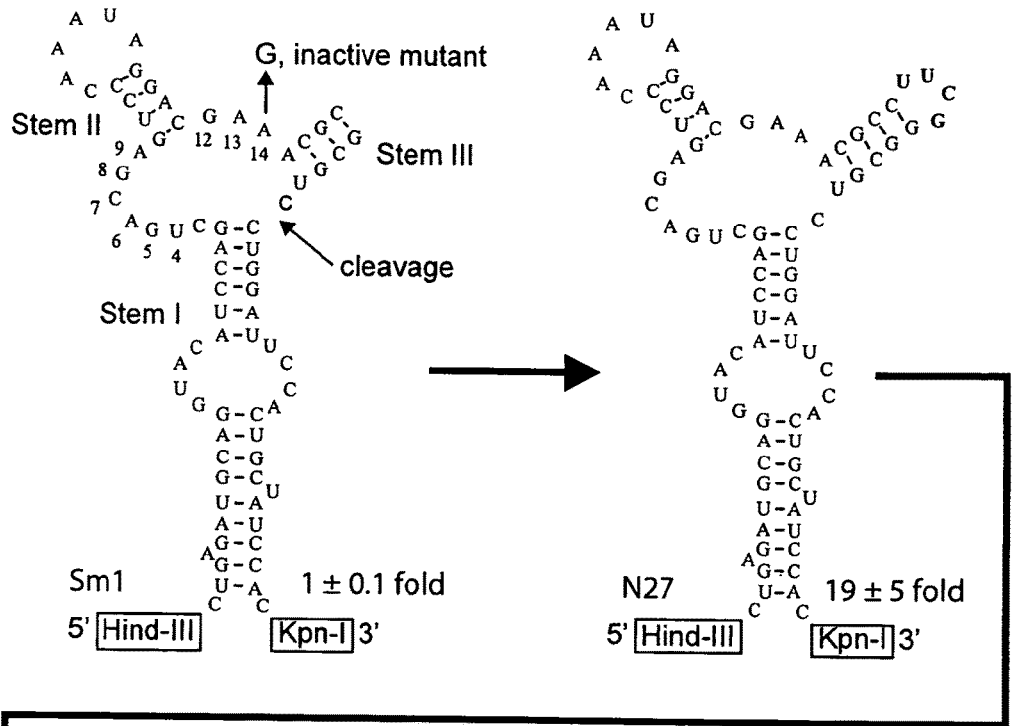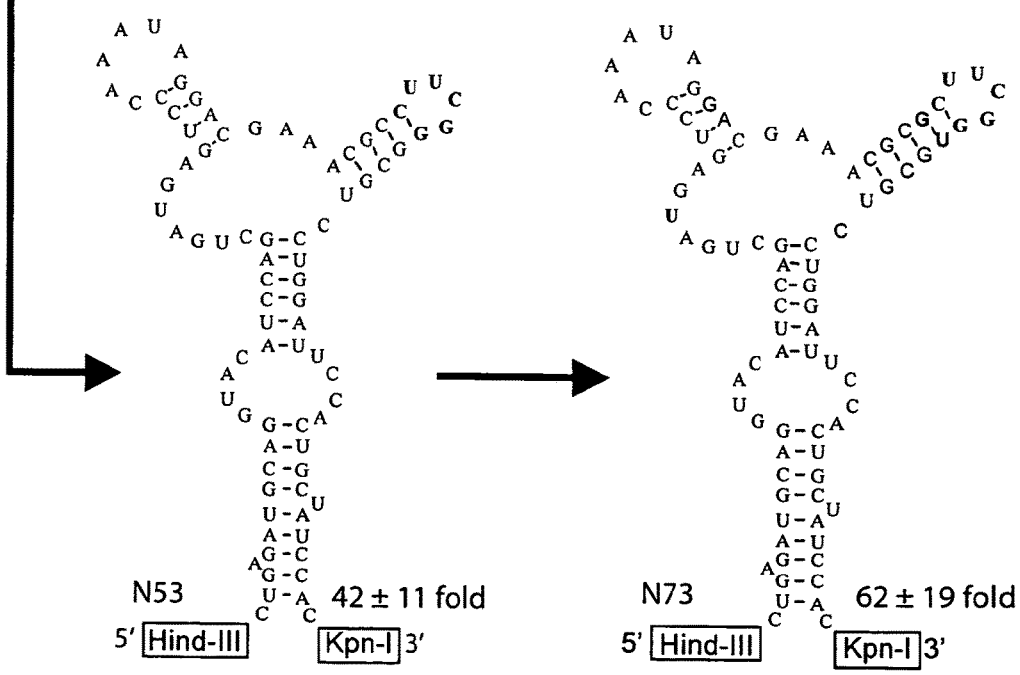
Fig. 1D

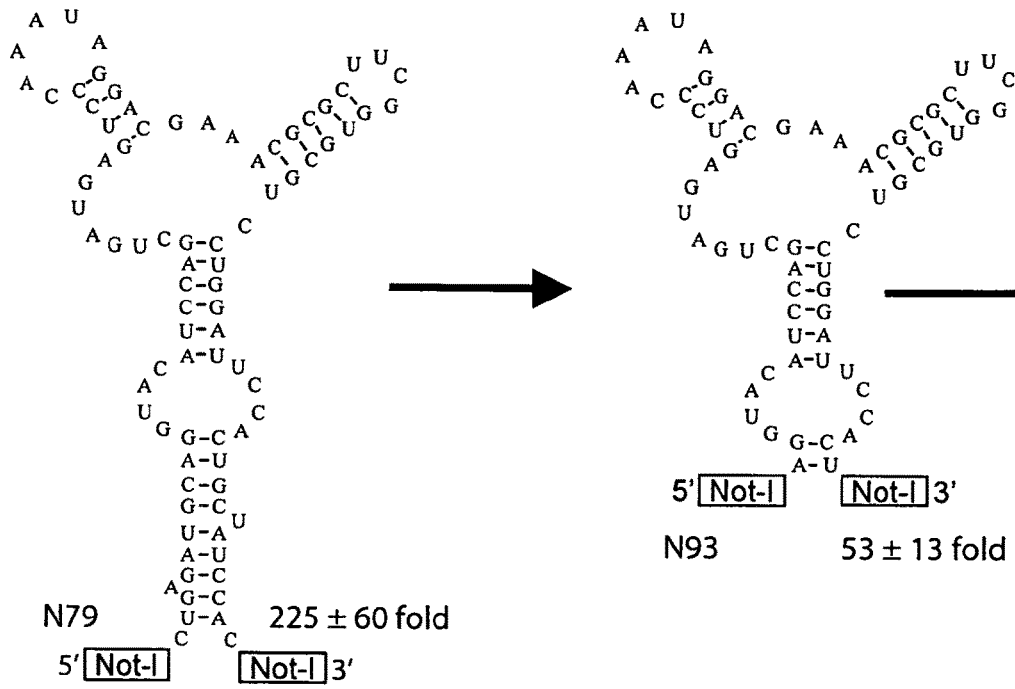
N79  225 ± 60 fold
N93  53 ± 13 fold
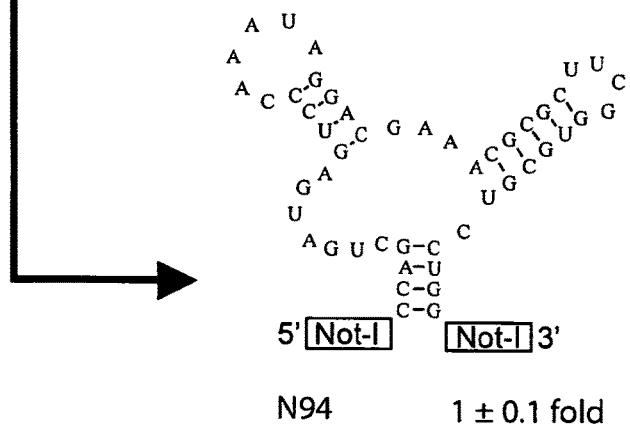
N94  1 ± 0.1 fold
Fig. 1F

| Type of cells | Kidney 293T | Cervical cancer Hela | Melanoma B16 | Ovary CHO | Fibroblast 3T3 |
|---|---|---|---|---|---|
| Functional Rz | 0.27 | 0.00 | 0.03 | 0.00 | 0.00 |
| Inactive Rz | 109.6 | 8.8 | 22.8 | 10.0 | 7.6 |
| Fold Decrease | 403 | N/A* | 671 | N/A* | N/A* |

* The reporter gene activity of functional ribozyme construct was undetectable

| Position | 5' UTR Cap | A | E | Intron B | C | D | 3' UTR F | G |
|---|---|---|---|---|---|---|---|---|
| single N79 | 102 ±17 | 62 ±19 | 225 ±60 | 2 ±1 | 3 ±1 | 3 ±1 | 4 ±2 | 3 ±1 |
| double N79 | 205 ±56 | 44 ±7 | 3183 ±717 | | | | 6 ±1 | |

| Induction | in fold | by percentage |
|---|---|---|
| Single N79 | 31 | 27% |
| | 23 | 35% |
| | 69 | 34% |
| Double N79 | 2012 | 38% |
| | 851 | 50% |
| | 110 | 5% |
| | 200 | 5% |
Fig. 3A
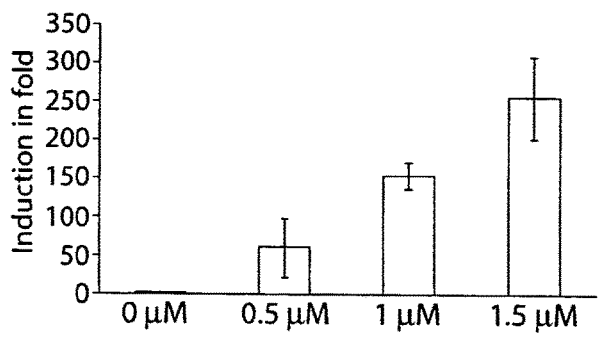
Fig. 3B
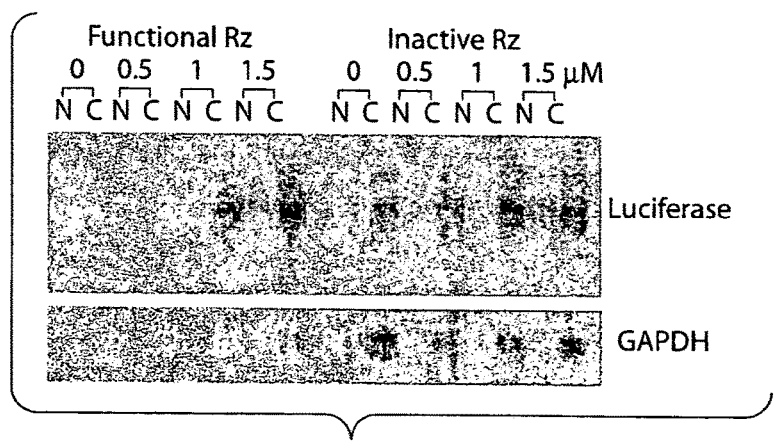
Fig. 3C Major modifications that improve the Schisto ribozyme function Schisto N79 sequence: CUGAGAUGCAGGUACAUCCAGCUGAUGAGUCCCAAAUAGGACGAAACGCgcuucgguccGUCCUGGAUUCCACUGCUAUCCAC

```
                          distal stem-I    loop-I  proximal stem-I       core    stem-II  loop-II  stem-II            core      stem-III  loop-III    stem-III   core  proximal stem-I  loop-I              distal stem-I
                      5' 1 2 3 4 5 6 7 8 9 10 11 12 13 14 15 16 17 18 19 20 21 22 23 24 25 26 27 28 29 30 31 32 33 34 35 36 37 38 39 40 41 42 43 44 45 46 47 48 49 50 51 52 53 54 55 56 57 58 59 60 61 62 63 64 65 66 67 68 69 70 71 72 73 74 75 76 77 78 79 80 81 82 83 3'
Difference in fold    
(Mutant vs wildtype)
  Name of Ribozyme
```

| Difference in fold | Name of Ribozyme | Sequence |
|---|---|---|
| 0 | N5 (Natural Schisto) | CUGAGAUGCAGGUACAUCCAGCUGAGAUCCCAGUCCCAAAUAGGACGAAACGC      c uucg g     GC GUC CUGGAUUCCACUGCUAUCCAC |
| 19 | N27 | |
| 52 | N53 | u          c uucg g |
| 71 | N73 | u          gcuucggu |
| 266 | N79 | u          gcuucggu |
| 410 | N99 | ca         gcuucggu      ug |
| 1400 | N117 | ca u       gcuucggu      ug |

Fig. 5A

Modifications at cleavage site GUC generally decrease the Schisto ribozyme function

| Difference in fold (Mutant vs wildtype) | Name of Ribozyme | 5' 1 2 3 4 5 6 7 8 9 10 11 12 13 14 15 16 17 18 19 20 21 22 23 24 25 26 27 28 29 30 31 32 33 34 35 36 37 38 39 40 41 42 43 44

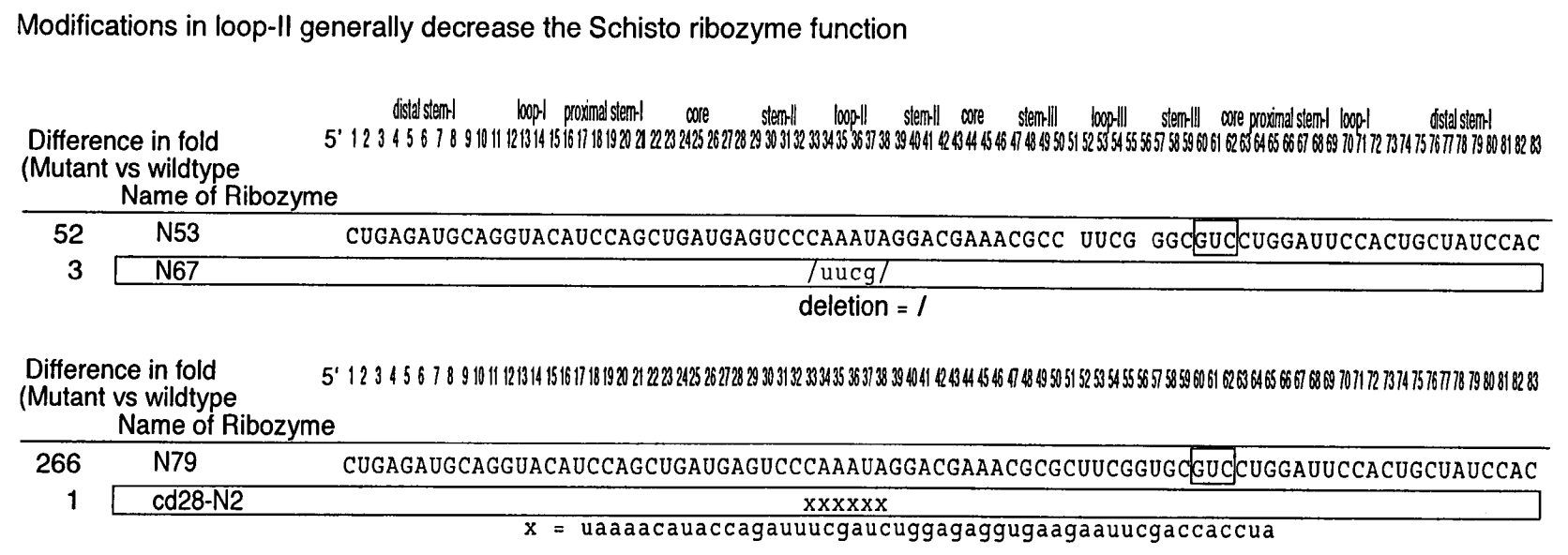

Modifications in loop-II generally decrease the Schisto ribozyme function

|  | Difference in fold (Mutant vs wild

Some modifications in loop-III decrease the Schisto ribozyme function

| Difference in fold (Mutant vs wildtype) | Name of Ribozyme | distal stem-I    loop-I Modifications in loop-I decrease the Schisto ribozyme function

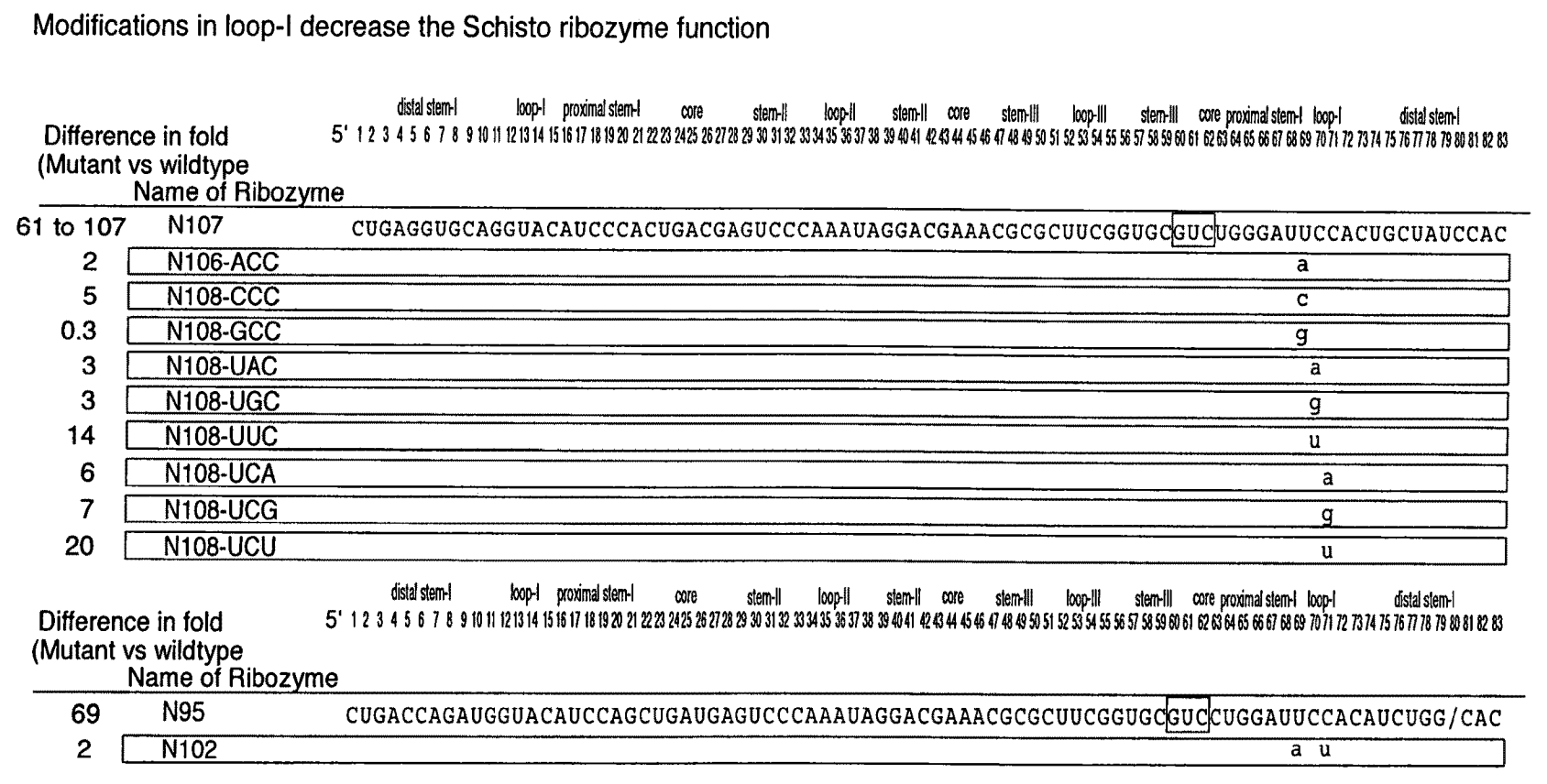

| Difference in fold (Mutant vs wildtype) | Name of Ribozyme |

Modifications in stem-I decrease the Schisto ribozyme function except for N99

| Difference in fold (Mutant vs wildtype) | Name of Ribozyme | 5' 1 2 3 4 5 6 7 8 9 10 11 12 13 14 15 16 17 18 19 20 21 22 23 24 25 26 27 28 29 30 31 32 33 34 35 36 37 38 39 40 41 42 43 44 45 46 47 48 49 50 51 52 53 54 55 56 57 58 59 60 61 62 63 64 65 66 67 68 69 70 71 72 73 74 75 76 77 78 79 80 81 82 83 |
|---|---|---|
|  |  | distal stem-I / loop-I / proximal stem-I / core / stem-I / loop-II / stem-II / loop-III / stem-III / core / proximal stem-I / loop-I / distal stem-I |
| 266 | N79 | CUGAGAUGCAGGUACAUCCAGCUGAUGAGUCCCAAAUAGGACGAAACGCGCCUUCGGUGC GUC CUGGAUCCCACUGCUAUCCAC |
| 57 | N93 | ////////// ///////// |
| 1 | N94 | ////

HDM-nLacZ sequence

```
AGCTTGGCCCATTGCATACGTTGTATCCATATCATAATATGTACATTTATATTGGCTCATGTCCAACATT
ACCGCCATGT TGACATTGATTATTGACTAGTTATTAATAGTAATCAATTACGGGGTCATTAGTTCATAGCCCATATATGG
AGTTCCGCGT TACATAACTTACGGTAAATGGCCCGCCTGGCTGACCGCCCAACGACCCCCGCCCATTGACGTCAATAATG
ACGTATGTTC CCATAGTAACGCCAATAGGGACTTTCCATTGACGTCAATGGGTGGAGTATTTACGGTAAACTGCCCACTT
GGCAGTACAT CAAGTGTATCATATGCCAAGTACGCCCCCTATTGACGTCAATGACGGTAAATGGCCCGCCTGGCATTATG
CCCAGTACAT GACCTTATGGGACTTTCCTACTTGGCAGTACATCTACGTATTAGTCATCGCTATTACCATGGTGATGCGG
TTTTGGCAGT ACATCAATGGGCGTGGATAGCGGTTTGACTCACGGGGATTTCCAAGTCTCCACCCCATTGACGTCAATGG
GAGTTTGTTT TGGCACCAAAATCAACGGGACTTTCCAAAATGTCGTAACAACTCCGCCCCATTGACGCAAATGGGCGGTA
GGCGTGTACG GTGGGAGGTCTATATAAGCAGAGCTCGTTTAGTGAACCGTCAGATCGCCTGGAGACGCCATCCACGCTGT
TTTGACCTCC ATAGAAGACACCGGGACCGATCCAGCCTCCCCTCGAAGCTGATCCTGAGAACTTCAGGGTGAGTCTATGG
GACCCTTGAT GTTTTCTTTCCCCTTCTTTTCTATGGTTAAGTTCATGTCATAGGAAGGGGAGAAGTAACAGGGTACACAT
ATTGACCAAA TCAGGGTAATTTTGCATTTGTAATTTTAAAAAATGCTTTCTTCTTTTAATATACTTTTTTGTTTATCTTA
TTTCTAATAC TTTCCCTAATCTCTTTCTTTCAGGGCAATAATGATACAATGTATCATGCCTCTTTGCACCATTCTAAAGA
ATAACAGTGA TAATTTCTGGGTTAAGGCAATAGCAATATTTCTGCATATAAATATTTCTGCATATAAATTGTAACTGATG
TAAGAGGTTT CATATTGCTAATAGCAGCTACAATCCAGCTACCATTCTGCTTTTATTTTATGGTTGGGATAAGGCTGGAT
TATTCTGAGT CCAAGCTAGGCCCTTTTGCTAATCATGTTCATACCTCTTATCTTCCTCCCACAGCTCCTGGGCAACGTGC
TGGTCTGTGT GCTGGCCCATCACTTTGGCAAAGAATTCCGCGGGCGGCCGCCATGGCGCCAAAAAAGAAGAGAAAGGTAA
AGATCCCCGG GAATTCACTGGCCGTCGTTTTACAACGTCGTGACTGGGAAAACCCTGGCGTTACCCAACTTAATCGCCTT
GCAGCACATC CCCCTTTCGCCAGCTGGCGTAATAGCGAAGAGGCCCGCACCGATCGCCCTTCCCAACAGTTGCGCAGCCT
GAATGGCGAA TGGCGCTTTGCCTGGTTTCCGGCACCAGAAGCGGTGCCGGAAAGCTGGCTGGAGTGCGATCTTCCTGAGG
CCGATACTGT CGTCGTCCCCTCAAACTGGCAGATGCACGGTTACGATGCGCCCATCTACACCAACGTGACCTATCCCATT
ACGGTCAATC CGCCGTTTGTTCCCACGGAGAATCCGACGGGTTGTTACTCGCTCACATTTAATGTTGATGAAAGCTGGCT
ACAGGAAGGC CAGACGCGAATTATTTTTGATGGCGTTAACTCGGCGTTTCATCTGTGGTGCAACGGGCGCTGGGTCGGTT
ACGGCCAGGA CAGTCGTTTGCCGTCTGAATTTGACCTGAGCGCATTTTTACGCGCCGGAGAAAACCGCCTCGCGGTGATG
GTGCTGCGCT GGAGTGACGGCAGTTATCTGGAAGATCAGGATATGTGGCGGATGAGCGGCATTTTCCGTGACGTCTCGTT
GCTGCATAAA CCGACTACACAAATCAGCGATTTCCATGTTGCCACTCGCTTTAATGATGATTTCAGCCGCGCTGTACTGG
AGGCTGAAGT TCAGATGTGCGGCGAGTTGCGTGACTACCTACGGGTAACAGTTTCTTTATGGCAGGGTGAAACGCAGGTC
GCCAGCGGCA CCGCGCCTTTCGGCGGTGAAATTATCGATGAGCGTGGTGGTTATGCCGATCGCGTCACACTACGTCTGAA
CGTCGAAAAC CCGAAACTGTGGAGCGCCGAAATCCCGAATCTCTATCGTGCGGTGGTTGAACTGCACACCGCCGACGGCA
CGCTGATTGA AGCAGAAGCCTGCGATGTCGGTTTCCGCGAGGTGCGGATTGAAAATGGTCTGCTGCTGCTGAACGGCAAG
CCGTTGCTGA TTCGAGGCGTTAACCGTCACGAGCATCATCCTCTGCATGGTCAGGTCATGGATGAGCAGACGATGGTGCA
GGATATCCTG CTGATGAAGCAGAACAACTTTAACGCCGTGCGCTGTTCGCATTATCCGAACCATCCGCTGTGGTACACGC
TGTGCGACCG CTACGGCCTGTATGTGGTGGATGAAGCCAATATTGAAACCCACGGCATGGTGCCAATGAATCGTCTGACC
GATGATCCGC GCTGGCTACCGGCGATGAGCGAACGCGTAACGCGAATGGTGCAGCGCGATCGTAATCACCCGAGTGTGAT
CATCTGGTCG CTGGGGAATGAATCAGGCCACGGCGCTAATCACGACGCGCTGTATCGCTGGATCAAATCTGTCGATCCTT
CCCGCCCGGT GCAGTATGAAGGCGGCGGAGCCGACACCACGGCCACCGATATTATTTGCCCGATGTACGCGCGCGTGGAT
GAAGACCAGC CCTTCCCGGCTGTGCCGAAATGGTCCATCAAAAAATGGCTTTCGCTACCTGGAGAGACGCGCCCGCTGAT
CCTTTGCGAA TACGCCCACGCGATGGGTAACAGTCTTGGCGGTTTCGCTAAATACTGGCAGGCGTTTCGTCAGTATCCCC
GTTTACAGGG CGGCTTCGTCTGGGACTGGTGGATCAGTCGCTGATTAAATATGATGAAAACGGCAACCCGTGGTCGGCT
TACGGCGGTG ATTTTGGCGATACGCCGAACGATCGCCAGTTCTGTATGAACGGTCTGGTCTTTGCCGACCGCACGCCGCA
TCCAGCGCTG ACGGAAGCAAAACACCAGCAGCAGTTTTTCCAGTTCCGTTTATCCGGGCAAACCATCGAAGTGACCAGCG
AATACCTGTT CCGTCATAGCGATAACGAGCTCCTGCACTGGATGGTGGCGCTGGATGGTAAGCCGCTGGCAAGCGGTGAA
GTGCCTCTGG ATGTCGCTCCACAAGGTAAACAGTTGATTGAACTGCCTGAACTACCGCAGCCGGAGAGCGCCGGGCAACT
CTGGCTCACA GTACGCGTAGTGCAACCGAACGCGACCGCATGGTCAGAAGCCGGGCACATCAGCGCCTGGCAGCAGTGGC
GTCTGGCGGA AAACCTCAGTGTGACGCTCCCCGCCGCGTCCCACGCCATCCCGCATCTGACCACCAGCGAAATGGATTTT
TGCATCGAGC TGGGTAATAAGCGTTGGCAATTTAACCGCCAGTCAGGCTTTCTTTCACAGATGTGGATTGGCGATAAAAA
ACAACTGCTG ACGCCGCTGCGCGATCAGTTCACCCGTGCACCGCTGGATAACGACATTGGCGTAAGTGAAGCGACCCGCA
```

Fig. 8A

```
TTGACCCTAA CGCCTGGGTCGAACGCTGGAAGGCGGCGGGCCATTACCAGGCCGAAGCAGCGTTGTTGCAGTGCACGGCA
GATACACTTG CTGATGCGGTGCTGATTACGACCGCTCACGCGTGGCAGCATCAGGGGAAAACCTTATTTATCAGCCGGAA
AACCTACCGG ATTGATGGTAGTGGTCAAATGGCGATTACCGTTGATGTTGAAGTGGCGAGCGATACACCGCATCCGGCGC
GGATTGGCCT GAACTGCCAGCTGGCGCAGGTAGCAGAGCGGGTAAACTGGCTCGGATTAGGGCCGCAAGAAAACTATCCC
GACCGCCTTA CTGCCGCCTGTTTTGACCGCTGGGATCTGCCATTGTCAGACATGTATACCCCGTACGTCTTCCCGAGCGA
AAACGGTCTG CGCTGCGGGACGCGCGAATTGAATTATGGCCCACACCAGTGGCGCGGCGACTTCCAGTTCAACATCAGCC
GCTACAGTCA ACAGCAACTGATGGAAACCAGCCATCGCCATCTGCTGCACGCGGAAGAAGGCACATGGCTGAATATCGAC
GGTTTCCATA TGGGGATTGGTGGCGACGACTCCTGGAGCCCGTCAGTATCGGCGGAATTCCAGCTGAGCGCCGGTCGCTA
CCATTACCAG TTGGTCTGGTGTCAAAAATAATAATAACCGGGCAGGGGGATCCAAGCTTATCGATACCGTCGACCTCGA
GGGCCCAGAT CTAATTCACCCCACCAGTGCAGGCTGCCTATCAGAAAGTGGTGGCTGGTGTGGCTAATGCCCTGGCCCAC
AAGTATCACT AAGCTCGCTTTCTTGCTGTCCAATTTCTATTAAAGGTTCCTTTGTTCCCTAAGTCCAACTACTAAACtgg
gggatattat gaagggccttccggagcatctggattctgcctaataaaaaacatttattttcattgcaatgatgtatttA
AATTATTTCT GAATATTTACTAAAAAGGGAATGTGGGAGGTCAGTGCATTTAAAACATAAAGAAATGAAGAGCTAGTTC
AAACCTTGGG AAAATACACTATATCTTAAACTCCATGAAAGAAGGTGAGGCTGCAAACAGCTAATGCACATTGGCAACAG
CCCCTGATGC CTATGCCTTATTCATCCCTCAGAAAAGGATTCAAGTAGAGGCTTGATTTGGAGGTTAAAGTTTTGCTATG
CTGTATTTTA CATTACTTATTGTTTTAGCTGTCCTCATGAATGTCTTTTCACTACCCATTTGCTTATCCTGCATCTCTCA
GCCTTGACTC CACTCAGTTCTCTTGCTTAGAGATACCACCTTTCCCCTGAAGTGTTCCTTCCATGTTTTACGGCGAGATG
GTTTCTCCTC GCCTGGCCACTCAGCCTTAGTTGTCTCTGTTGTCTTATAGAGGTCTACTTGAAGAAGGAAAAACAGGGGG
CATGGTTTGA CTGTCCTGTGAGCCCTTCTTCCCTGCCTCCCCACTCACAGTGACCCGGAATCCCTCGACATGGCAGTCT
AGATCATTCT TGAAGACGAAAGGGCCTCGTGATACGCCTATTTTATAGGTTAATGTCATGATAATAATGGTTTCTTAGA
CGTCAGGTGG CACTTTTCGGGGAAATGTGCGCGGAACCCCTATTTGTTTATTTTTCTAAATACATTCAAATATGTATCCG
CTCATGAGAC AATAACCCTGATAAATGCTTCAATAATATTGAAAAAGGAAGAGTATGAGTATTCAACATTTCCGTGTCGC
CCTTATTCCC TTTTTTGCGGCATTTTGCCTTCCTGTTTTTGCTCACCCAGAAACGCTGGTGAAAGTAAAAGATGCTGAAG
ATCAGTTGGG TGCACGAGTGGGTTACATCGAACTGGATCTCAACAGCGGTAAGATCCTTGAGAGTTTTCGCCCCGAAGAA
CGTTTTCCAA TGATGAGCACTTTTAAAGTTCTGCTATGTGGCGCGGTATTATCCCGTATTGACGCCGGGCAAGAGCAACT
CGGTCGCCGC ATACACTATTCTCAGAATGACTTGGTTGAGTACTCACCAGTCACAGAAAAGCATCTTACGGATGGCATGA
CAGTAAGAGA ATTATGCAGTGCTGCCATAACCATGAGTGATAACACTGCGGCCAACTTACTTCTGACAACGATCGGAGGA
CCGAAGGAGC TAACCGCTTTTTTGCACAACATGGGGGATCATGTAACTCGCCTTGATCGTTGGGAACCGGAGCTGAATGA
AGCCATACCA AACGACGAGCGTGACACCACGATGCCTGTAGCAATGGCAACAACGTTGCGCAAACTATTAACTGGCGAAC
TACTTACTCT AGCTTCCCGGCAACAATTAATAGACTGGATGGAGGCGGATAAAGTTGCAGGACCACTTCTGCGCTCGGCC
CTTCCGGCTG GCTGGTTTATTGCTGATAAATCTGGAGCCGGTGAGCGTGGGTCTCGCGGTATCATTGCAGCACTGGGGCC
AGATGGTAAG CCCTCCCGTATCGTAGTTATCTACACGACGGGGAGTCAGGCAACTATGGATGAACGAAATAGACAGATCG
CTGAGATAGG TGCCTCACTGATTAAGCATTGGTAACTGTCAGACCAAGTTTACTCATATATACTTTAGATTGATTTAAAA
CTTCATTTTT AATTTAAAAGGATCTAGGTGAAGATCCTTTTTGATAATCTCATGACCAAAATCCCTTAACGTGAGTTTTC
GTTCCACTGA GCGTCAGACCCCGTAGAAAAGATCAAAGGATCTTCTTGAGATCCTTTTTTTCTGCGCGTAATCTGCTGCT
TGCAAACAAA AAAACCACCGCTACCAGCGGTGGTTTGTTTGCCGGATCAAGAGCTACCAACTCTTTTTCCGAAGGTAACT
GGCTTCAGCA GAGCGCAGATACCAAATACTGTTCTTCTAGTGTAGCCGTAGTTAGGCCACCACTTCAAGAACTCTGTAGC
ACCGCCTACA TACCTCGCTCTGCTAATCCTGTTACCAGTGGCTGCTGCCAGTGGCGATAAGTCGTGTCTTACCGGGTTGG
ACTCAAGACG ATAGTTACCGGATAAGGCGCAGCGGTCGGGCTGAACGGGGGGTTCGTGCACACAGCCCAGCTTGGAGCGA
ACGACCTACA CCGAACTGAGATACCTACAGCGTGAGCTATGAGAAAGCGCCACGCTTCCCGAAGGGAGAAAGGCGGACAG
GTATCCGGTA AGCGGCAGGGTCGGAACAGGAGAGCGCACGAGGGAGCTTCCAGGGGGAAACGCCTGGTATCTTTATAGTC
CTGTCGGGTT TCGCCACCTCTGACTTGAGCGTCGATTTTTGTGATGCTCGTCAGGGGGCGGAGCCTATGGAAAAACGCC
AGCAACGGAT GCGCCGCGTGCGGCTGCTGGAGATGGCGGACGCGATGGATATGTTCTGCCAAGGGTTGGTTTGCGCATTC
ACAGTTCTCC GCAAGAATTGATTGGCTCCAATTCTTGGAGTGGTGAATCCGTTAGCGAGGTGCCGCCGGCTTCCATTCAG
GTCGAGGTGG CCCGGCTCCATGCACCGCGACGCAACGCGGGGAGGCAGACAAGGTATAGGGCGGCGCCTACAATCCATGC
CAACCCGTTC CATGTGCTCGCCGAGGCGGCATAAATCCCCGTGACGATCAGCGGTCCAATGATCGAAGTTAGGCTGGTAA
GAGCCGCGAG CGATCCTTGAAGCTGTCCCTGATGGTCGTCATCTACCTGCCTGGACAGCATGGCCTGCAACGCGGGCATC
CCGATGCCGC CGGAAGCGAGAAGAATCATAATGGGGAAGGCCATCCAGCCTCGCGTCGGGGAGCTTTTTGCAAAAGCCTA
GGCCTCCAAA AAAGCCTCCTCACTACTTCTGGAATAGCTCAGAGGCCGAGGCGGCCTCGGCCTCTGCATAAATAAAAAAA
ATTAGTCAGC
CATG
```

Fig. 8B

SEQUENCE LISTING

```
<160> NUMBER OF SEQ ID NOS: 53

<210> SEQ ID NO 1
<211> LENGTH: 76
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 1
auguguguuc ccucugcccc gcugaugagg ucggggagac cgaaaggguc aacucuacgg      60
ggcuauuaca ugcaau                                                     76

<210> SEQ ID NO 2
<211> LENGTH: 75
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 2
cugagaugca gguacaucca gcugacgagu cccaaauagg acgaaacgcg cguccuggau      60
uccacugcua uccac                                                      75

<210> SEQ ID NO 3
<211> LENGTH: 81
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 3
cugagaugca gguacaucca gcugacgagu cccaaauagg acgaaacgcc uucgggcguc      60
cuggauucca cugcuaucca c                                               81

<210> SEQ ID NO 4
<211> LENGTH: 81
<212> TYPE: RNA
```

```
<213> ORGANISM: Unknown
<220> FEATURE:
<223> OTHER INFORMATION: Description of Unknown:
      modified schistosome ribozyme partial sequence

<400> SEQUENCE: 4
cugagaugca gguacaucca gcugaugagu cccaaauagg acgaaacgcc uucgggcguc      60
cuggauucca cugcuaucca c                                               81

<210> SEQ ID NO 5
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 5
cugagaugca gguacaucca gcugaugagu cccaaauagg acgaaacgcg cuucggugcg      60
uccuggauuc cacugcuauc cac                                             83

<210> SEQ ID NO 6
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 6
cugagaugca gguacauccc acugaugagu cccaaauagg acgaaacgcg cuucggugcg      60
ucugggauuc cacugcuauc cac                                             83

<210> SEQ ID NO 7
<211> LENGTH: 65
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 7
agguacaucc agcugaugag ucccaaauag gacgaaacgc gcuucggugc guccuggauu      60
ccacu                                                                 65

<210> SEQ ID NO 8
<211> LENGTH: 49
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 8
ccagcugaug agucccaaau aggacgaaac gcgcuucggu gcguccugg                 49

<210> SEQ ID NO 9
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 9
```

```
cugaggugca gguacaucca gcugacgagu cccaaauagg acgaaacgcg cuucggugcg    60
uccuggauuc cacugcuauc cac                                           83

<210> SEQ ID NO 10
<211> LENGTH: 81
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 10
cugagaugca gguacaucca gcugaugagu cccaaauagg acgaaacgcc uucgggcgug    60
cuggauucca cugcuaucca c                                             81

<210> SEQ ID NO 11
<211> LENGTH: 81
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 11
cugagaugca gguacaucca gcugaugagu cccaaauagg acgaaacgcc uucgggcguu    60
cuggauucca cugcuaucca c                                             81

<210> SEQ ID NO 12
<211> LENGTH: 81
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 12
cugagaugca gguacaucca gcugaugagu cccaaauagg acgaaacgcc uucgggcgua    60
cuggauucca cugcuaucca c                                             81

<210> SEQ ID NO 13
<211> LENGTH: 80
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 13
cugagaugca gguacaucca gcugaugagu cccaaauagg acgaaacgcu ucgggccucc    60
uggauuccac ugcuauccac                                               80

<210> SEQ ID NO 14
<211> LENGTH: 81
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 14
cugagaugca gguacaucca gcugaugagu cccaaauagg acgaaacgcc uucgggccug    60
cuggauucca cugcuaucca c                                             81
```

<210> SEQ ID NO 15
<211> LENGTH: 81
<212> TYPE: RNA
<213> ORGANISM: Unknown
<220> FEATURE:
<223> OTHER INFORMATION: Description of Unknown:
    modified schistosome ribozyme partial sequence

<400> SEQUENCE: 15
cugagaugca gguacaucca gcugaugagu cccaaauagg acgaaacgcc uucgggccuu    60
cuggauucca cugcuaucca c                                              81

<210> SEQ ID NO 16
<211> LENGTH: 81
<212> TYPE: RNA
<213> ORGANISM: Unknown
<220> FEATURE:
<223> OTHER INFORMATION: Description of Unknown:
    modified schistosome ribozyme partial sequence

<400> SEQUENCE: 16
cugagaugca gguacaucca gcugaugagu cccaaauagg acgaaacgcc uucgggccua    60
cuggauucca cugcuaucca c                                              81

<210> SEQ ID NO 17
<211> LENGTH: 79
<212> TYPE: RNA
<213> ORGANISM: Unknown
<220> FEATURE:
<223> OTHER INFORMATION: Description of Unknown:
    modified schistosome ribozyme partial sequence

<400> SEQUENCE: 17
cugagaugca gguacaucca gcugaugagu ccuucgggac gaaacgccuu cgggcguccu    60
ggauuccacu gcuauccac                                                 79

<210> SEQ ID NO 18
<211> LENGTH: 126
<212> TYPE: RNA
<213> ORGANISM: Unknown
<220> FEATURE:
<223> OTHER INFORMATION: Description of Unknown:
    modified schistosome ribozyme partial sequence

<400> SEQUENCE: 18
cugagaugca gguacaucca gcugaugagu ccuaaaacau accagauuuc gaucuggaga    60
ggugaagaau ucgaccaccu aggacgaaac gcgcuucggu gcguccugga uuccacugcu   120
auccac                                                              126

<210> SEQ ID NO 19
<211> LENGTH: 82
<212> TYPE: RNA
<213> ORGANISM: Unknown
<220> FEATURE:
<223> OTHER INFORMATION: Description of Unknown:
    modified schistosome ribozyme partial sequence

<400> SEQUENCE: 19
cugagaugca gguacaucca gcugaugagu cccaaauagg acgaaacgcc cuucgggcgu    60
ccuggauucc acugcuaucc ac                                             82

```
<210> SEQ ID NO 20
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 20
cugagaugca gguacaucca gcugaugagu cccaaauagg acgaaacgcc uuucgggcgu    60
ccuggauucc acugcuaucc ac                                            82

<210> SEQ ID NO 21
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 21
cugagaugca gguacaucca gcugaugagu cccaaauagg acgaaacgcc auucgggcgu    60
ccuggauucc acugcuaucc ac                                            82

<210> SEQ ID NO 22
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 22
cugagaugca gguacaucca gcugaugagu cccaaauagg acgaaacgcc guucgggcgu    60
ccuggauucc acugcuaucc ac                                            82

<210> SEQ ID NO 23
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 23
cugaggugca gguacauccc acugacgagu cccaaauagg acgaaacgcg cuucggugcg    60
ucugggauuc cacugcuauc cac                                           83

<210> SEQ ID NO 24
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 24
cugaggugca gguacauccc acugacgagu cccaaauagg acgaaacgcg cuucggugcg    60
ucugggauac cacugcuauc cac                                           83

<210> SEQ ID NO 25
<211> LENGTH: 83
<212> TYPE: RNA
<213> ORGANISM: Unknown
```

```
<220> FEATURE:
<223> OTHER INFORMATION: Description of Unknown:
      modified schistosome ribozyme partial sequence

<400> SEQUENCE: 25
cugaggugca gguacauccc acugacgagu cccaaauagg acgaaacgcg cuucggugcg    60
ucugggaucc cacugcuauc cac                                            83

<210> SEQ ID NO 26
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 26
cugaggugca gguacauccc acugacgagu cccaaauagg acgaaacgcg cuucggugcg    60
ucugggaugc cacugcuauc cac                                            83

<210> SEQ ID NO 27
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 27
cugaggugca gguacauccc acugacgagu cccaaauagg acgaaacgcg cuucggugcg    60
ucugggauua cacugcuauc cac                                            83

<210> SEQ ID NO 28
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 28
cugaggugca gguacauccc acugacgagu cccaaauagg acgaaacgcg cuucggugcg    60
ucugggauug cacugcuauc cac                                            83

<210> SEQ ID NO 29
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 29
cugaggugca gguacauccc acugacgagu cccaaauagg acgaaacgcg cuucggugcg    60
ucugggauuu cacugcuauc cac                                            83

<210> SEQ ID NO 30
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence
```

```
<400> SEQUENCE: 30
cugaggugca gguacauccc acugacgagu cccaaauagg acgaaacgcg cuucggugcg    60
ucugggauuc aacugcuauc cac                                            83

<210> SEQ ID NO 31
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 31
cugaggugca gguacauccc acugacgagu cccaaauagg acgaaacgcg cuucggugcg    60
ucugggauuc gacugcuauc cac                                            83

<210> SEQ ID NO 32
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 32
cugaggugca gguacauccc acugacgagu cccaaauagg acgaaacgcg cuucggugcg    60
ucugggauuc uacugcuauc cac                                            83

<210> SEQ ID NO 33
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 33
cugaccagau gguacaucca gcugaugagu cccaaauagg acgaaacgcg cuucggugcg    60
uccuggauuc cacaucuggc ac                                             82

<210> SEQ ID NO 34
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 34
cugaccagau gguacaucca gcugaugagu cccaaauagg acgaaacgcg cuucggugcg    60
uccuggauac uacaucuggc ac                                             82

<210> SEQ ID NO 35
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 35
cugagaugca gguacaucca ucugaugagu cccaaauagg acgaaacgcg cuucggugcg    60
```

```
ucauggauuc cacugcuauc cac                                           83

<210> SEQ ID NO 36
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 36
cugagaugca gguacauccc ucugaugagu cccaaauagg acgaaacgcg cuucggugcg    60
ucagggauuc cacugcuauc cac                                           83

<210> SEQ ID NO 37
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 37
cugagaugca gguacauccu acugaugagu cccaaauagg acgaaacgcg cuucggugcg    60
ucuaggauuc cacugcuauc cac                                           83

<210> SEQ ID NO 38
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 38
cugagaugca gguacauccg ucugaugagu cccaaauagg acgaaacgcg cuucggugcg    60
ucacggauuc cacugcuauc cac                                           83

<210> SEQ ID NO 39
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 39
cugaccaggu gguacaucca gcugaugagu cccaaauagg acgaaacgcg cuucggugcg    60
uccuggauuc cacaucuggc ac                                            82

<210> SEQ ID NO 40
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 40
cugaccaggu gguacauccc ucugaugagu cccaaauagg acgaaacgcg cuucggugcg    60
ucagggauuc cacaucuggc ac                                            82

<210> SEQ ID NO 41
```

```
<211> LENGTH: 82
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 41
cugaccaggu gguacauccc acugaugagu cccaaauagg acgaaacgcg cuucggugcg     60
ucugggauuc cacaucuggc ac                                              82

<210> SEQ ID NO 42
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 42
cugaggugca gguacaucca gcugaugagu cccaaauagg acgaaacgcg cuucggugcg     60
uccuggauuc cacugcuauc cac                                             83

<210> SEQ ID NO 43
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 43
cugaggugca gguacauccc acugaugagu cccaaauagg acgaaacgcg cuucggugcg     60
ucugggauuc cacugcuauc cac                                             83

<210> SEQ ID NO 44
<211> LENGTH: 83
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 44
cugaggugca gguacaucca gcuggugagu cccaaauagg acgaaacgcg cuucggugcg     60
uccuggauuc cacugcuauc cac                                             83

<210> SEQ ID NO 45
<211> LENGTH: 114
<212> TYPE: RNA
<213> ORGANISM: Unknown
<220> FEATURE:
<223> OTHER INFORMATION: Description of Unknown:
      modified schistosome ribozyme partial sequence

<400> SEQUENCE: 45
gccuaaaaca uaccagaugg uacauccagc ugaugagucc caaauaggac gaaacgcgcu     60
ucggugcguc cuggauucca caucuggaga ggugaagaau ucgaccaccu aggc          114

<210> SEQ ID NO 46
<211> LENGTH: 78
<212> TYPE: RNA
<213> ORGANISM: Unknown
<220> FEATURE:
```

<223> OTHER INFORMATION: Description of Unknown:
       modified schistosome ribozyme partial sequence

<400> SEQUENCE: 46
cugagaugcu uuacgcgucu gaugagaguccc aaauaggacg aaacgcgcuu cggugcguca    60
cgcguuguug cuauccac                                                   78

<210> SEQ ID NO 47
<211> LENGTH: 73
<212> TYPE: RNA
<213> ORGANISM: Unknown
<220> FEATURE:
<223> OTHER INFORMATION: Description of Unknown:
       modified schistosome ribozyme partial sequence
<220> FEATURE:
<221> NAME/KEY: modified_base
<222> LOCATION: (25)..(25)
<223> OTHER INFORMATION: a, c, u or g
<220> FEATURE:
<221> NAME/KEY: modified_base
<222> LOCATION: (49)..(49)
<223> OTHER INFORMATION: a, c, u or g

<400> SEQUENCE: 47
cugagaugca gguacaucag cugangaguc ccaaauagga cgaaacgcng gguccugauu    60
ccacugcauc cac                                                       73

<210> SEQ ID NO 48
<211> LENGTH: 76
<212> TYPE: RNA
<213> ORGANISM: Unknown
<220> FEATURE:
<223> OTHER INFORMATION: Description of Unknown:
       modified schistosome ribozyme partial sequence
<220> FEATURE:
<221> NAME/KEY: modified_base
<222> LOCATION: (25)..(25)
<223> OTHER INFORMATION: a, c, u or g

<400> SEQUENCE: 48
cugagaugca gguacaucag cugangaguc ccaaauagga cgaaacgcuu cgggguccug    60
auuccacugc auccac                                                    76

<210> SEQ ID NO 49
<211> LENGTH: 7684
<212> TYPE: DNA
<213> ORGANISM: Unknown
<220> FEATURE:
<223> OTHER INFORMATION: Description of Unknown:
       vector HDM-nLacZ nucleotide sequence

<400> SEQUENCE: 49
agcttggccc attgcatacg ttgtatccat atcataatat gtacatttat attggctcat     60
gtccaacatt accgccatgt tgacattgat tattgactag ttattaatag taatcaatta    120
cggggtcatt agttcatagc ccatatatgg agttccgcgt tacataactt acggtaaatg    180
gcccgcctgg ctgaccgccc aacgaccccc gcccattgac gtcaataatg acgtatgttc    240
ccatagtaac gccaataggg actttccatt gacgtcaatg ggtggagtat ttacggtaaa    300
ctgcccactt ggcagtacat caagtgtatc atatgccaag tacgccccct attgacgtca    360
atgacggtaa atggcccgcc tggcattatg cccagtacat gaccttatgg gactttccta    420
cttggcagta catctacgta ttagtcatcg ctattaccat ggtgatgcgg ttttggcagt    480
acatcaatgg gcgtggatag cggtttgact cacggggatt tccaagtctc cacccccattg   540

```
acgtcaatgg gagtttgttt tggcaccaaa atcaacggga ctttccaaaa tgtcgtaaca        600
actccgcccc attgacgcaa atgggcggta ggcgtgtacg gtgggaggtc tatataagca        660
gagctcgttt agtgaaccgt cagatcgcct ggagacgcca tccacgctgt tttgacctcc        720
atagaagaca ccgggaccga tccagcctcc cctcgaagct gatcctgaga acttcagggt        780
gagtctatgg gaccccttgat gtttctttc cccttctttt ctatggttaa gttcatgtca        840
taggaagggg agaagtaaca gggtacacat attgaccaaa tcagggtaat tttgcatttg        900
taattttaaa aaatgctttc ttcttttaat atactttttt gtttatctta tttctaatac        960
tttccctaat ctctttcttt cagggcaata atgatacaat gtatcatgcc tctttgcacc       1020
attctaaaga ataacagtga taatttctgg gttaaggcaa tagcaatatt tctgcatata       1080
aatatttctg catataaatt gtaactgatg taagaggttt catattgcta atagcagcta       1140
caatccagct accattctgc ttttatttta tggttgggat aaggctggat tattctgagt       1200
ccaagctagg ccccttttgct aatcatgttc atacctctta tcttcctccc acagctcctg       1260
ggcaacgtgc tggtctgtgt gctggcccat cactttggca agaattccg cgggcggccg        1320
ccatggcgcc aaaaaagaag agaaaggtaa agatccccgg gaattcactg gccgtcgttt       1380
tacaacgtcg tgactgggaa aaccctggcg ttacccaact taatcgcctt gcagcacatc       1440
cccctttcgc cagctggcgt aatagcgaag aggcccgcac cgatcgccct tcccaacagt       1500
tgcgcagcct gaatggcgaa tggcgctttg cctggtttcc ggcaccagaa gcggtgccgg       1560
aaagctggct ggagtgcgat cttcctgagg ccgatactgt cgtcgtcccc tcaaactggc       1620
agatgcacgg ttacgatgcg cccatctaca ccaacgtgac ctatcccatt acggtcaatc       1680
cgccgtttgt tcccacggag aatccgacgg gttgttactc gctcacattt aatgttgatg       1740
aaagctggct acaggaaggc cagacgcgaa ttattttga tggcgttaac tcggcgtttc       1800
atctgtggtg caacgggcgc tgggtcggtt acggccagga cagtcgtttg ccgtctgaat       1860
ttgacctgag cgcattttta cgcgccggag aaaaccgcct cgcggtgatg gtgctgcgct       1920
ggagtgacgg cagttatctg gaagatcagg atatgtggcg gatgagcggc attttccgtg       1980
acgtctcgtt gctgcataaa ccgactacac aaatcagcga tttccatgtt gccactcgct       2040
ttaatgatga tttcagccgc gctgtactgg aggctgaagt tcagatgtgc ggcgagttgc       2100
gtgactacct acgggtaaca gtttctttat ggcagggtga acgcaggtc gccagcggca        2160
ccgcgccttt cggcggtgaa attatcgatg agcgtggtgg ttatgccgat cgcgtcacac       2220
tacgtctgaa cgtcgaaaac ccgaaactgt ggagcgccga atcccgaat ctctatcgtg        2280
cggtggttga actgcacacc gccgacggca cgctgattga agcagaagcc tgcgatgtcg       2340
gtttccgcga ggtgcggatt gaaaatggtc tgctgctgct gaacggcaag ccgttgctga       2400
ttcgaggcgt taaccgtcac gagcatcatc ctctgcatgg tcaggtcatg gatgagcaga       2460
cgatggtgca ggatatcctg ctgatgaagc agaacaactt aacgccgtg cgctgttcgc        2520
attatccgaa ccatccgctg tggtacacgc tgtgcgaccg ctacggcctg tatgtggtgg       2580
atgaagccaa tattgaaacc cacggcatgg tgccaatgaa tcgtctgacc gatgatccgc       2640
gctggctacc ggcgatgagc gaacgcgtaa cgcgaatggt gcagcgcgat cgtaatcacc       2700
cgagtgtgat catctggtcg ctggggaatg aatcaggcca cggcgctaat cacgacgcgc       2760
tgtatcgctg gatcaaatct gtcgatcctt ccgcccgt gcagtatgaa ggcggcggag          2820
ccgacaccac ggccaccgat attatttgcc cgatgtacgc gcgcgtggat gaagaccagc       2880
```

-continued

```
ccttcccggc tgtgccgaaa tggtccatca aaaaatggct ttcgctacct ggagagacgc    2940
gcccgctgat cctttgcgaa tacgcccacg cgatgggtaa cagtcttggc ggtttcgcta    3000
aatactggca ggcgtttcgt cagtatcccc gtttacaggg cggcttcgtc tgggactggg    3060
tggatcagtc gctgattaaa tatgatgaaa acggcaaccc gtggtcggct tacggcggtg    3120
attttggcga tacgccgaac gatcgccagt tctgtatgaa cggtctggtc tttgccgacc    3180
gcacgccgca tccagcgctg acggaagcaa aacaccagca gcagttttc cagttccgtt     3240
tatccgggca aaccatcgaa gtgaccagcg aatacctgtt ccgtcatagc gataacgagc    3300
tcctgcactg gatggtggcg ctggatggta agccgctggc aagcggtgaa gtgcctctgg    3360
atgtcgctcc acaaggtaaa cagttgattg aactgcctga actaccgcag ccggagagcg    3420
ccgggcaact ctggctcaca gtacgcgtag tgcaaccgaa cgcgaccgca tggtcagaag    3480
ccgggcacat cagcgcctgg cagcagtggc gtctggcgga aaacctcagt gtgacgctcc    3540
ccgccgcgtc ccacgccatc ccgcatctga ccaccagcga aatggatttt tgcatcgagc    3600
tgggtaataa gcgttggcaa tttaaccgcc agtcaggctt tctttcacag atgtggattg    3660
gcgataaaaa acaactgctg acgccgctgc gcgatcagtt cacccgtgca ccgctggata    3720
acgacattgg cgtaagtgaa gcgacccgca ttgaccctaa cgcctgggtc gaacgctgga    3780
aggcggcggg ccattaccag gccgaagcag cgttgttgca gtgcacggca gatacacttg    3840
ctgatgcggt gctgattacg accgctcacg cgtggcagca tcaggggaaa accttattta    3900
tcagccggaa aacctaccgg attgatggta gtggtcaaat ggcgattacc gttgatgttg    3960
aagtggcgag cgatacaccg catccggcgc ggattggcct gaactgccag ctggcgcagg    4020
tagcagagcg ggtaaactgg ctcggattag ggccgcaaga aaactatccc gaccgcctta    4080
ctgccgcctg ttttgaccgc tgggatctgc cattgtcaga catgtatacc ccgtacgtct    4140
tcccgagcga aaacggtctg cgctgcggga cgcgcgaatt gaattatggc ccacaccagt    4200
ggcgcggcga cttccagttc aacatcagcc gctacagtca acagcaactg atggaaacca    4260
gccatcgcca tctgctgcac gcggaagaag gcacatggct gaatatcgac ggtttccata    4320
tggggattgg tggcgacgac tcctggagcc cgtcagtatc ggcggaattc cagctgagcg    4380
ccggtcgcta ccattaccag ttggtctggt gtcaaaaata ataataaccg ggcaggggg     4440
atccaagctt atcgataccg tcgacctcga gggcccagat ctaattcacc ccaccagtgc    4500
aggctgccta tcagaaagtg gtggctggtg tggctaatgc cctggcccac aagtatcact    4560
aagctcgctt tcttgctgtc caatttctat taaaggttcc tttgttccct aagtccaact    4620
actaaactgg gggatattat gaagggcctt ccggagcatc tggattctgc ctaataaaaa    4680
acatttattt tcattgcaat gatgtattta aattatttct gaatatttta ctaaaaaggg    4740
aatgtgggag gtcagtgcat ttaaaacata aagaaatgaa gagctagttc aaaccttggg    4800
aaaatacact atatcttaaa ctccatgaaa gaaggtgagg ctgcaaacag ctaatgcaca    4860
ttggcaacag cccctgatgc ctatgcctta ttcatccctc agaaaaggat tcaagtagag    4920
gcttgatttg gaggttaaag ttttgctatg ctgtatttta cattacttat tgttttagct    4980
gtcctcatga atgtcttttc actacccatt tgcttatcct gcatctctca gccttgactc    5040
cactcagttc tcttgcttag atataccacc tttcccctga agtgttcctt ccatgtttta    5100
cggcgagatg gtttctcctc gcctggccac tcagccttag ttgtctctgt tgtcttatag    5160
aggtctactt gaagaaggaa aaacaggggg catggtttga ctgtcctgtg agcccttctt    5220
ccctgcctcc cccactcaca gtgacccgga atccctcgac atggcagtct agatcattct    5280
```

```
tgaagacgaa agggcctcgt gatacgccta ttttatagg ttaatgtcat gataataatg   5340
gtttcttaga cgtcaggtgg cacttttcgg ggaaatgtgc gcggaacccc tatttgttta   5400
tttttctaaa tacattcaaa tatgtatccg ctcatgagac aataaccctg ataaatgctt   5460
caataatatt gaaaaggaa gagtatgagt attcaacatt tccgtgtcgc ccttattccc   5520
ttttttgcgg cattttgcct tcctgttttt gctcacccag aaacgctggt gaaagtaaaa   5580
gatgctgaag atcagttggg tgcacgagtg ggttacatcg aactggatct caacagcggt   5640
aagatccttg agagttttcg ccccgaagaa cgttttccaa tgatgagcac ttttaaagtt   5700
ctgctatgtg gcgcggtatt atcccgtatt gacgccgggc aagagcaact cggtcgccgc   5760
atacactatt ctcagaatga cttggttgag tactcaccag tcacagaaaa gcatcttacg   5820
gatggcatga cagtaagaga attatgcagt gctgccataa ccatgagtga taacactgcg   5880
gccaacttac ttctgacaac gatcggagga ccgaaggagc taaccgcttt tttgcacaac   5940 atggggatc atgtaactcg ccttgatcgt tgggaaccgg agctgaatga agccatacca   6000
aacgacgagc gtgacaccac gatgcctgta gcaatggcaa caacgttgcg caaactatta   6060
actggcgaac tacttactct agcttcccgg caacaattaa tagactggat ggaggcggat   6120
aaagttgcag gaccacttct gcgctcggcc cttccggctg gctggtttat tgctgataaa   6180
tctggagccg gtgagcgtgg gtctcgcggt atcattgcag cactgggcc agatggtaag   6240 ccctcccgta tcgtagttat ctacacgacg gggagtcagg caactatgga tgaacgaaat   6300
agacagatcg ctgagatagg tgcctcactg attaagcatt ggtaactgtc agaccaagtt   6360
tactcatata tactttagat tgatttaaaa cttcatttt aatttaaaag gatctaggtg   6420
aagatccttt ttgataatct catgaccaaa atcccttaac gtgagttttc gttccactga   6480
gcgtcagacc ccgtagaaaa gatcaaagga tcttcttgag atcctttttt tctgcgcgta   6540
atctgctgct tgcaaacaaa aaaccaccg ctaccagcgg tggtttgttt gccggatcaa   6600
gagctaccaa ctcttttttcc gaaggtaact ggcttcagca gagcgcagat accaaatact   6660
gttcttctag tgtagccgta gttaggccac cacttcaaga actctgtagc accgcctaca   6720
tacctcgctc tgctaatcct gttaccagtg gctgctgcca gtggcgataa gtcgtgtctt   6780
accgggttgg actcaagacg atagttaccg gataaggcgc agcggtcggg ctgaacgggg   6840
ggttcgtgca cacagcccag cttggagcga acgacctaca ccgaactgag atacctacag   6900
cgtgagctat gagaaagcgc cacgcttccc gaagggagaa aggcggacag gtatccggta   6960
agcggcaggg tcgaacagg agagcgcacg agggagcttc caggggaaa cgcctggtat   7020 ctttatagtc ctgtcgggtt tcgccacctc tgacttgagc gtcgattttt gtgatgctcg   7080 tcagggggc ggagcctatg gaaaaacgcc agcaacggat gcgccgcgtg cggctgctgg   7140
agatggcgga cgcgatggat atgttctgcc aagggttggt ttgcgcattc acagttctcc   7200
gcaagaattg attggctcca attcttggag tggtgaatcc gttagcgagg tgccgccggc   7260
ttccattcag gtcgaggtgg cccggctcca tgcaccgcga cgcaacgcgg ggaggcagac   7320
aaggtatagg gcggcgccta caatccatgc caacccgttc catgtgctcg ccgaggcggc   7380
ataaatcccc gtgacgatca gcggtccaat gatcgaagtt aggctggtaa gagccgcgag   7440
cgatccttga agctgtccct gatggtcgtc atctacctgc ctggacagca tggcctgcaa   7500
cgcgggcatc ccgatgccgc cggaagcgag aagaatcata tgggggaagg ccatccagcc   7560
tcgcgtcggg gagcttttg caaaagccta ggcctccaaa aaagcctcct cactacttct   7620
```

-continued

```
ggaatagctc agaggccgag gcggcctcgg cctctgcata aataaaaaaa attagtcagc    7680
catg                                                                  7684

<210> SEQ ID NO 50
<211> LENGTH: 26
<212> TYPE: RNA
<213> ORGANISM: Unknown
<220> FEATURE:
<223> OTHER INFORMATION: Description of Unknown:
      ribozyme nucleotide sequence targeted by
      antisense oligonucleotides

<400> SEQUENCE: 50
gugcguccug gauuccacug cuaucc                                          26

<210> SEQ ID NO 51
<211> LENGTH: 166
<212> TYPE: RNA
<213> ORGANISM: Neurospora sp.

<400> SEQUENCE: 51
ugcgaagggc gucgucgccc cgagcgguag uaagcaggga acucaccucc aauuugagua      60
cugaaauugu cguagcaguu gacuacuguu augugauugg ugaggcuaag ugacgguauu     120
ggcguaaguc aguauugcag cacagcacaa gcccgcuugc gagaau                    166

<210> SEQ ID NO 52
<211> LENGTH: 86
<212> TYPE: RNA
<213> ORGANISM: Dolichopoda schiavazzii

<400> SEQUENCE: 52
caugaugugu guucccucug ccccgcugau gaggucaggg aagaccgaaa gugucgacuc      60
uacggggcua uaacaugcaa uggugg                                          86

<210> SEQ ID NO 53
<211> LENGTH: 62
<212> TYPE: RNA
<213> ORGANISM: Tobacco ringspot virus

<400> SEQUENCE: 53
auacccuguc accggaugug cuuuccgguc ugaugagucc gugaggacga aacaggacug      60
uc                                                                    62
```

SELF-CLEAVING RIBOZYMES AND USES THEREOF

RELATED APPLICATIONS

This application is a continuation application of and claims priority to U.S. patent application Ser. No. 13/471,255, filed May 14, 2012, which is a continuation application of and claims priority to U.S. patent application Ser. No. 12/715,104, filed Mar. 1, 2010, which is a continuation application of and claims priority to U.S. patent application Ser. No. 10/990,355, filed Nov. 15, 2004, which claims the benefit of priority of U.S. Provisional Patent Application Ser. No. 60/519,941, filed Nov. 14, 2003, each of which is hereby incorporated by reference in its entirety.

BACKGROUND OF THE INVENTION

RNA enzymes (ribozymes) are being developed as treatments for a variety of diseases ranging from inborn metabolic disorders to viral infections and acquired diseases such as cancer. Ribozymes can be used both to down-regulate and to repair pathogenic genes. In some instances, short-term exogenous delivery of stabilized RNA is desirable, but many treatments will require viral-mediated delivery to provide long-term expression of the therapeutic catalyst. Although some variations on naturally occurring ribozymes are available, they have not been very effective in mammalian cells. There is a need to develop modified ribozymes that show improved activity and function in mammalian cells with high efficiency. These ribozymes are useful for developing regulated gene expression systems and have great therapeutic values.

SUMMARY OF THE INVENTION

The present invention relates to compositions and methods for novel ribozyme-based gene regulation systems that function in mammalian cells. In certain aspects, the present invention provides a self-cleaving ribozyme, which efficiently cleaves an RNA molecule that comprises the self-cleaving ribozyme in a mammalian cell. The term "ribozyme" as used herein, include naturally-occurring (wildtype) ribozymes and modified ribozymes (referred to as mutants or variants). An exemplary ribozyme of the invention is a schistosome ribozyme and mutants thereof.

In certain embodiments, the present invention relates to self-cleaving schistosome RNA mutant motifs, also referred to as schistosome RNA mutant motifs, schistosome ribozyme mutants and modified schistosome ribozymes. These terms are used herein interchangeably. The self-cleaving schistosome RNA mutant motifs of the invention include a modification at a position in a self-cleaving schistosome RNA motif that results in modulation or alteration of the cleaving activity of the self-cleaving schistosome RNA motif. Self-cleaving schistosome RNA motifs or schistosome ribozymes are members of the hammerhead ribozyme family and are characterized by their secondary structure. Hammerhead ribozymes are composed of structural elements including three helices, referred to as stem I, stem II and stem III, and joined at a central core of 11-12 single strand nucleotides. Hammerhead ribozymes may also contain loop structures extending from some or all of the helices. These loops are numbered according to the stem from which they extend (e.g., loop I, loop II, and loop III). Schistosome RNA mutants of the present invention differ from a naturally occurring self-cleaving schistosome RNA by one or more modifications, which can be addition, deletion, substitution and/or alteration of at least one (one or more) nucleotide. Such modifications can result in addition of structural elements, such as addition of a loop or stem; lengthening or shortening of an existing stem or loop; changes in the composition or structure of a loop(s) or a stem(s); or any combination of these.

In one embodiment, the present invention relates to a self-cleaving schistosome RNA motif modified to include a loop on stem III. A loop on stem III is also referred to herein as a loop III. A self-cleaving schistosome RNA motif including a loop on stem III is also referred to herein as a self-cleaving schistosome RNA motif including a loop III. A self-cleaving schistosome RNA motif including a loop III is an example of a self-cleaving schistosome RNA mutant motif of the invention.

The naturally occurring self-cleaving schistosome RNA motif does not contain a loop on stem III. As described herein, addition of a loop III increases the cleaving activity of the self-cleaving schistosome RNA motif. In a particular embodiment, the loop on stem III (loop III) comprises at least three nucleotides. In one embodiment, loop III comprises 5'-UUCG-3'. In another embodiment, loop III comprises 5'-CUUCGG-3'. In another particular embodiment, loop III comprises 5'-GCUUCGGU-3'. Loops can comprise nucleotides that can base pair and result in non-loop structures. The present invention relates to self-cleaving schistosome RNA mutant motifs illustrated in the working examples.

The present invention further relates to self-cleaving schistosome RNA mutant motifs including additional structural elements or nucleotide sequences which modulate the cleaving activity the self-cleaving schistosome RNA mutant motifs described herein, such as aptamer moieties. The self-cleaving schistosome RNA mutant motifs of the present invention can comprise one or more of these additional structural elements and nucleotide sequences.

The present invention further relates to the use of aptamer sequences to control the cleaving activity of the self-cleaving schistosome RNA mutant motifs of the invention. An aptamer is a nucleotide sequence which can be bound by an effector molecule; an effector molecule is a ligand which binds the aptamer. Aptamer sequences can be grafted onto a self-cleaving schistosome RNA mutant motif at a location such that the cleaving activity of the self-cleaving schistosome RNA mutant motif can be controlled by binding of an effector to the aptamer sequence. Cleaving activity of the self-cleaving schistosome RNA mutant motif can be modulated by binding of an effector to an aptamer sequence that is grafted onto the self-cleaving schistosome RNA mutant motif at a location such that the cleaving activity is controlled by binding of the effector to the aptamer sequence. Grafting, as used herein, refers to the incorporation or addition of the aptamer sequence into the self-cleaving schistosome RNA mutant motif. Grafting can be within the self-cleaving schistosome RNA mutant sequence, such as, for example, an insertion within stem I sequences. Alternatively, grafting can be outside of the normal secondary structure of the self-cleaving schistosome RNA mutant motif in a manner similar to the loop III modifications. Additionally, an aptamer can be grafted onto stem II, stem III, loop I, loop II, loop III, the nucleotide core or a combination of two or more of the aforementioned structural elements of the self-cleaving schistosome RNA mutant motif. The present invention relates to nucleic acids, constructs (DNA or RNA) which encode the novel self-cleaving schistosome RNA mutant motifs and schistosome RNA, described and illustrated herein. Constructs, such as DNA constructs, can be used alone or in a vector, such as a plasmid or a viral vector.

The present invention provides DNA constructs comprising: (a) a promoter; (b) nucleic acid encoding a nucleic acid product and operably linked to the promoter; and (c) nucleic acid encoding a self-cleaving schistosome RNA mutant motif as described herein. The nucleic acid encoding the self-cleaving schistosome RNA mutant motif can be 5' of the nucleic acid encoding the nucleic acid product or 3' of the nucleic acid encoding the nucleic acid product, and is operably linked to the promoter. The term "promoter" refers to a nucleic acid which, when operably linked to nucleic acid encoding a nucleic acid product, is sufficient for initiation of transcription of the nucleic acid encoding the nucleic acid product to be expressed. Transcription of the nucleic acid encoding the nucleic acid product and the nucleic acid encoding the self-cleaving schistosome RNA mutant motif produces a mRNA comprising the self-cleaving schistosome RNA mutant motif and mRNA encoding the nucleic acid product. The cleaving activity of the self-cleaving schistosome RNA mutant motif controls cleavage of the mRNA and, as a result, expression of the nucleic acid product; the self-cleaving schistosome RNA mutant motif is located in the mRNA at a position such that the nucleic acid product is not expressed when the mRNA is cleaved. As used herein, a "nucleic acid product" is a protein or polypeptide, DNA or RNA other than a self-cleaving schistosome RNA mutant motif of the invention. In a particular embodiment, the nucleic acid product is a therapeutic protein.

Under conditions appropriate for transcription of the nucleic acid encoding the nucleic acid product and the nucleic acid encoding the self-cleaving schistosome RNA mutant motif, an mRNA of the nucleic acid product and the self-cleaving schistosome RNA mutant motif are produced. Self-cleavage of the mRNA by the self-cleaving schistosome RNA mutant motif prevents expression of the nucleic acid product. Treatment of a cell or an individual, in which the instant DNA constructs are present, with an agent such as a drug (e.g., an antibiotic) or other molecule or composition, which inhibits (totally or partially) cleaving activity of the self-cleaving schistosome RNA mutant motif, results in expression of the nucleic acid product encoded by the mRNA.

In a specific embodiment, the invention provides DNA constructs comprising: (a) a promoter; (b) nucleic acid encoding a nucleic acid product operably linked to the promoter; and (c) nucleic acid encoding a self-cleaving schistosome RNA mutant motif of the invention which includes an aptamer grafted onto the self-cleaving schistosome RNA mutant motif at a location such that the cleaving activity of the self-cleaving schistosome RNA mutant motif can be controlled (is regulatable) by binding of an effector to the aptamer. Binding of an effector to the aptamer results in modulation (induction, enhancement, reduction, inhibition (total or partial) or regulation) of the cleaving activity of the self-cleaving schistosome RNA mutant motif. If the binding of the effector to the aptamer reduces or inhibits the cleaving activity of the self-cleaving schistosome RNA mutant motif, cleavage of the mRNA does not occur or is reduced, and the nucleic acid product is expressed. If the binding of the effector to the aptamer does not inhibit the cleaving activity of the self-cleaving schistosome RNA mutant motif, the mRNA is cleaved and as a result, the nucleic acid product is not expressed (not produced).

In another specific embodiment, the DNA constructs of the invention comprise nucleic acid encoding two or more (multiple) self-cleaving schistosome RNA mutant motifs of the invention. Multiple self-cleaving schistosome RNA mutant motifs can comprise the same or different self-cleaving schistosome RNA mutant motifs. Multiple self-cleaving schistosome RNA mutant motifs encoded by a nucleic acid are joined 5' to 3'. For example, the 3' terminus of the nucleic acid encoding the first self-cleaving schistosome RNA mutant motif is joined to the 5' terminus of the nucleic acid encoding the next self-cleaving schistosome RNA mutant motif. Optionally, the two self-cleaving schistosome RNA mutant motifs can be separated by a nucleic acid linker. Generally, the nucleic acid encoding the self-cleaving schistosome RNA mutant motif (one or more) is upstream of the nucleic acid encoding the nucleic acid product. Thus, the order of the components (5' to 3') in the present invention can be promoter—nucleic acid encoding a self-cleaving schistosome RNA mutant motif—nucleic acid encoding a nucleic acid product.

In addition to nucleic acid encoding a nucleic acid product to be expressed, vectors of the present invention can further comprise additional components, such as an enhancer, targeting sequences, transcriptional binding sites, and backbone nucleic acids.

The present invention relates to host cells comprising a DNA construct of the present invention. The construct comprises: (a) a promoter; (b) nucleic acid encoding a self-cleaving schistosome RNA mutant motif of the invention; and (c) nucleic acid encoding a nucleic acid product operably linked to the promoter. The nucleic acid encoding the self-cleaving schistosome RNA mutant motif and the nucleic acid encoding the nucleic acid product are downstream of the promoter. Transcription of the nucleic acid of (b) and the nucleic acid of (c) produces a mRNA comprising the self-cleaving schistosome RNA mutant motif and mRNA encoding the nucleic acid product. The cleaving activity of the self-cleaving schistosome RNA mutant motif controls cleavage of the mRNA and, as a result, expression of the nucleic acid product. In a specific embodiment, host cells of the invention comprise a nucleic acid encoding an aptamer which is grafted onto a self-cleaving schistosome RNA mutant motif, as described above. Optionally, host cells can also comprise a nucleic acid encoding two or more (e.g., multiple) schistosome self-cleaving schistosome RNA mutant motifs of the invention.

In certain embodiments, the invention relates to packaging cell lines useful for generating recombinant viral vectors and viruses of the invention. It also relates to construction of such cell lines and to methods of using the recombinant viral vectors and viruses to modulate production of a nucleic acid product in vitro, in vivo and ex vivo. Cell lines useful for generating recombinant viral vectors and viruses of the invention are produced by transfecting host cells, such as mammalian host cells, with a viral vector or virus of the invention.

The present invention relates to the use of the self-cleaving schistosome RNA mutant motifs described herein in methods of modulating expression of a nucleic acid product in a host cell or an individual. Expression of the nucleic acid product is modulated through the control of the cis-cleavage of a mRNA which encodes for the nucleic acid product. By modulating is meant inducing, enhancing (increasing), reducing, inhibiting (total or partial) or regulating a process. In a particular embodiment, modulating expression refers to the ability to increasing (enhancing) expression of the nucleic acid product. In another particular embodiment, modulating expression refers to reducing expression of the nucleic acid product. Thus, modulation can be positive (increase) or negative (decrease). By regulate is meant the ability to control the rate and/or extent to which a process occurs. For example, regulating activity of a self-cleaving RNA motif refers to controlling the rate and extent to which activity of the self-cleaving RNA motif occurs. Regulating expression of a nucleic acid refers to controlling the rate and extent to which expression of the nucleic acid product occurs.

The present invention relates to a method of modulating expression of a nucleic acid product in a host cell comprising introducing into the host cell a DNA construct of the invention comprising: (a) a promoter; (b) a nucleic acid encoding a nucleic acid product operably linked to the promoter; and (c) a nucleic acid encoding a self-cleaving schistosome RNA mutant motif, such that transcription of the nucleic acids produces a RNA molecule comprising the self-cleaving schistosome RNA mutant motif and a mRNA encoding the nucleic acid product, wherein the self-cleaving schistosome RNA mutant motif is capable of cleaving the RNA intramolecularly. Expression in cells in accordance with the present invention is modulated through control of the cleavage of a mRNA encoding the nucleic acid product. Cleavage of the mRNA is controlled through activity of a self-cleaving schistosome RNA mutant motif, which is located in the mRNA at a position such that the nucleic acid product is not expressed when the self-cleaving schistosome RNA mutant motif is expressed. Under conditions which permit expression of the self-cleaving schistosome RNA mutant motif, the mRNA is cleaved and, as a result, the nucleic acid product encoded is not produced. In this method, the host cell comprising the DNA construct is cultured in the presence of an agent, such as a drug (e.g., antibiotic) or other molecule or composition, which inhibits or reduces cleaving activity of the self-cleaving schistosome RNA mutant motif such that the nucleic acid product encoded by the mRNA is expressed. The DNA constructs used in this method can further comprise nucleic acid encoding an aptamer which is at a position such that the cleaving activity of the self-cleaving schistosome RNA motif is regulatable by the binding of an effector to the aptamer and/or nucleic acid encoding multiple self-cleaving schistosome RNA mutant motifs as described herein.

The present invention also relates to a method of expressing or modulating expression of a nucleic acid product in an individual (e.g., a human or other mammal or vertebrate). The method comprises modulating expression of a nucleic acid product from a DNA construct of the invention which is present in (contained in) cells in the individual. The DNA construct comprises nucleic acid encoding the nucleic acid product and nucleic acid encoding a self-cleaving schistosome RNA mutant motif of the invention whose activity can, in turn, be modulated by an agent when the nucleic acid product is to be expressed. Transcription of the nucleic acid encoding the nucleic acid product and the nucleic acid encoding the self-cleaving schistosome RNA mutant motif produces a mRNA comprising the self-cleaving schistosome RNA mutant motif and mRNA encoding the nucleic acid product.

In one embodiment, expression of a nucleic acid product is effected by administering an antibiotic to an individual, some of whose cells contain a DNA construct of the present invention. The DNA construct comprises: (a) a promoter; (b) nucleic acid encoding the nucleic acid product operably linked to the promoter; and (c) nucleic acid encoding a self-cleaving schistosome RNA mutant motif of the invention. Transcription of the nucleic acid of (b) and the nucleic acid of (c) produces mRNA comprising the self-cleaving schistosome RNA mutant motif and mRNA encoding the nucleic acid product. As a result, activity of the encoded self-cleaving schistosome RNA mutant motif is inhibited (partially or totally), with the result that the nucleic acid product of interest is expressed in the individual. The DNA construct can be introduced into cells in the individual in vivo (e.g., by introducing the DNA construct) into a tissue or body fluid of the individual) or ex vivo (e.g., by introducing the DNA construct into cells obtained from the individual or from another (different) individual or source and then introducing the resulting cells into the individual). In either case, administration of an antibiotic results in inhibition of the activity of the self-cleaving schistosome RNA mutant motif and, as a result, the mRNA coding for the nucleic acid product of interest is not cleaved and the nucleic acid product of interest is expressed.

In one embodiment, the method is carried out by: (a) obtaining cells from an individual and maintaining the cells under appropriate conditions for cell growth and cell division; (b) introducing into the cells a DNA construct of the invention; (c) returning the cells produced in step (b) to the individual; and (d) administering to the individual an agent which inhibits cleavage of the self-cleaving schistosome RNA mutant motif. In a particular embodiment, the DNA construct of the invention comprises: (a) a promoter; (b) nucleic acid encoding a nucleic acid product to be expressed, operably linked to the promoter; and (c) nucleic acid encoding a self-cleaving schistosome RNA mutant motif of the invention. The nucleic acid encoding the nucleic acid product to be expressed and the nucleic acid encoding the self-cleaving schistosome RNA mutant motif are downstream of the promoter. Transcription of the nucleic acid encoding the nucleic acid product and the nucleic acid encoding the self-cleaving schistosome RNA mutant motif produces a mRNA comprising the self-cleaving schistosome RNA mutant motif and mRNA encoding the nucleic acid product. In this particular embodiment of the method of expressing a nucleic acid product in an individual, the agent is, for example, an antibiotic.

In one embodiment, the present invention relates to a method of regulating expression of an endogenous gene (a gene resident in a cell as the cell was obtained) to produce a nucleic acid product and compositions useful in the method. The endogenous gene can be one which is expressed ("on") in the cell or one which is normally not expressed ("off") in the cell but whose expression is or has been turned on or activated. In this embodiment, a DNA construct encoding a self-cleaving schistosome RNA mutant motif of the invention is introduced into genomic DNA of cells in such a position that, in mRNA produced by the cells, the self-cleaving schistosome RNA mutant motif is in a location which results in control of expression of the encoded nucleic acid product. In the absence of an agent which inhibits expression of the self-cleaving schistosome RNA mutant motif, cleavage occurs and the nucleic acid product is not expressed. In the presence of such an agent, cleaving activity is inhibited and the nucleic acid product is expressed. In one embodiment, DNA encoding a self-cleaving schistosome RNA mutant motif of the invention can be introduced alone or in a vector, into genomic DNA between the promoter operably linked to (controlling expression of) the endogenous gene encoding the nucleic acid product, in such a manner that the endogenous gene remains operably linked to the promoter. In an alternative embodiment, DNA encoding a self-cleaving schistosome RNA mutant motif of the invention can be introduced alone or in a vector, into genomic DNA 3' of the endogenous gene encoding the nucleic acid product. The promoter which is operably linked to the endogenous gene to be expressed can be the naturally occurring (endogenous) promoter for the gene or can be an exogenous promoter introduced into genomic DNA. The resulting cells can be used, as described herein, to modulate production of the nucleic acid product in an individual.

In certain embodiments, expression of a nucleic acid product is effected by administering an antisense oligonucleotide of a self-cleaving schistosome RNA mutant motif to a cell or an individual. Some of those cells contain a DNA construct of the present invention, wherein the DNA construct comprises: (a) a promoter; (b) nucleic acid encoding the nucleic acid product operably linked to the promoter; and (c) nucleic acid encoding a self-cleaving schistosome RNA mutant motif of the invention. Transcription of the nucleic acid of (b) and the nucleic acid of (c) produces mRNA comprising the self-cleaving schistosome RNA mutant motif and mRNA encoding the nucleic acid product. As a result, activity of the encoded self-cleaving schistosome RNA mutant motif is inhibited (partially or totally) by the antisense oligonucleotide, with the result that the nucleic acid product of interest is expressed in the cell or individual. Preferably, the antisense oligonucleotide base pairs with a region of the self-cleaving schistosome RNA mutant motif as depicted in SEQ ID NO: 50. For example, the antisense oligonucleotide is a modified oligonucleotide selected from the group consisting of: morpholino, phosphorothioate RNA, 2'-O-methyl RNA, and phosphorothioate 2'-O-methoxyethyl RNA.

In a particular embodiment, the present invention relates to a method of specifically inducing expression of a target gene in a cell, comprising contacting the cell with an antisense oligonucleotide which specifically inhibits a self-cleaving schistosome RNA mutant motif, wherein the self-cleaving schistosome RNA mutant motif is present in a RNA molecule encoding the target gene product. The cell comprising the RNA molecule is cultured under conditions appropriate for the antisense oligonucleotide to inhibit cleaving the RNA molecule by the self-cleaving schistosome RNA mutant motif. The method is based in part on the ability of specific oligonucleotides to discriminate different self-cleaving schistosome RNA mutant motifs. Optionally, the method of the invention may be used for the generation of multiple independent systems for gene regulation.

Similarly, the present invention relates to a method of specifically modulating (inducing or inhibiting) expression of a target gene in a cell, comprising contacting the cell with an effector which specifically binds to an aptamer, wherein the aptamer is engineered to be present in a RNA molecule encoding the target gene product and a self-cleaving schistosome RNA mutant motif. The cell comprising the RNA molecule is cultured under conditions appropriate for the interaction between the effector and the aptamer such that the interaction modulates cleaving the RNA molecule by the self-cleaving schistosome RNA mutant motif as described above. This method is based in part on the ability of specific effectors to discriminate different aptamers. Optionally, the method of the invention may be used for the generation of multiple independent systems for gene regulation.

The present invention also provides modified antisense oligonucleotides of a self-cleaving schistosome RNA mutant motif. Preferably, the antisense oligonucleotides of the invention base pair with a target region of the self-cleaving schistosome RNA mutant motif as depicted in SEQ ID NO: 50. Examples of the modified antisense oligonucleotides include, but are not limited to, morpholino, phosphorothioate RNA, 2'-O-methyl RNA, and phosphorothioate 2'-O-methoxyethyl RNA.

The present invention relates to a method of screening for an agent which inhibits the catalytic activity of a self-cleaving schistosome RNA mutant motif of the present invention comprising: (a) introducing into host cells a DNA construct of the invention which comprises: (1) a promoter, (2) nucleic acid encoding a reporter which is operably linked to the promoter and (3) nucleic acid encoding a self-cleaving schistosome RNA mutant motif of the invention, wherein the nucleic acid of (2) and the nucleic acid of (3) are downstream of the promoter, wherein the DNA construct is introduced into the host cells under appropriate conditions for expression of the nucleic acid encoding the reporter and the nucleic acid encoding the self-cleaving schistosome RNA mutant motif; (b) contacting host cells with an agent to be assessed for its ability to inhibit the catalytic activity of the self-cleaving schistosome RNA mutant motif under conditions which result in introduction of the agent into the cells; and (c) assaying reporter activity in the host cells. If reporter activity detected in the presence of the agent is greater than the reporter activity detected in the absence of the agent, the agent is identified as one which inhibits the catalytic activity of a self-cleaving schistosome RNA mutant motif.

The present invention also relates to a method of screening for an effector which binds to an aptamer (or RNA sequence) and inhibits the catalytic activity of a self-cleaving schistosome RNA mutant motif of the invention. In this method, host cells are introduced a DNA construct of the invention which comprises: (1) a promoter, (2) nucleic acid encoding a reporter operably linked to the promoter and (3) nucleic acid encoding a self-cleaving schistosome RNA mutant motif of the invention which includes an aptamer located at a position such that the cleaving activity of the self-cleaving schistosome RNA mutant motif is regulatable by binding of an effector to the aptamer, wherein the nucleic acid of (2) and the nucleic acid of (3) are downstream of the promoter, and transcription of the nucleic acid of (2) and the nucleic acid of (3) produces a mRNA comprising the aptamer-self-cleaving schistosome RNA motif (or RNA sequence-self-cleaving schistosome RNA motif) and mRNA encoding the reporter. The host cells are contacted with an agent to be assessed for its ability to bind the aptamer (or RNA sequence) under conditions appropriate for expression of the reporter and the self-cleaving schistosome RNA mutant motif, and reporter activity is assayed in the host cells. If reporter activity detected in the presence of the agent is greater than the reporter activity detected in the absence of the agent, the agent is identified as an effector which can bind to the aptamer (or RNA sequence) and inhibit the catalytic activity of a self-cleaving schistosome RNA mutant motif.

The present invention also relates to a method for producing a transgenic nonhuman animal using the self-cleaving schistosome RNA motif. In one embodiment, the transgenic animal is produced by introducing a DNA construct of the invention into a germ cell of a nonhuman animal or the germ cell of its ancestor, wherein the DNA construct comprises: (a) a promoter, (b) nucleic acid encoding a nucleic acid product operably linked to the promoter and (c) nucleic acid encoding a self-cleaving schistosome RNA mutant motif of the invention. The nucleic acid of (b) and the nucleic acid of (c) are downstream of the promoter, and transcription of the nucleic acid of (b) and the nucleic acid of (c) produces an mRNA comprising the self-cleaving schistosome RNA mutant motif and mRNA encoding the nucleic acid product.

In certain embodiments, the present invention provides a kit for regulating gene expression. For example, the kit comprises a nucleic acid comprising: (a) a schistosome ribozyme mutant sequence; and (b) a cloning site for introduction of a target nucleotide sequence to be transcribed operatively linked to the schistosome ribozyme mutant sequence. Optionally, the kit may further comprise an inhibitor of the schistosome ribozyme mutant. For example, the schistosome ribozyme mutant comprises a nucleotide sequence selected from SEQ ID NOs: 1-46. The inhibitor of the kit includes, but is not limited to, toyocamycin, 8-azaadenosine, sangivamycin, tubercidin, tubercidin-cyclic monophosphate, tubercidin-monophosphate, tubercidin-triphosphate, nebularine, tricyclic nucleoside, 5-fluorouridine, 5-bromouridine, 5-fluorouracil, Syto-83, homidium bromide, and acridine orange.

In certain embodiments, the present invention provides a method for determining the level of an inhibitor of a schistosome ribozyme mutant in a cell. In this method, a cell is introduced a DNA construct which comprises: (1) a promoter; (2) a nucleic acid encoding a reporter; and (3) a nucleic acid encoding a schistosome ribozyme mutant, wherein the nucleic acid of (2) and the nucleic acid of (3) are downstream of the promoter and operably linked to said promoter, under conditions which result in inhibition of the ribozyme mutant and expression of the reporter. The reporter activity is assayed, wherein the level of said inhibitor in the cell is identified by comparing the reporter activity with an appropriate control. Preferably, the inhibitor is 5-fluorouracil or 5-fluorouridine. In certain cases, the reporter is selected from β-galactosidase, β-glucoronidase, β-glucosidase, chloramphenicol acetyl transferase (CAT), green flourescent protein, and luciferase. Optionally, the cell is a cancer cell.

In certain embodiments, the present invention provides a method for determining the level of an inhibitor of a schistosome ribozyme mutant in a biological sample. In this method, a cell is contacted with a biological sample, wherein the cell is engineered to express a DNA construct which comprises: (1) a promoter; (2) a nucleic acid encoding a reporter; and (3) a nucleic acid encoding a schistosome ribozyme mutant, wherein the nucleic acid of (2) and the nucleic acid of (3) are downstream of the promoter and operably linked to said promoter, under conditions which result in inhibition of the ribozyme mutant and expression of the reporter. The reporter activity is assayed, wherein the level of said inhibitor in the biological sample is identified by comparing the reporter activity with an appropriate control.

In certain embodiments, the present invention provides a method of inhibiting activity of a catalytic RNA in a cell, comprising contacting a cell with an inhibitor of a schistosome ribozyme mutant. Preferably, the cell has been infected or is at risk of having infection with a virus or a pathogenic microorganism. For example, the inhibitor is selected from toyocamycin, 8-azaadenosine, sangivamycin, tubercidin, tubercidin-cyclic monophosphate, tubercidin-monophosphate, tubercidin-triphosphate, nebularine, tricyclic nucleoside, 5-fluorouridine, 5-bromouridine, 5-fluorouracil, Syto-83, homidium bromide, and acridine orange. In certain cases, the inhibitor is an antisense oligonucleotide, including a modified antisense oligonucleotide (e.g., morpholino, phosphorothioate RNA, 2'-O-methyl RNA, or phosphorothioate 2'-O-methoxyethyl RNA).

In certain embodiments, the present invention provides a method of inhibiting infection by a virus or a pathogenic microorganism in a cell, comprising contacting a cell with an inhibitor of a schistosome ribozyme mutant. The infection may be caused by a virus (e.g., a human immunodeficiency virus, a herpes virus, a hepatitis virus, or a human papillomavirus) or a pathogenic microorganism (e.g., *Notophthalmus viddescens*, *Ambystoma talpoideum*, *Amphiuma tridactylum*, and *Schistosoma mansoni*). The cell can be an animal cell (e.g., a mammalian cell) or a plant cell (e.g., tobacco).

BRIEF DESCRIPTION OF THE DRAWINGS

FIGS. 1a-1g show the strategy for controlling gene expression via the modulation of RNA self-cleavage and optimization of Schistosome Sml rz self-cleavage activity. (a) When a cis-acting hammerhead rz is embedded in the mRNA, self-cleavage leads to the destruction of the mRNA and the absence of gene expression. However, an inactive mutant or the administration of specific inhibitors of the rz leads to the generation of intact mRNA's and protein expression. (b) The reporter gene expression vector pMD used for transfection assay, and the positions where rz were placed. Cap site at the very beginning of the mRNA; A site upstream of the intron; B, C, and D site in the intron; E site immediately upstream of the translation start; F and G sites in the 3'-untranslated region. (c) to (g): optimization of Schistosome Sml activity (SEQ ID NOs: 1, 2, 3, 4, 5, 5, 6, 6, 5, 7, 8, and 9, respectively). (c) and (d), rz inserted at position A of pMD vector; (e) to (g) at position E of vector. Corresponding inactive mutants contained an A14 to G substitution. Name of rz is shown at left; cleavage activity at right. (c) Cricket Pst3 motif (SEQ ID NO: 1). Nucleotide numbering follows nomenclature of Hertel et al., 1992. (d) Schistosome Sml motif. The original Sml lacked loop III and exhibited no activity in cells (SEQ ID NO: 2). A tetraloop 5'-UUCG-3' was grafted onto an extended stem III (N27, set forth in SEQ ID NO: 3) and resulted in 19-fold increase in activity. Specific modification at nucleotide position 7 (C to U) in the conserved catalytic core (N53, set forth in SEQ ID NO: 4) and a change in distal stem III (N73, set forth in SEQ ID NO: 5) led to a 62-fold increase in activity. (e) Transfer of the N73 ribozyme from position A to E of the vector (N79, set forth in SEQ ID NO: 5, respectively) enhanced the activity to 225-fold. Changes in stem I of N79 near the core (N99, set forth in SEQ ID NO: 6) or near the restriction insertion site (N117, set forth in SEQ ID NO: 6) further enhanced activity. Black line identifies the sequence targeted by antisense morpholino oligonucleotides (SEQ ID NO: 50). (f) The sequence of N79 is shown (SEQ ID NO: 5). Shortening of stem I (N93, set forth in SEQ ID NO: 7, and N94, set forth in SEQ ID NO: 8) vastly reduced rz cleavage activity. (g) Single nucleotide changes in loop I of the N107 rz decreased its activity dramatically (N107, set forth in SEQ ID NO: 9). The N107 rz is a variant of N79 in which two 'AUG' were replaced by G̲UG and AC̲G to eliminate the potential start codons. The ±signs indicate standard deviation from mean of at least four independent measurements.

FIGS. 3a-3c show induction of gene expression in cultured cells via inhibition of rz self-cleavage. (a) Effect of morpholino oligonucleotide on N79 rz in transient transfection assay. Induction was measured by 'fold increase' in β-gal expression with vs. without morpholino application. The level of induction is also shown as a percentage relative to the expression level of inactive rz. The target for the oligonucleotide is shown in FIG. 1e. (b) Induction of luciferase expression by toyocamycin in a stable cell line carrying an expression construct containing a double N79 rz. Cells were treated with toyocamycin for 24 hours at dosage of 0, 0.5, 1, and 1.5 μM (toxic effects were observed at concentrations higher than 1.5 Quantitative measurements of luciferase activity revealed emission of 1,555, 66,774, 242,546, 377,655 photons per second per 1000 cells respectively, as compared to a background emission of 121 from cells carrying no luciferase gene. Error bars indicate standard deviation from mean of at least four independent measurements. (c) Induction by toyocamycin at the RNA level as revealed by northern blot analyses. Experimental conditions were similar to that of (b). RNA was purified from the nucleus 'N' or the cytoplasm 'C' after 24 hours of treatment.

FIGS. 5A-5F show sequences of some self-cleaving schistosome RNA mutant motifs, locations of these nucleotide modifications, and their self-cleaving activities in mammalian cells. Changes in the resultant ribozyme activity were measured by monitoring the fold of difference in the reporter beta-galactosidase activity. The sequences of the illustrated schistosome RNA mutant motifs are identified as following:

FIG. 5A: N5, SEQ ID NO: 2; N27, SEQ ID NO: 3; N53, SEQ ID NO: 4; N73, SEQ ID NO: 5; N79, SEQ ID NO: 5; N99, SEQ ID NO: 6; N117, SEQ ID NO: 6;

FIG. 5B: N53, SEQ ID NO: 4, N65-2, SEQ ID NO: 10; N65-3, SEQ ID NO: 11; N65-4, SEQ ID NO: 12; N66-1, SEQ ID NO: 13; N66-2, SEQ ID NO: 14; N66-3, SEQ ID NO: 15; N66-4, SEQ ID NO: 16;

FIG. 5C: N67, SEQ ID NO: 17; N79, SEQ ID NO: 5; cd28-N2, SEQ ID NO: 18;

FIG. 5D: N64, SEQ ID NO: 19, N64-2, SEQ ID NO: 20; N64-4, SEQ ID NO: 21; N64-5, SEQ ID NO: 22;

FIG. 5E: N107, SEQ ID NO: 23; N106-ACC, SEQ ID NO: 24; N108-CCC, SEQ ID NO: 25, N108-GCC, SEQ ID NO: 26; N108-UAC, SEQ ID NO: 27; N108-UGC, SEQ ID NO: 28; N108-UUC, SEQ ID NO: 29; N108-UCA, SEQ ID NO: 30; N108-UCG, SEQ ID NO: 31; N108-UCU, SEQ ID NO: 32; N95, SEQ ID NO: 33; N102, SEQ ID NO: 34;

FIG. 5F: N79, SEQ ID NO: 5; N93, SEQ ID NO: 7; N94, SEQ ID NO: 8; N96, SEQ ID NO: 35; N97, SEQ ID NO: 36; N98, SEQ ID NO: 37; N99, SEQ ID NO: 6; N100, SEQ ID NO: 38; N95, SEQ ID NO: 33; N101, SEQ ID NO: 39; N103, SEQ ID NO: 40; N104, SEQ ID NO: 41; N105, SEQ ID NO: 42; N106, SEQ ID NO: 43; N107, SEQ ID NO: 44; Ncd28-N1, SEQ ID NO: 45; Doxy3N, SEQ ID NO: 46.

FIGS. 8A-8B shows the nucleotide sequence of an exemplary vector named HDM-nLacZ; SEQ ID NO: 49.

FIG. 2 shows structures of four small ribozymes: (a) the hammerhead; (b) hairpin; (c) hepatitis delta virus; and (d) *Neurospora* VS ribozymes. Hammerhead ribozymes (a) are composed of three stem helices designated I, II, and III. The core region comprises unpaired nucleotides. Loop structures can be present branching off stems I, II, and III.

DETAILED DESCRIPTION OF THE INVENTION

In certain embodiments, the present invention provides compositions and methods for controlling gene expression with a ribozyme-based system. The term "ribozyme" as used herein, includes naturally-occurring (wildtype) ribozymes and modified ribozymes (also referred to as mutants or variants). In particular, the invention relates to novel self-cleaving ribozyme motifs (e.g., schistosome ribozymes), nucleic acids encoding at least one self-cleaving ribozyme motif, regulators (e.g., inhibitors) of the self-cleaving ribozyme motifs, and methods involving uses of the ribozyme motifs and its regulators for diagnostic and therapeutic applications. Although the application mostly discusses compositions and methods derived from a particular ribozyme (schistosome ribozyme), one of ordinary skill in the art will readily recognize that similar compositions and methods can be derived from any other ribozyme which functions in mammalian cells.

In certain embodiments, the present invention relates to self-cleaving ribozymes that are functional in mammalian cells. The term "functional self-cleaving ribozyme" refers to a self-cleaving ribozyme that efficiently cleaves an RNA molecule in which the ribozyme is embedded and leads to at least 90% (preferably 95%, 98%, 99% or 100%) reduction in the RNA molecule relative to an inactive ribozyme. For example, the activity of the self-cleaving ribozyme can be assayed by the methods described in the working examples below.

As one example, the ribozyme of the invention is a hammerhead ribozyme (wildtype or mutants) selected from cherry small circular RNA+ (Scc+), cherry small circular RNA (Scc−), Lucerne transient streak virusoid+ (sLTSV+), Lucerne transient streak virusoid− (sLTSV−), Tobacco ringspot virus satellite RNA+ (sTRSV+), Arabis mosaic virus (sArMV), Chicory yellow mottle virus satellite RNA (sCYMV), Barley yellow dwarf virus satellite RNA− (sBYDV−), Barley yellow dwarf virus satellite RNA+ (sBYDV+), Peach latent mosaic virus RNA+ (PLMVd+), Peach latent mosaic virus RNA-(PLMVd−), Chrysanthemum chlorotic mottle viroid+ (CChMVd+), Chrysanthemum chlorotic mottle viroid− (CChMVd−), Subterraneurn clover mottle virusoid (vSCMoV), and velvet tobacco mottle virusoid (vVTMoV).

Figure 1A:
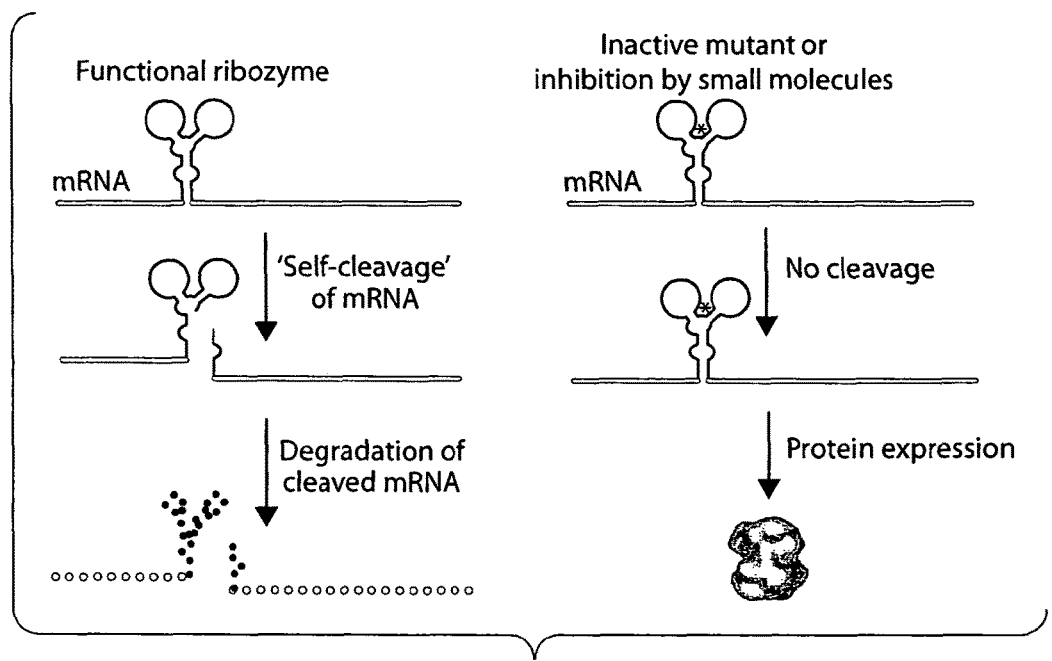
Figure 1B:
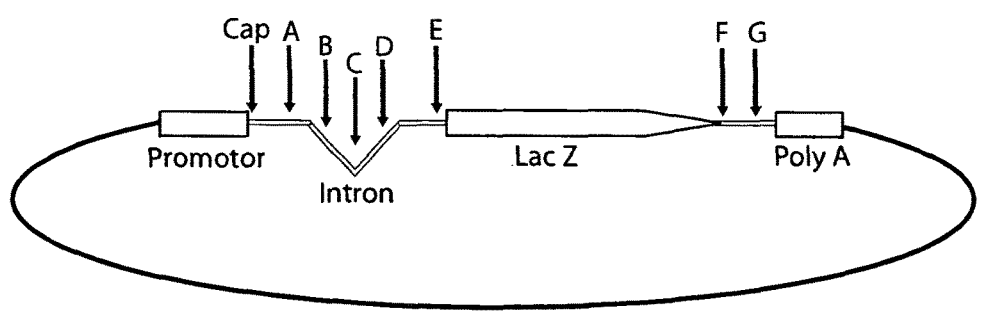
Figure 1C:
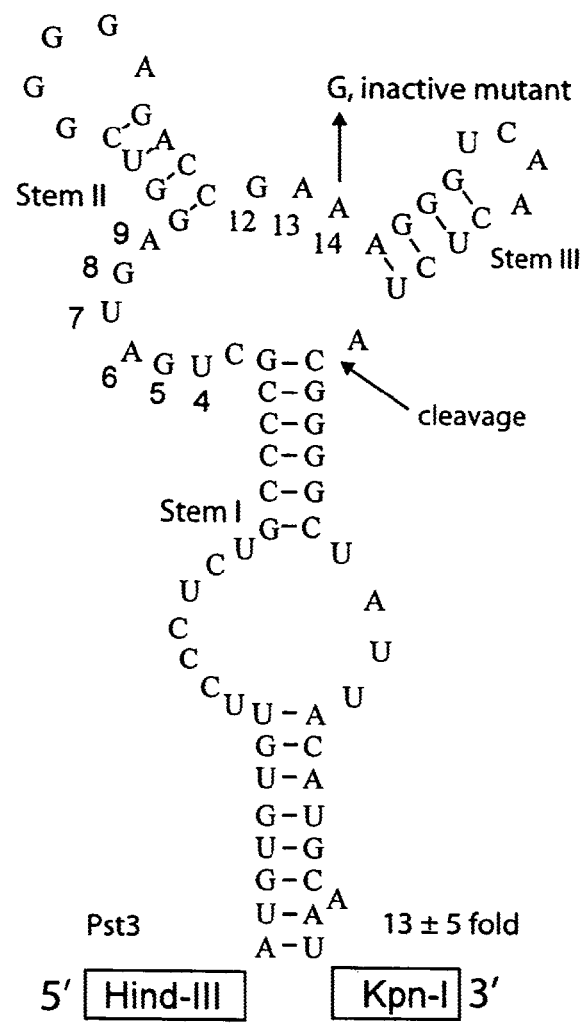

As another example, the ribozyme of the invention is a hammerhead ribozyme (wildtype or mutants) selected from *Notophthalmus viddescens* satellite RNA (newt), *Ambystoma talpoideum* (*Am. ta.*), *Amphiuma tridactylum* (*Am. tr.*), *Schistosoma mansoni* hammerhead ribozyme (Schistozyme), *D. bacceffli* cricket hammerhead ribozyme (cricketzyme A), *D. schiavazzii* cricket hammerhead ribozyme (cricketzyme B), and Avocado sunblotch viroid+ (ASBV+). A specific example of the ribozyme sequence is the *Dolichopoda* cave cricket as illustrated in FIG. 1C (SEQ ID NO: 1).

As a further example, the ribozyme of the invention can be other self-cleaving ribozymes, such as a hepatitis delta virus (HDV) ribozyme, a hairpin ribozyme, and a *Neurospora* Varkud satellite (VS) ribozyme (see, e.g., FIG. 10). Like hammerhead ribozymes, these three self-cleaving ribozymes are found in viral, virusoid, or satellite RNA genomes, and process the products of rolling circle replication into genome-length strands (Doherty et al., 2001, Annu Rev Biophys Biomol Struct. 30:457-75; Branch et al., 1984, Science 223:45055).

In particular, the invention relates to novel self-cleaving schistosome RNA mutant motifs, nucleic acids encoding at least one self-cleaving schistosome RNA mutant motif, regulators (e.g., inhibitors) of the self-cleaving schistosome RNA mutant motifs, and methods involving uses of the schistosome RNA mutant motif and its regulators for diagnostic and therapeutic applications.

Self-Cleaving RNA Mutant Motifs

The self-cleaving RNA mutant motifs (e.g., schistosome mutant motifs) are also referred to as ribozyme mutants or modified ribozyme motifs). These modified ribozymes can be used to modulate expression of a desired nucleic acid product in cells. Expression in cells in accordance with the invention is modulated through control of the activity of a self-cleaving RNA mutant motif of the invention. In particular, expression of a nucleic acid product is modulated by the activity of a self-cleaving RNA mutant motif which is located in the mRNA at a position such that the desired nucleic acid product is not expressed when the mutant motif is active. Under conditions which are appropriate for expression of the self-cleaving RNA mutant motif, the mRNA is cleaved and as a result, the desired nucleic acid product encoded by the mRNA is not produced (FIG. 1A). Administration to cells of an agent such as a drug or other molecule or composition, which inhibits or reduces the cleaving activity of the self-cleaving RNA mutant motif, prevents cleavage of the mRNA and, therefore, the nucleic acid product is expressed (FIG. 1 A).

Ribozymes are RNA structural motifs of about 40-60 nucleotides that can self-cleave in a sequence-specific manner. The term "ribozyme" refers to an RNA sequence that hybridizes to a complementary sequence in a substrate RNA and cleaves the substrate RNA in a sequence specific manner at a substrate cleavage site. Typically, a ribozyme contains a catalytic region flanked by two binding regions. The ribozyme binding regions hybridize to the substrate RNA, while the catalytic region cleaves the substrate RNA at a substrate cleavage site to yield a cleaved RNA product. The nucleotide sequence of the ribozyme binding regions may be completely complementary or partially complementary to the substrate RNA sequence with which the ribozyme binding regions. Generally, ribozymes are embedded in highly repetitive satellite DNA and have been identified in plant viruses, newts, cave crickets, and schistosomes.

Schistosomes are a family of parasitic blood flukes which infect humans. Recently, several members of the Schistosome family were found to encode hammerhead ribozymes (Ferbeyre et al., Mol. Cell Bio. 18:3880-3888 (1998)). Hammerhead ribozymes are one of the four known classes of self-cleaving RNA motifs and the term refers to the secondary structure of this class of ribozymes. The hammerhead secondary structure is composed of three helices, referred to as stem I, stem II and stem III, joined at a central core of 11-12 single stranded nucleotides that are necessary and sufficient for the self-cleavage reaction (Uhlenbeck, Nature, 328:596-600 (1987); and Foster and Symons, Cell, 50:9-16 (1987)). Systematic site-directed mutagenesis studies have determined that most nucleotides in the conserved core cannot undergo mutation without significant loss of catalytic activity (Ruffner et al., Biochemistry, 29: 10695-10702 (1990)). This observation was used to generate inactive self-cleaving RNA motifs used herein as negative controls in ribozyme activity assays.

Ribozymes can have additional structural elements such as loops, which are designated by the stem from which they branch. For example, schistosome ribozymes have a six nucleotide loop on stem II (loop II), as illustrated in FIG. 1c. Naturally occurring (wildtype) schistosome ribozymes include stems I-III, loops I-II, but not loop III. By loop II is meant a loop on stem II. By loop III is meant a loop on stem III. Other loops are identified similarly herein by this convention (e.g., loop I). Standard nomenclature for nucleotide position in hammerhead ribozymes is used herein (Clouet-d'Orval and Uhlenbeck, Biochemistry, 36:9087-9092 (1997)). In certain embodiments, the present invention contemplates sequences that are outside the conserved or consensus region of the ribozymes. Optionally, sequences outside of the canonical hammerhead ribozyme structure can be incorporated into the ribozyme structure. The resulting compositions are examples of self-cleaving schistosome RNA mutant motifs of the invention.

As described herein, modification or alteration of the nucleotide sequence of naturally occurring ribozymes (e.g., schistosome ribozyme) can increase or decrease their catalytic activity. As used herein, catalytic activity refers to the ability of ribozyme to autocatalytically cleave its RNA.

Self-cleaving RNA mutant motifs (e.g., schistosome ribozyme mutants) and methods disclosed in the present invention are particularly useful in exogenous control of gene expression. The present invention makes it possible to modulate expression of a nucleic acid product without the need to use special transcriptional control elements or chimeric transactivators. Thus, the present invention has a number of distinct advantages over previously-available methodologies and has broad applications in such fields as protein production, gene therapy, and developmental biology. In addition, the essential genetic element for gene regulation is very small in size and does not encode any gene product. Accordingly, it is unlikely that the introduction of the element into cells will result in any toxicity, and it should be possible to incorporate the necessary sequences for obtaining regulated expression into many different types of vectors.

An additional benefit of the methods described herein for modulating expression of a nucleic acid product is that gene regulation is not sensitive to chromosomal position, since modulation does not depend upon control of the initiation of transcription. Furthermore, in contrast to existing methods for controlling expression of a nucleic acid product, which require that specific hybrid promoters be used, it is possible to modulate expression within the context of the normal cell type specific or developmental stage specific transcriptional elements of any gene or vector. In fact, by incorporation of the essential genetic element for gene regulation within a transcriptional unit, it is even possible to provide gene regulation in the context of the normal mRNA structure used for gene expression (e.g., a structure devoid of any exogenous regulatory elements). These features may prove to be particularly important for transgenic and knockout experiments in animals designed to assess the role of a specific gene product at different stages of development, where the essential role of a gene product in embryonal development may preclude the ability to determine the role of the gene product at a later stage of development.

In certain aspects, the present invention relates to self-cleaving RNA mutant motifs (e.g., schistosome ribozyme mutants) comprising modifications that modulate or alter their catalytic activity. The modifications can either positively (increase) or negatively (decrease) modulate the catalytic activity of the self-cleaving RNA motif. In a particular embodiment, the modifications can modulate, either positively or negatively, the ability and/or rate of the self-cleaving RNA motif to self-cleave. Modifications can also have no measurable effect on the activity of the self-cleaving RNA motif. By "modification" is meant a modification (e.g., alternation or change) of the naturally occurring ribozyme structural elements or the addition of other structural elements not found in the naturally occurring ribozyme. The term "modification" is meant to include nucleotide additions, deletions or substitutions to the self-cleaving RNA motif sequence or adjacent sequences comprising the self-cleaving RNA motif. Modifications include the addition (e.g., by grafting) of stem and/or loop structures to a naturally occurring ribozyme and the modification of stem and/or loop structures of a naturally occurring ribozyme. Modifications also include the addition of one or more (multiple) aptamers to a self-cleaving RNA motif and the addition of other structural features to a self-cleaving RNA motif, such as hairpins. These modifications can be used separately or in combination with one or more other modifications and are not meant to be limiting in any way.

In one embodiment, the present invention relates to a self-cleaving schistosome RNA motif modified to include a loop on stem III. A "loop," as used herein, refers to a secondary structure in an RNA sequence in which a single-stranded RNA sequence is flanked by RNA sequences which are capable of pairing with each other to form a "stem" structure. A loop comprises at least three nucleotides, and preferably from about 3-40 nucleotides. A "loop" can include nucleotides which can base pair and result in non-loop structures. For example, a loop can include nucleotides which can base pair and optionally elongate the stem from which it branches. By "branches" is meant that the nucleotide sequence of the modification starts where the stem originally ended. By "base pair" is meant the formation of hydrogen bond(s) between two nucleic acid sequences by either traditional Watson-Crick or other non-traditional types (for example, Hoogsteen type) of interactions. A self-cleaving schistosome RNA motif including a loop on stem III is an example of a self-cleaving schistosome RNA mutant motif of the invention. Preferably, the catalytic activity of such a self-cleaving schistosome RNA mutant motif comprising a loop on stem III is greater than the catalytic activity of the corresponding naturally occurring self-cleaving schistosome RNA motif.

Figure 1E:
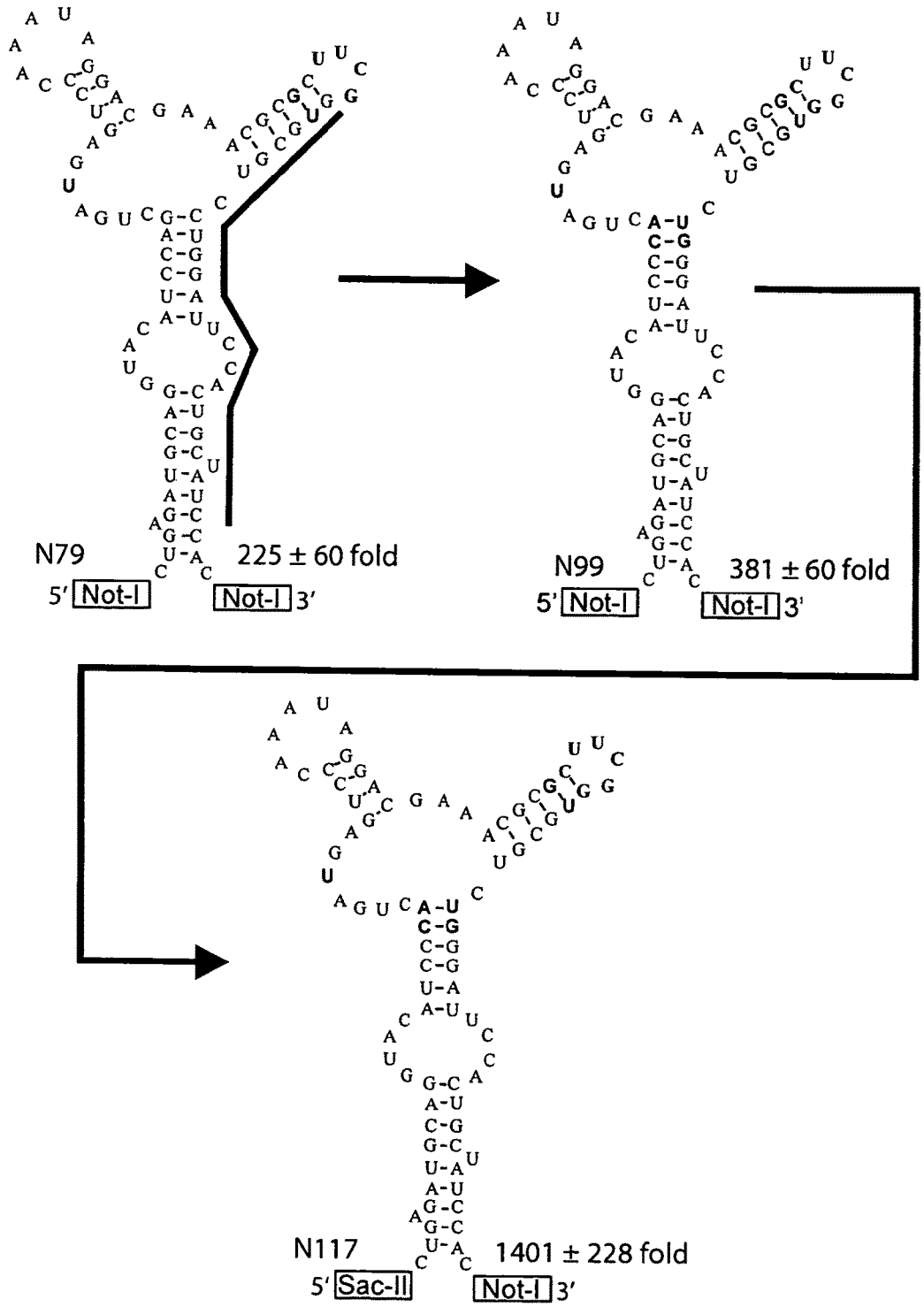
Figure 1G:
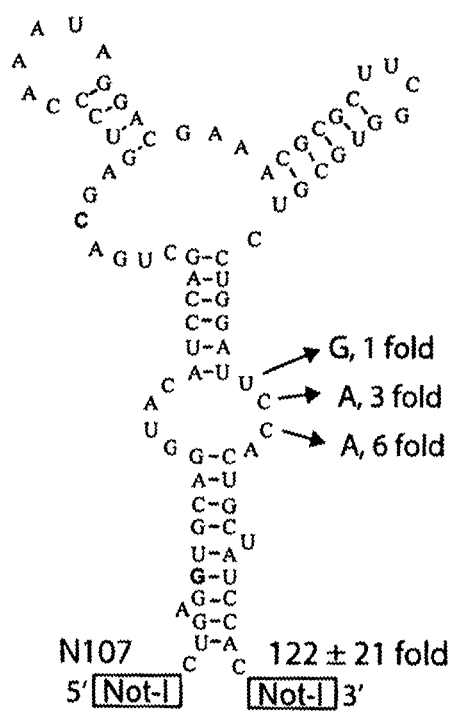

In a particular embodiment, a self-cleaving schistosome RNA mutant motif of the invention comprises a four-nucleotide loop III. In a particular embodiment, the loop comprises 5'-UUCG-3'. An exemplary self-cleaving schistosome RNA mutant motif of the invention (N99) is illustrated in FIG. 1e. The present invention also provides other self-cleaving schistosome RNA mutant motifs and their sequences in FIG. 5 (SEQ ID NOs: 2, 3, 4, 5, 5, 6, 6, 4, 10, 11, 12, 13, 14, 15, 16, 17, 5, 18, 19, 20, 21, 22, 23, 24, 25, 26, 27, 28, 29, 30, 31, 32, 33, 34, 5, 7, 8, 35, 36, 37, 6, 38, 33, 39, 40, 41, 42, 43, 44, 45, and 46, respectively).

In another embodiment, a self-cleaving schistosome RNA mutant motif of the invention comprises a six- or eight-nucleotide loop III that also elongates stem III. Examples of self-cleaving schistosome RNA mutant motifs comprising a six nucleotide loop III are illustrated in FIG. 5 (e.g., N27 and N53). Examples of self-cleaving schistosome RNA mutant motifs comprising an eight nucleotide loop III are also illustrated in FIG. 5 (e.g., N73, N79, N99, and N117).

Self-cleaving schistosome RNA mutant motifs of the invention can also include substitutions at position 5, 7 and/or 14 (e.g., C→U of the core, as illustrated in FIGS. 1 and 5). In a particular embodiment, a self-cleaving schistosome RNA mutant motif of the invention comprises a loop III and a substitution in the conserved core. In a preferred embodiment, loop III comprises 5'-UUCG-3' and a U at position 7 of the core, as illustrated in FIGS. 1 and 5 (e.g., N53, N73, N79, N99, and N117). In another embodiment, a self-cleaving schistosome RNA mutant motif of the invention comprises an addition of six nucleotides on the end of stem III and a U at position 7 of the core, as illustrated in FIGS. 1 and 5.

In certain embodiments, the present invention also relates to other self-cleaving schistosome RNA motifs illustrated in FIG. 5 (SEQ ID NOs: 2, 3, 4, 5, 5, 6, 6, 4, 10, 11, 12, 13, 14, 15, 16, 17, 5, 18, 19, 20, 21, 22, 23, 24, 25, 26, 27, 28, 29, 30, 31, 32, 33, 34, 5, 7, 8, 35, 36, 37, 6, 38, 33, 39, 40, 41, 42, 43, 44, 45, and 46, respectively).

The term "substitution," as used herein, refers to one or more than one (one or multiple) nucleotide changes in the naturally occurring self-cleaving RNA motif. The term "self-cleaving schistosome RNA mutant motif" refers to a self-cleaving schistosome RNA motif, comprising at least one nucleotide alteration compared to a naturally occurring (wildtype) schistosome ribozyme (e.g., sml) as depicted in FIG. 1d (Ferbeyre et al., Mol. Cell Bio., 18:3880-3888 (1998)). Methods described herein can be used to identify any self-cleaving ribozyme mutant motifs (e.g., self-cleaving schistosome RNA mutant motifs with altered catalytic properties). Methods of assaying catalytic activity are well known in the art. For example, labeled self-cleaving schistosome RNA mutant motifs can be incubated under appropriate conditions for cleavage, fractionated by gel electrophoresis and the extent of cleavage quantitated by autoradiography. Methods of quantitating catalytic activity of the self-cleaving schistosome RNA mutant motifs of the invention are known in the art and include the use of a reporter gene, such as, for example, as described herein in Example 1.

Expression Vectors and Cell Lines

In certain embodiments, the present invention encompasses nucleic acids (e.g., DNA vectors) which encode a self-cleaving ribozyme (naturally occurring or mutants such as schistosome ribozyme mutants) and their use in modulating expression of a nucleic acid product. The present invention relates to methods of inserting the self-cleaving RNA mutant motif sequence into an endogenous gene in a cell, or into an exogenous gene to be introduced into a cell by a vector. In either case, necessary elements (e.g., promoters) are present for the transcription of the inserted sequence. For example, a self-cleaving ribozyme is inserted into an appropriate expression vector which contains the necessary elements for the transcription of the inserted sequence. The expression vector is then transfected into a host cell in order to effectuate expression of the ribozyme-encoding sequence and to determine its effect on gene function in the transfected cell and/or its progeny.

In one embodiment, the present invention relates to a nucleic acid (e.g., a DNA construct) which comprises a promoter, DNA encoding a nucleic acid product operably linked to the promoter, and DNA encoding a self-cleaving ribozyme (naturally occurring or mutants such as schistosome ribozyme mutants) which is downstream of the promoter. Transcription of the two DNA components in the construct produces a RNA molecule comprising the self-cleaving ribozyme and mRNA encoding the nucleic acid product, and the self-cleaving ribozyme can cleave the RNA intramolecularly.

In another embodiment, the present invention relates to a viral vector comprising a promoter, a nucleic acid encoding a nucleic acid product operably linked to the promoter and a nucleic acid encoding a self-cleaving ribozyme (naturally occurring or mutants such as schistosome ribozyme mutants) which is downstream of the promoter. Transcription of the two nucleic acid components in the viral vector produces a RNA molecule comprising a self-cleaving ribozyme and mRNA encoding the nucleic acid product, and the self-cleaving ribozyme can cleave the RNA intramolecularly. In another embodiment, the present invention relates to a virus comprising a promoter, a nucleotide sequence encoding a nucleic acid product operably linked to the promoter and a nucleotide sequence encoding a self-cleaving ribozyme which is downstream of the promoter. Transcription of the two nucleotide sequences in the virus produces a RNA molecule comprising a self-cleaving ribozyme and mRNA encoding the nucleic acid product, and the self-cleaving ribozyme can cleave RNA intramolecularly.

DNA constructs encoding a self-cleaving ribozyme (naturally occurring or mutants such as schistosome ribozyme mutants) of the present invention can be manufactured according to methods generally known in the art. For example, nucleic acids encoding a self-cleaving ribozyme can be manufactured by chemical synthesis or recombinant DNA/RNA technology (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)).

In certain embodiments, the present invention provides a kit for regulating gene expression. The subject kit comprises a nucleic acid comprising: (a) a self-cleaving ribozyme (naturally occurring or mutants such as schistosome ribozyme mutants); and (b) a cloning site for introduction of a target nucleotide sequence to be transcribed operatively linked to the self-cleaving ribozyme. Optionally, the kit may further comprise an inhibitor of the self-cleaving ribozyme. Transcription of the target nucleotide sequence is inhibited in the absence of the inhibitor, while transcription of the target nucleotide sequence is induced in the presence of the inhibitor. For example, a schistosome ribozyme mutant comprises a nucleotide sequence selected from SEQ ID NOs: 1-46. The inhibitor of the kit as described below includes, but is not limited to, toyocamycin, 8-azaadenosine, sangivamycin, tubercidin, tubercidin-cyclic monophosphate, tubercidin-monophosphate, tubercidin-triphosphate, nebularine, tricyclic nucleoside, 5-fluorouridine, 5-bromouridine, 5-fluorouracil, Syto-83, homidium bromide, and acridine orange.

Another aspect of the present invention relates to a method of modulating expression of a nucleic acid product comprising producing a nucleic acid encoding a self-cleaving ribozyme (naturally occurring or mutants such as schistosome ribozyme mutants), as described herein, and a nucleic acid product, wherein the self-cleaving ribozyme modulates expression of the nucleic acid product. The nucleic acid product can be a polypeptide, DNA or RNA other than self-cleaving RNA and can be expressed in cells as a component of a DNA construct. The nucleic acid product to be expressed can be a therapeutic protein.

It is desirable that the subject ribozyme (naturally occurring or mutants such as schistosome ribozyme mutants) sufficiently self cleaves such that the target nucleic acid product is not expressed. Such substantial self cleavage would facilitate the observation of the effect of depletion of gene function in the organism. While desirable, complete self cleavage of the ribozyme is not required by the methods of the invention, so long as the ribozyme results in a reduced level of a target nucleic acid product relative to a control. The term "reduced level of a target nucleic acid product relative to a control" refers to a quantity of a target nucleic acid product which is less than, preferably at least 20% less than, more preferably at least 50% less than, yet more preferably at least 90% less than the quantity of a target nucleic acid product in a control (e.g., a corresponding sample in the absence of the ribozyme, or in the presence of a ribozyme which is incapable of self-cleaving), and most preferably is at the background level of, or is undetectable by, Northern blot hybridization as described herein. The invention does not require, and is not limited to, methods in which a target nucleic acid product is 99% or 100% ablated.

In another embodiment, the present invention relates to a method of modulating expression of a nucleic acid product in a cell comprising introducing into a cell a DNA construct which comprises: (a) promoter, (b) a nucleic acid encoding a nucleic acid product which is operably linked to the promoter and (c) a nucleic acid encoding a self-cleaving ribozyme (naturally occurring or mutants such as schistosome ribozyme mutants) downstream of the promoter. Transcription of the nucleic acid components produces a RNA molecule (mRNA) comprising the self-cleaving ribozyme and mRNA encoding the nucleic acid product such that the self-cleaving ribozyme cleaves the RNA intramolecularly, thus modulating expression of the nucleic acid product.

If the DNA construct is present in cells under conditions which permit expression of the two nucleotide components, the mRNA molecule comprising the self-cleaving ribozyme and mRNA encoding the nucleic acid product is produced, the encoded self-cleaving ribozyme is spontaneously cleaved and, as a result, the nucleic acid product is not produced. On the other hand, if the DNA construct is present in cells in the presence of an agent, such as a drug (e.g., an antibiotic), which inhibits (totally or partially) cleaving activity of the encoded self-cleaving ribozyme, the desired nucleic acid product is produced.

The present invention also encompasses other structural elements that can affect the stability and/or the activity of the self-cleaving ribozyme (naturally occurring or mutants such as schistosome ribozyme mutants), either positively or negatively. For example, it has been determined that RNA sequences adjacent to the catalytic site of the self-cleaving ribozyme affect its cleaving activity. The cleaving activity of the self-cleaving ribozyme can be modulated by binding of an effector to an aptamer which is grafted onto the self-cleaving ribozyme at a location such that the cleaving activity can be controlled by binding of the effector to the aptamer.

Also the subject of the present invention is a DNA construct useful in the present method of controlling expression of a desired nucleic acid product in a cell. In one embodiment, the DNA construct comprises: (a) DNA encoding a nucleic acid product to be expressed in the cell; and (b) DNA encoding a self-cleaving ribozyme (naturally occurring or mutants such as schistosome ribozyme mutants). Transcription of the two DNA components in the construct yields an mRNA comprising the self-cleaving ribozyme and mRNA encoding the nucleic acid product to be expressed. The construct components can be separated by intervening DNA, such as a linker, provided that the intervening DNA does not interfere with the ability of the cleaving activity of the encoded self-cleaving ribozyme to disrupt (cleave) the mRNA coding for the desired nucleic acid product, thereby inhibiting/blocking expression of the desired nucleic acid product. This embodiment of the DNA construct can be introduced into appropriate recipient/host cells in such a manner that the construct integrates into host cell genomic DNA at a location which results in its being operably linked to a host cell promoter (DNA sufficient to initiate transcription) and, as a result, expressed under the control of the host cell machinery. If the host cell is maintained under conditions appropriate for expression of DNA in the host cell (including expression of the DNA of the introduced and now integrated DNA construct), the encoded desired nucleic acid product is not expressed because the self-cleaving ribozyme is produced and its activity results in disruption of the resulting transcript (mRNA), which cannot subsequently be translated. As a result, the encoded nucleic acid product is not expressed. If the host cell which contains the DNA construct of this embodiment is maintained under conditions appropriate for expression of DNA in the host cell and in the presence of an agent such as an antibiotic (which prevents activity of the encoded self-cleaving ribozyme), disruption of the resulting transcript does not occur and the encoded desired nucleic acid product is expressed. In this embodiment, in which the DNA construct integrates into host cell genomic DNA, the construct can comprise additional DNA which increases the extent to which the DNA construct integrates into host cell genomic DNA and/or targets or directs introduction of the construct to a specific genomic location. The construct of this embodiment can also include additional components, such as an enhancer and transcriptional binding sites.

In an alternative embodiment, the DNA construct further comprises DNA sufficient for initiation of transcription (such as a promoter) operably linked to the DNA encoding the desired nucleic acid product. In a particular embodiment, the DNA encoding the self-cleaving ribozyme (naturally occurring or mutants such as schistosome ribozyme mutants) is 5' of the DNA encoding the desired nucleic acid product. Thus, the order of the components in the construct (from 5' to 3') is: promoter—DNA encoding self-cleaving ribozyme—DNA encoding the desired nucleic acid product. In a second embodiment, the DNA encoding the self-cleaving ribozyme is 3' of the DNA encoding the desired nucleic acid product. Thus, the order of the components in the construct (from 5' to 3') is: promoter—DNA encoding the desired nucleic acid product—DNA encoding self-cleaving ribozyme.

In certain aspects, the DNA construct of the invention comprises a promoter which includes, but is not limited to, tRNA promoter, 5S rRNA promoters, histone gene promoters, CMV promoter, RSV promoter, SV40 promoter, PEPCK promoter, MT promoter, SRa promoter, P450 family promoters, GALT promoter, T7 promoter, T3 promoter, SP6 promoter, and K11 promoter. The T7 promoter, T3 promoter, SP6 promoter, and K11 promoter have been described in U.S. Pat. No. 5,591,601, the entire contents of which are incorporated by reference.

The invention relates to packaging cell lines useful for generating recombinant viral vectors and viruses comprising a recombinant genome which includes a nucleotide sequence (RNA or DNA) which represents a DNA construct of the present invention; construction of such cell lines; and methods of using the recombinant viral vectors to modulate production of a desired nucleic acid product in vitro, in vivo and ex vivo. In a particular embodiment, the recombinant viral vectors and viruses comprise a recombinant genome which includes a nucleotide sequence encoding a self-cleaving ribozyme (naturally occurring or mutants such as schistosome ribozyme mutants), a nucleotide sequence encoding a desired nucleic acid product and a promoter operably linked to the nucleotide sequence encoding the desired nucleic acid product, as described herein.

Cell lines useful for generating recombinant viral vectors and viruses comprising a recombinant genome which includes a nucleotide sequence which represents a DNA construct of the present invention are produced by transfecting host cells, such as mammalian host cells, with a viral vector including the DNA construct integrated into the genome of the virus, as described herein. Viral stocks are harvested according to methods generally known in the art. See, e.g., Ausubel et al., Eds., Current Protocols In Molecular Biology, John Wiley & Sons, New York (1998); Sambrook et al., Eds., Molecular Cloning: A Laboratory Manual, 2nd edition, Cold Spring Harbor University Press, New York (1989); Danos and Mulligan, U.S. Pat. No. 5,449,614; and Mulligan and Wilson, U.S. Pat. No. 5,460,959, the teachings of which are incorporated herein by reference. The recombinant viral vectors produced by the packaging cell lines of the present invention are also referred to herein as viral vectors which represent the DNA construct.

Methods of Delivering Nucleic Acids

DNA constructs encoding self-cleaving ribozyme (naturally occurring or mutants such as schistosome ribozyme mutants) can be introduced into a cell by a variety of methods (e.g., transformation, transfection, direct uptake, projectile bombardment, using liposomes). The present invention contemplates any methods generally known in the art which are appropriate for the particular agent or effector and cell type. For example, agents and effectors can be introduced into a cell by direct uptake, DEAE-dextran, calcium phosphate precipitation, lipofection, cell fusion, electroporation, biolistics, microinjection, infection (e.g., by DNA viruses and RNA viruses) and retrovirus-mediated transduction. Such methods are described in more detail, for example, in Sambrook et al., Molecular Cloning: A Laboratory Manual, Second Edition, Cold Spring Harbor University Press, New York (1989); and Ausubel, et al., Current Protocols in Molecular Biology, John Wiley & Sons, New York (1998). Other suitable methods are also described in the art.

A vector comprising a DNA construct can also be introduced into a cell by targeting the vector to cell membrane phospholipids. For example, targeting of a vector of the present invention can be accomplished by linking the vector molecule to a VSV-G protein, a viral protein with affinity for all cell membrane phospholipids. Such a construct can be produced using methods well known to those practiced in the art.

In a particular embodiment, a DNA construct encoding a self-cleaving ribozyme (naturally occurring or mutants such as schistosome ribozyme mutants) is inserted into a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

As a particular example of the above approach, a DNA construct of the invention can be integrated into the genome of a virus that enters the cell. By infection of the cell, the components of a system which permit expression of the DNA encoding the desired nucleic acid product and the spontaneous cleavage of the corresponding mRNA, are introduced into the cell. Under appropriate conditions, spontaneous cleavage of the corresponding mRNA occurs and expression of the encoded product is inhibited.

Virus stocks consisting of recombinant viral vectors comprising a recombinant genome which includes a nucleotide (DNA or RNA) sequence which represents a DNA construct of the present invention, are produced by maintaining the transfected cells under conditions suitable for virus production. Such conditions, which are not critical to the invention, are generally known in the art. See, e.g., Sambrook et al., Molecular Cloning: A Laboratory Manual, Second Edition, Cold Spring Harbor University Press, New York (1989); Ausubel et al., Current Protocols in Molecular Biology, John Wiley & Sons, New York (1998); U.S. Pat. No. 5,449,614; and U.S. Pat. No. 5,460,959, the teachings of which are incorporated herein by reference. The resulting recombinant viral vectors can be used, as described herein, to modulate production of a desired nucleic acid product in vitro, in vivo and ex vivo.

Thus, the invention also relates to recombinant viral vectors and viruses comprising a recombinant genome which includes a nucleotide (DNA or RNA) sequence which represents a DNA construct of the present invention. Viral vectors and viruses which comprise the DNA constructs or the encoded (reverse transcribed) RNA are also the subject of the present invention.

In certain embodiments, the present invention contemplates a method of inhibiting expression of a nucleic acid product in host cells, comprising introducing a self-cleaving ribozyme alone (naturally occurring or mutants such as schistosome ribozyme mutants) into cells. Cells comprising the RNA mutant motif are cultured under conditions appropriate for the RNA mutant motif to pair with and cleave the mRNA encoding the nucleic acid product. The self-cleaving ribozyme sequence can be produced by chemical synthetic methods or by recombinant nucleic acid techniques. For example, cloned RNA polymerase can be used for transcription in vitro. The produced self-cleaving ribozyme sequence may be made to include modifications to either the phosphate-sugar backbone or the nucleoside, e.g., to reduce susceptibility to cellular nucleases, improve bioavailability, improve formulation characteristics, and/or change other pharmacokinetic properties. The self-cleaving ribozyme sequence may be produced enzymatically or by partial/total organic synthesis, any modified ribonucleotide can be introduced by in vitro enzymatic or organic synthesis. The self-cleaving ribozyme sequence can then be introduced into cells by the conventional methods described above which are routinely used to deliver nucleic acids.

Methods of Identifying Ribozyme Regulators

The present invention relates to a method of screening for an agent which is capable of inhibiting the catalytic activity of a self-cleaving ribozyme (naturally occurring or mutants such as schistosome ribozyme mutants). In one embodiment of this method, host cells are introduced a DNA construct which comprises: (1) DNA encoding a reporter, (2) a promoter operably linked to the DNA encoding the reporter, and (3) DNA encoding a self-cleaving ribozyme, wherein the DNA of (1) and the DNA of (3) are downstream of the promoter, and transcription of the DNA of (1) and the DNA of (2) yields a mRNA comprising the self-cleaving ribozyme and mRNA encoding the reporter. Host cells are contacted with an agent to be assessed for its ability to inhibit the catalytic activity of the self-cleaving ribozyme under conditions appropriate for expression of the reporter, and reporter activity is assayed in the host cells. If reporter activity is detected, the mRNA coding for the reporter is not cleaved, indicating that the catalytic activity of the self-cleaving ribozyme is inhibited by the agent.

The term "reporter" refers to a protein or polypeptide whose activity can be readily and easily assayed using standard techniques. Examples of reporters include enzymes, such as β-galactosidase, β-glucoronidase, β-glucosidase, bacterial chloramphenicol acetyl transferase (CAT), luminescent molecules, such as green flourescent protein and firefly luciferase, and auxotrophic markers such as His3p and Ura3p. See, e.g., Ausubel, F. M. et al., Current Protocols in Molecular Biology, Chapter 9, John Wiley & Sons, Inc. (1998).

The present invention also relates to a method of screening for an effector which binds to a desired aptamer (or RNA sequence). In one embodiment of this method, host cells are introduced a DNA construct representing the DNA construct, wherein the DNA construct comprises: (1) DNA encoding a reporter, (2) a promoter operably linked to the DNA encoding the reporter and (3) DNA encoding a self-cleaving ribozyme which comprises a desired aptamer (or RNA sequence) grafted at a position such that the cleaving activity of the self-cleaving ribozyme is regulatable by the binding of an effector to the aptamer (or RNA sequence), wherein the DNA of (1) and the DNA of (3) are downstream of the promoter, and transcription of the DNA of (1) and the DNA of (3) produces a mRNA comprising the aptamer-self-cleaving ribozyme (or RNA sequence-self-cleaving ribozyme) and mRNA encoding the reporter. Host cells are contacted with an agent to be assessed for its ability to bind the aptamer (or RNA sequence) under conditions appropriate for expression of the reporter, and reporter activity is assayed in the host cells. If the agent binds to the aptamer (or RNA sequence), the cleaving activity of the self-cleaving RNA motif is inhibited and, as a result, the mRNA coding for the reporter is not cleaved and the reporter is produced. Therefore, if reporter activity is detected, the agent is identified as an effector which binds to the desired aptamer (or RNA sequence).

The invention also relates to a method of screening for an agent which is capable of inhibiting the catalytic activity of a self-cleaving ribozyme (naturally occurring or mutants such as schistosome ribozyme mutants) including a random sequence at a position in the self-cleaving ribozyme capable of modulating the cleaving activity of the self-cleaving ribozyme comprising: (a) introducing into host cells a DNA construct which represents the DNA construct, wherein the DNA construct comprises: (1) a promoter; (2) DNA encoding a reporter operably linked to the promoter; and (3) DNA encoding a self-cleaving ribozyme modified to include a random sequence at a position in the self-cleaving ribozyme capable of modulating the cleaving activity of the self-cleaving schistosome RNA mutant motif, wherein the DNA of (2) and the DNA of (3) are downstream of the promoter, and transcription of the DNA of (2) and the DNA of (3) yields a mRNA comprising the self-cleaving ribozyme including the random sequence and mRNA encoding the reporter; (b) contacting the host cells with an agent to be assessed for its ability to inhibit the catalytic activity of the self-cleaving ribozyme including the random sequence under conditions appropriate for expression of the reporter; and (c) assaying reporter activity in the host cells. If reporter activity is detected, the mRNA coding for the reporter is not cleaved, indicating that the catalytic activity of the self-cleaving ribozyme including the random sequence is inhibited by the agent.

Agents, such as drugs, chemical compounds, ionic compounds, organic compounds, organic ligands, including cofactors, saccharides, recombinant and synthetic peptides, proteins, peptoids, and other molecules and compositions, can be individually screened or one or more agents can be tested simultaneously for the ability to modulate the cleaving activity of a self-cleaving ribozyme or for the ability to bind to a aptamer moiety in accordance with the methods described herein. Where a mixture of agents is tested, the agents selected by the methods described can be separated and identified by suitable methods (e.g., PCR, sequencing, chromatography). One or more agents in a test sample which modulate the cleaving activity of a self-cleaving ribozyme can be determined according to these methods. Similarly, agents in a test sample which bind an aptamer moiety can also be determined.

Large combinatorial libraries of agents (e.g., organic compounds, recombinant or synthetic peptides, peptoids, nucleic acids) produced by combinatorial chemical synthesis or other methods can be tested (see e.g., Zuckerman, R. N. et al., J. Med. Chem., 37:2678-2685 (1994) and references cited therein; see also, Ohlmeyer, M. H. J. et al., Proc. Natl. Acad. Sci. USA 90:10922-10926 (1993) and DeWitt, S. H. et al., Proc. Natl. Acad. Sci. USA 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). The teachings of these references are incorporated herein by reference. Where agents selected from a combinatorial library carry unique tags, identification of individual agents by chromatographic methods is possible. In addition, chemical libraries, microbial broths and phage display libraries can be tested (screened) in accordance with the methods herein.

In a further embodiment, the cleaving activity of a self cleaving ribozyme (naturally occurring or mutants such as schistosome ribozyme mutants) can be inhibited (partially or totally) using an agent such as a drug (e.g., an antibiotic) or other molecule or composition, which inhibits (partially or totally) the cleaving activity of the self-cleaving ribozyme. Inhibition of spontaneous cleavage of the corresponding mRNA results in the efficient induction of expression of the nucleic acid product of interest. Antibiotics that can be used to inhibit the cleaving activity of a self cleaving ribozyme include aminoglycoside antibiotics, such as, but not limited to, neomycin B, neomycin sulfate, adriamycin RDF, doxorubicin, Bisbenzimide, chelocardin, diminazene aceturate, ribostamycin, paromomycin, neamine, gentamicin, gentamicin C complex, gentamicin CIA sulfate, gentamicin sulfate, gramicidin S HCL, lincomycin, kanamycin, tobramycin, tuberactinomycin A, tuberactinomycin B, 6'-amino-6'-deoxykanamycin and 5'-epi-sisomicin; tetracyclines and their derivatives and analogs, such as, but not limited to, tetracycline, chlortetracycline, demeclocycline, chelocardin and 4-epi-anhydrochlortetracycline; peptide antibiotics, such as, but not limited to, viomycin, di-β-lysyl capreomycin IIA and tuberactinomycin A; and pseudodisaccharide antibiotics, such as, but not limited to, 2'-de-N-β-lysyllysinomicin, 3-epi-6'-de-C-methylfortimicin B and 3-epi-2'-N-1-β-lysyl-6'-de-C-methylfortimicin B. Other antibiotics that can be used to inhibit the cleaving activity of a self cleaving ribozyme are known and described in the art. See, for example, Stage et al., RNA, 1:95-101 (1995); Clouet-d'Orval et al., Biochem., 34:11186-11190 (1995); Murray and Arnold, Biochem. J., 317:855-860 (1996); Hermann and Westhof, J. Mol. Biol., 276:903-912 (1998); and Rogers et al., J. Mol. Biol., 259:916-925 (1996), the teachings of which are entirely incorporated herein by reference.

In certain specific embodiments, inhibitors of a self cleaving ribozyme (naturally occurring or mutants such as schistosome ribozyme mutants) include, but are not limited to, antisense oligonucleotides of the ribozyme and any modified form of the antisense oligonucleotides. For example, an antisense oligonucleotide bases pair with a region of the self-cleaving schistosome RNA mutant motif as depicted in FIG. 1e. As a result, activity of the self-cleaving ribozyme is inhibited (partially or totally) by the antisense oligonucleotide. In certain cases, the antisense oligonucleotide is a modified oligonucleotide selected from the group consisting of: morpholino, phosphorothioate RNA, 2'-O-methyl RNA, and phosphorothioate 2'-O-methoxyethyl RNA.

In other specific embodiments, inhibitors of a self cleaving ribozyme (naturally occurring or mutants such as schistosome ribozyme mutants) include, but are not limited to, the compounds listed in Table 2, such as toyocamycin, 5-fluorouridine, and 5-fluorouracil.

In certain embodiments, the present invention contemplates a method for determining the level of an inhibitor of a ribozyme (naturally occurring or mutants such as schistosome ribozyme mutants) in a biological sample. The term "determining" is used herein to refer to any process of observing an inhibitor in a biological sample, whether or not the inhibitor is actually detected. Determining the level of an inhibitor may be a quantitative, semi-quantitative or non-quantitative observation. Such methods can be used for determining an inhibitor which is present in a cell or in a biological sample. Exemplary inhibitors include 5-fluorouracil and 5-fluorouridine. As used herein, the 5-FU compounds include 5-fluorouracil and its metabolite derivatives such as 5-fluorouridine.

5-fluorouracil is widely used in the treatment of a large range of tumors and according to various schedules. Some studies have proved a relationship between 5-fluorouracil plasma concentrations and the toxic and therapeutic effects of the treatment in different types of tumors (Beerblock, et al., 1997, Cancer 79: 1100; Trump, et al., 1991, J. Clin. Oncol. 11: 2027; Gamelin, et al., 1996, Cancer 77:441; Gamelin, et al., 1998, J. Clin. Oncol. 16:1470; Milano, et al., 1994, J. Clin. Oncol. 12:1291). These findings were the basis for the determination of a therapeutic range for the 5-FU compound, which is essential for individual adjustment the dosage of compound. For example, by means of individual dosage based on 5-FU concentrations, Gamelin et al. reached a percentage of objective responses of 56% Gamelin, et al., 1998, J. Clin. Oncol. 16:1470), while this value was approximately 15% for 5-FU in monotherapy.

In one specific embodiment, the invention provides a method for determining the level of 5-FU compound in a cell, comprising:

(a) introducing into a cell a DNA construct which comprises: (1) a promoter; (2) nucleic acid encoding a reporter; and (3) nucleic acid encoding a ribozyme (naturally occurring or mutants such as schistosome ribozyme mutants), wherein the nucleic acid of (2) and the nucleic acid of (3) are downstream of the promoter and operably linked to said promoter, under conditions which result in inhibition of the ribozyme and expression of the reporter; and (b) assaying reporter activity in the cell produced by (a), wherein the level of said 5-FU compound in the cell is identified by comparing the reporter activity with an appropriate control.

In another specific embodiment, the invention provides a method for determining the level of a 5-FU compound in a biological sample comprises:

(a) contacting a cell with a biological sample, wherein the cell expresses a DNA construct which comprises: (1) a promoter; (2) a nucleic acid encoding a reporter; and (3) a nucleic acid encoding a ribozyme (naturally occurring or mutants such as schistosome ribozyme mutants), wherein the nucleic acid of (2) and the nucleic acid of (3) are downstream of the promoter and operably linked to said promoter, under conditions which result in inhibition of the ribozyme and expression of the reporter; and (b) assaying the reporter activity in the presence of the biological sample, wherein the level of the 5-FU compound in the biological sample is identified by comparing the reporter activity with an appropriate control.

As described in the working examples, Applicants have found that 5-FU compounds inhibited activity of a ribozyme (e.g., a self-cleaving schistosome ribozyme mutant) in a dose-dependent manner. In certain cases, an appropriate control of the method may be a reference panel including predetermined mean values which have been developed by contacting the cell with various doses of a 5-FU compound. Exemplary biological samples of the method include, but are not limited to, living cells or tissues (in vivo or in vitro), lysates or extracts of cells or tissues, and bodily fluids (e.g., blood, serum, plasma, a blood-derived fraction, stool, colonic effluent or urine).

In other embodiments, the present invention provides methods of inhibiting activity of a catalytic RNA (e.g., a ribozyme or mutants thereof) in a cell and methods of inhibiting infection by a virus or a pathogenic microorganism in a cell. Traditionally, pharmaceutical discovery has been focused on the compounds that target the protein products of genes, while RNAs as drug targets have remained largely unexplored. Recently, interests in RNAs are increasing (Zaman G J R 2003; Hermann T, 1998; Pearson N D, 1997). There have been efforts to target catalytic RNAs in viruses and pathogenic microorganisms with small molecules (Rogers J, 1996, supra). In the methods of the present invention, cells which have been infected or are at risk of having infection by a virus or a pathogenic microorganism (e.g., a parasite) are contacted with any of the inhibitors as described above (e.g., Table 2). These inhibitors interfere with RNA catalytic activity preferably through RNA incorporation and can be used to target any RNA catalytic activities involved in function (e.g., genome replication) of the viruses or pathogenic microorganisms.

In certain aspects, viruses of the methods include, but are not limited to, hepatitis virus (e.g., C, B, and delta), human immunodeficiency virus (HIV), herpes virus, and human papillomavirus (HPV). In other aspects, pathogenic microorganisms of the methods include, but are not limited to, *Notophthalmus viddescens*, *Ambystoma talpoideum*, *Amphiuma tridactylum*, and *Schistosoma mansoni*. Cells of the methods can be animal cells (e.g., mammalian cells such as human cells) or plant cells (e.g., tobacco).

Methods of Treatment and Administration

In certain embodiments, agents and effectors of the present invention can be introduced into a cell for therapeutic applications. As used herein, a cell includes, but is not limited to, a prokaryotic cell, such as a bacterial cell, and eukaryotic cell, such as an animal, plant or yeast cell. A cell which is of animal or plant origin can be a stem cell or somatic cell. Suitable animal cells can be of, for example, mammalian or avian origin. Examples of mammalian cells include human (such as HeLa cells), bovine, ovine, porcine, murine (such as embryonic stem cells), rabbit and monkey (such as COSI cells) cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The cells can be obtained commercially or from a depository or obtained directly from an individual, such as by biopsy. The cells used can be obtained from an individual to whom they will be returned or from another/different individual of the same or different species. For example, non-human cells, such as pig cells, can be modified to include a DNA construct and then introduced into a human. Alternatively, the cell need not be isolated from the individual where, for example, it is desirable to deliver the vector to the individual in gene therapy.

For example, the present invention relates to a method of regulating expression of an endogenous gene (a gene resident in a cell as the cell was obtained) to produce a desired nucleic acid product and compositions useful in the method. The endogenous gene can be one which is expressed ("on") in the cell or one which is normally not expressed ("off") in the cell but whose expression is or has been turned on or activated. DNA encoding a self-cleaving ribozyme (naturally occurring or mutants such as schistosome ribozyme mutants), or a virus or viral vector comprising a recombinant genome which includes a nucleotide (RNA or DNA) sequence which represents DNA encoding a self-cleaving ribozyme, can be introduced into genomic DNA of cells in such a position that in mRNA produced by the cells, the self-cleaving ribozyme is in a location which results in control of expression of the encoded product. In the absence of an agent which inhibits expression of the self-cleaving ribozyme, cleavage occurs and the desired nucleic acid product is not expressed. In the presence of such an agent, cleaving activity is inhibited and the desired nucleic acid product is expressed. In one embodiment, DNA encoding a self-cleaving ribozyme, or a virus or viral vector comprising a recombinant genome which includes a nucleotide (RNA or DNA) sequence which represents DNA encoding a self-cleaving ribozyme, is introduced into genomic DNA between the promoter operably linked to (controlling expression of) the endogenous gene encoding the desired nucleic acid product, in such a manner that the endogenous gene remains operably linked to the promoter. In an alternative embodiment, the DNA encoding a self-cleaving ribozyme, or the virus or viral vector, is introduced into genomic DNA 3' of the endogenous gene encoding the desired nucleic acid product. The promoter which is operably linked to the endogenous gene to be expressed can be the naturally occurring (endogenous) promoter for the gene or can be an exogenous promoter introduced into genomic DNA. The resulting cells can be used, as described herein, to modulate production of the desired nucleic acid product in an individual.

The present invention also relates to cells (host cells) which comprise a DNA construct of the invention. Particular cells which comprise a DNA construct of the invention are discussed above.

In a particular embodiment, a ribozyme (naturally occurring or mutants such as schistosome ribozyme mutants) of the invention and DNA construct encoding the ribozyme can be used to produce transgenic animals whose cells contain and express the ribozyme. There is a variety of techniques for producing transgenic animals of the present invention. For example, foreign nucleic acid can be introduced into the germline of an animal by, for example, introducing the additional foreign genetic material into a gamete, such as an egg. Alternatively, transgenic animals can be produced by breeding animals which transfer the foreign DNA to their progeny. It is also possible to produce transgenic animals by introducing foreign DNA into somatic cells from which an animal is produced. As used herein, the term "transgenic animal" includes animals produced from cells modified to contain foreign DNA or by breeding; that is, it includes the progeny of animals (ancestors) which were produced from such modified cells. As used herein, the term "foreign nucleic acid" refers to genetic material obtained from a source other than the parental germplasm. Preferably, the transgenic animals are derived from mammalian embryos.

In certain aspects, the invention provides a homologous recombinant non-human animal expressing the ribozyme (naturally occurring or mutants such as schistosome ribozyme mutants). The term "homologous recombinant animal" as used herein is intended to describe an animal containing a gene which has been modified by homologous recombination between the gene and a DNA molecule introduced into a cell of the animal, e.g., an embryonic cell of the animal. An animal can be created in which nucleic acid encoding the ribozyme has been introduced into a specific site of the genome.

To create such a homologous recombinant animal, a vector is prepared which contains DNA encoding the ribozyme flanked at its 5' and 3' ends by additional nucleic acid of a eukaryotic gene at which homologous recombination is to occur. The additional nucleic acid flanking that encoding the ribozyme is of sufficient length for successful homologous recombination with the eukaryotic gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) Cell 69:915).

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) Nucl. Acids Res. 21:2025-2029; and Fukushige, S. and Sauer, B. (1992) Proc. Natl. Acad. Sci. USA 89:7905-7909) and the FLP recombinase-FRT target system (e.g., as described in Dang, D. T. and Perrimon, N. (1992) Dev. Genet. 13:367-375; and Fiering, S. et al. (1993) Proc. Natl. Acad. Sci. USA 90:8469-8473).

Methods for acquiring, culturing, maintaining and introducing foreign nucleic acid sequences into recipient eggs for transgenic animal production are well known in the art. See, for example, Manipulating the Mouse Embryo: A Laboratory Manual, Hogan et al., Cold Spring Harbor Laboratory, New York (1986). Preferably, a DNA construct will be delivered into the embryo at a very early stage in development so that only a small frequency of the embryos are mosaic (e.g., an embryo in which integration of the foreign nucleic acid occurs after the one cell stage of development).

The DNA constructs of the present invention can be used in methods of inducing expression of a desired nucleic acid product in an individual (e.g., a human or other mammal or vertebrate). In these methods, a DNA construct of the present invention can be introduced into cells obtained from the individual. The cells can be migratory, such as a hematopoietic cell, or non-migratory, such as a solid tumor cell or fibroblast. After treatment in this manner, the resulting cells can be administered to (introduced into) the individual according to methods known to those practiced in the art. To induce expression of the nucleic acid product, an agent (such as a drug) which is capable of inhibiting cleavage of the encoded self-cleaving ribozyme (naturally occurring or mutants such as schistosome ribozyme mutants), can be administered to the individual according to methods known to those practiced in the art. Such a treating procedure is sometimes referred to as ex vivo treatment. Ex vivo therapy has been described, for example, in Kasid et al., Proc. Natl. Acad. Sci. USA, 87:473 (1990); Rosenberg et al., N. Engl. J. Med., 323:570 (1990); Williams et al., Nature, 310:476 (1984); Dick et al., Cell, 42:71 (1985); Keller et al., Nature, 318:149 (1985); and Anderson et al., U.S. Pat. No. 5,399,346.

In a particular embodiment, the DNA constructs of the present invention can be used in a method of expressing a desired nucleic acid product in an individual. In this method, cells which comprise a DNA construct of the present invention are introduced into an individual. An agent (such as a drug) which is capable of inhibiting cleavage of the encoded self-cleaving ribozyme (naturally occurring or mutants such as schistosome ribozyme mutants), is then administered to the individual, in whom the DNA encoding the desired nucleic acid product is expressed, resulting in production of the product. In a particular embodiment of this method, the DNA construct which comprises: (a) DNA encoding the desired nucleic acid product; (b) a promoter operably linked to the DNA encoding the desired nucleic acid product; and (c) DNA encoding a self-cleaving ribozyme. The DNA encoding the desired nucleic acid product and the DNA encoding the self-cleaving ribozyme are downstream of the promoter. The DNA encoding the self-cleaving ribozyme can be 5' or 3' of the DNA encoding the desired nucleic acid product. Transcription of the two DNA components in the construct produces a mRNA comprising the self-cleaving ribozyme and mRNA encoding the desired nucleic acid product.

Alternatively, in a method for expressing a desired nucleic acid product in an individual, a DNA construct of the present invention can be administered directly to the individual. The mode of administration is preferably at the location of the target cells. The administration can be nasally or by injection. Other modes of administration (parenteral, mucosal, systemic, implant, intraperitoneal, oral, intradermal, transdermal, intramuscular, intravenous including infusion and/or bolus injection, subcutaneous, topical, epidural, buccal, rectal, vaginal, etc.) are generally known in the art. The DNA construct can, preferably, be administered in a pharmaceutically acceptable carrier, such as saline, sterile water, Ringer's solution, or isotonic sodium chloride solution. An agent (such as a drug) which is capable of inhibiting cleavage of the encoded self-cleaving ribozyme (naturally occurring or mutants such as schistosome ribozyme mutants), is then administered to the individual, in whom the DNA encoding the desired nucleic acid product is expressed, resulting in production of the product.

In another embodiment, the DNA constructs of the present invention can be used in a method of modulating expression of a desired nucleic acid product in an individual. In this method, cells which comprise a DNA construct of the present invention are introduced into an individual. An effector which is capable of binding to the aptamer moiety of the aptamer-self-cleaving ribozyme complex is then administered to the individual, whereupon expression of the DNA encoding the desired nucleic acid product can be induced, enhanced, reduced, inhibited or regulated, depending upon the design of the complex as discussed above. In a particular embodiment of this method, the DNA construct which comprises: (a) DNA encoding the desired nucleic acid product; (b) a promoter operably linked to the DNA encoding the desired nucleic acid product; and (c) DNA encoding an aptamer-self-cleaving-ribozyme complex (e.g., a self-cleaving schistosome RNA mutant motif which comprises an aptamer grafted onto to the self-cleaving schistosome RNA mutant motif at a location such that the cleaving activity of the self-cleaving schistosome RNA mutant motif can be controlled by binding of an effector to the aptamer). Alternatively, in a method for modulating expression of a desired nucleic acid product in an individual, a DNA construct of the present invention can be administered directly to the individual. The modes of administration include those described above. The DNA construct can, preferably, be administered in a pharmaceutically acceptable carrier, such as saline, sterile water, Ringer's solution, or isotonic sodium chloride solution. An effector which is capable of binding to the aptamer moiety of the aptamer-self-cleaving-ribozyme complex can then be administered to the individual, whereupon expression of the DNA encoding the desired nucleic acid product can be induced, enhanced, reduced, inhibited or regulated, depending upon the design of the complex as discussed above.

Agents and effectors can be administered to an individual in a variety of ways. The route of administration depends upon the particular agent or effector. Routes of administration are generally known in the art and include oral, intradermal, transdermal (e.g., in slow release polymers), intramuscular, intraperitoneal, intravenous including infusion and/or bolus injection, subcutaneous, topical, epidural, buccal, rectal, vaginal and intranasal routes. Other suitable routes of administration can also be used, for example, to achieve absorption through epithelial or mucocutaneous linings.

The dosage of agent, effector, DNA construct of the present invention administered to an individual, including frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired.

Pharmaceutical Compositions

In certain embodiments, the agent, effector, and DNA construct (collectively referred to herein as therapeutic agents) of the present disclosure are formulated with a pharmaceutically acceptable carrier. Such therapeutic agents can be administered alone or as a component of a pharmaceutical formulation (composition). Recombinant nucleic acid sequences (e.g., expression constructs) encoding a ribozyme (naturally occurring or mutants such as schistosome ribozyme mutants) can be used in therapeutic (or pharmaceutical) compositions for regulating expression of a target nucleic acid product. The therapeutic compositions of the invention can be used alone or in admixture, or in chemical combination, with one or more materials, including other recombinant vectors, materials that increase the biological stability of the recombinant vectors, or materials that increase the ability of the therapeutic compositions to specifically penetrate the relevant cell type. The therapeutic compositions of the invention are administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in Remington's Pharmaceutical Sciences, a standard reference text in this field.

The therapeutic compositions of the invention are administered in dosages determined to be appropriate by one skilled in the art. An appropriate dosage is one that effects a desired result, e.g., a reduction in a symptom of a disease sought to be treated. It is expected that the dosages will vary, depending upon the pharmacokinetic and pharmacodynamic characteristics of the particular agent, and its mode and route of administration, as well as the age, weight, and health of the recipient; the nature and extent of any relevant disease;

the frequency and duration of the treatment; the type of, if any, concurrent therapy; and the desired effect.

The therapeutic compositions of the invention can be administered to a patient by any appropriate mode, e.g., parenterally, intraperitoneally, orally, topically (e.g., with dimethyl sulfoxide), or intravenously, as determined by one skilled in the art. Alternatively, it may by necessary to administer the compositions surgically to the target tissue. The treatments of the invention can be repeated as needed, as determined by one skilled in the art.

Any method that accomplishes in vivo transfer of nucleic acids into eukaryotic cells can be used. For example, expression constructs thereof can be packaged into liposomes, non-viral nucleic acid-based vectors, erythrocyte ghosts, or microspheres (e.g., microparticles; see, e.g., U.S. Pat. Nos. 4,789,734; and 4,925,673; 3,625,214; and Gregoriadis, Drug Carriers in Biology and Medicine, pp. 287-341 (Academic Press, 1979)). Further, delivery of expression constructs encoding a ribozyme mutant motif can be accomplished by direct injection into target tissues, for example, in a calcium phosphate precipitate or coupled with lipids.

Exogenously provided ribozyme (naturally occurring or mutants such as schistosome ribozyme mutants) can contain modified nucleotides, e.g., modified nucleotides that enhance stability. For example, the ribozyme mutant motifs can contain inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., Chem. Rev. 90(4):544-584, 1990; Tidd et al., Anticancer Research 10:1169, 1990). Ribozymes' stability can also be increased by incorporating 3'-deoxythymidine or 2'-substituted nucleotides (substituted with, e.g., alkyl groups) into the ribozymes during synthesis, by providing the ribozymes as phenylisourea derivatives, or by having other molecules, such as aminoacridine or poly-lysine, linked to the 3' ends of the snoRNAs (see, e.g., Tidd et al, Anticancer Research 10:1169-1182, 1990). Modifications of the RNA nucleotides of the ribozyme motifs of the invention may be present throughout the ribozymes, or in selected regions. The DNA vectors encoding ribozyme motifs can be modified to increase their ability to penetrate the target tissue by, e.g., coupling them to lipophilic compounds. In addition, DNA vectors can be targeted to particular cells by coupling them to ligands specific for receptors on the cell surface of a target cell. DNA vectors can also be targeted to specific cell types by being conjugated to monoclonal antibodies that specifically bind to cell-type-specific receptors.

For topical administration, a therapeutically effective amount of one or more of the therapeutic agents is applied to the desired site on the skin, preferably in combination with a pharmaceutically acceptable carrier, e.g., a spreadable cream, gel, lotion, or ointment, or a liquid such as saline. For use on the skin, the penetration of the nucleic acids into the tissue may be accomplished by a variety of methods known to those of ordinary skill in this field. For example, the expression constructs may be incorporated into a transdermal patch that is applied to the skin. Preferably, the penetration-resulting from these methods is enhanced with a chemical transdermal delivery agent such as dimethyl sulfoxide (DMSO) or the nonionic surfactant, n-decylmethyl sulfoxide (NDMS), as described in Choi et al., Pharmaceutical Res., 7(11):1099, 1990. Dosages for a therapeutically effective amount for topical application would be in the range of 100 ng to 10 mg per treated surface area per day.

EXEMPLIFICATION

The invention now being generally described, it will be more readily understood by reference to the following examples, which are included merely for purposes of illustration of certain embodiments and embodiments of the present invention, and are not intended to limit the invention.

Recent studies of the control of specific metabolic pathways in bacteria have documented the existence of entirely 'RNA-based' mechanisms for controlling gene expression which involve the modulation of translation, transcription termination, or RNA self-cleavage through the direct interaction of specific intracellular metabolites and RNA sequences (Winkler, et al., 2002, Nature 419, 952-6; Winkler, et al., 2004, Nature 428, 281-6; Mandal, et al., 2004, Nat Struct Mol Biol 11, 29-35; Cech, et al., 2004, Nature 428, 263-4). Here, Applicants show that an analogous 'RNA-based" gene regulation system can effectively be 'designed' for mammalian cells via the incorporation of sequences encoding self-cleaving RNA motifs (Cech, et al., 1990, Biosci Rep 10, 239-61) into the transcriptional unit of a gene or vector. When properly positioned, the sequences lead to potent inhibition of gene or vector expression, due to the spontaneous cleavage of the RNA transcript. Administration of either oligonucleotides complementary to regions of the self-cleaving motif, or a specific small molecule results in the efficient induction of gene expression, due to inhibition of self-cleavage of the mRNA. Efficient regulation of transgene expression is shown to be possible in a variety of mammalian cell lines, and in live animals. In conjunction with other emerging technologies (Silverman, et al., 2003, RNA 9, 377-83), the general methodology may be particularly applicable to the development of gene regulation systems tailored to any small inducer molecule, and provide for a novel means of biological sensing in vivo that may have an important application in the regulated delivery of protein therapeutics.

The general strategy for controlling gene expression via modulation of RNA processing is shown in FIG. 1a. The approach is critically dependent upon both the ability of a specific self-cleaving ribozyme (rz) to effect the highly efficient cleavage (>99%) of an mRNA molecule into which it is embedded, and the availability of a small molecule capable of efficiently inhibiting self-cleavage of the cis-acting rz within an intracellular milieu. A first step in our studies was to identify candidate rz sequences capable of efficient cleavage in mammalian cells in the context of an 'expression' vector. For this purpose, Applicantsmade use of a transient transfection assay involving a standard mammalian expression vector (Ory, et al., 1996, Proc Natl Acad Sci USA 93, 11400-6) which encodes a LacZ reporter (FIG. 1b). Candidate rz sequences were introduced into one of a number of different locations within the vector transcriptional unit, and in parallel, the corresponding inactive mutant rzs were introduced into the same sites to provide a means of measuring the efficiency of reduction of reporter gene expression. After transfection of 293 cells with these vectors, protein extracts were prepared from cells and the β-gal level quantified. Cleavage activity of the functional rz in cells was measured as 'fold' suppression in reporter gene expression relative to the vector with inactive rz.

A large number of different rz encoding motifs were chosen for analysis, including unmanipulated natural rz sequences, rzs shown to function in mammalian cells, and rzs engineered by others to possess specific biochemical or catalytic properties in vitro (e.g., high Kcat, low Mg++ requirement, etc.). See Table 1 below. While the vast majority of rzs tested did not appreciably affect reporter expression, as reflected by near equal expression of Lacz by vectors encoding functional and inactive rzs (defined as 'fold'=1), two rz motifs were identified which did appear to function effectively: the hammerhead Pst-3 rz derived from the *Dolichopoda* cave cricket (Rojas, et al., 2000, Nucleic Acids Res 28, 4037-43) (FIG. 1e; 13-fold difference between functional and inactive rz) and the hammerhead Sml rz derived from the trematode *Schistosoma mansoni* (Ferbeyre, et al., 1998, Mol Cell Biol 18, 3880-8) (FIG. 1d) in which the tetraloop 5'UUCG3' was grafted onto an extended stem III (19-fold difference). Interestingly, both rzs possess unique structures relative to the other hammerhead rzs tested, in that they contain an extended 'stem-I' with an internal loop (see FIGS. 1c and 1d).

TABLE 1

Survey of ability of different ribozymes to function in mammalian cells.

| Ribozyme | Fold | Commands |
|---|---|---|
| Zillmen's hammerhead [1] | 1 | short stem II, worked at low Mg++ |
| Lockett's hammerhead [2] | 1 | short stem II, worked at low Mg++ |
| Szostak's hammerhead [3] | 1 | short stem II, higher catalytic rate |
| Taira's hammerhead [4] | 1 | worked in cells |
| Taira's embedded in tRNA [4] | 1 | tRNA helped to stablize the ribozyme |
| McSwiggen's hammerhead [5] | 1 | worked in cells |
| Uhlenbeck's hammerhead [6] | 1 | short stem I, higher catalytic rate |
| ABSV hammerhead [7] | 1 | Naturally occurring ribozyme |
| TRSV hairpin [8] | 1 | Naturally occurring ribozyme |
| TRSV hammerhead [8] | 1 | Naturally occurring ribozyme |
| Neurospora ribozyme [9] | 1 | Naturally occurring ribozyme |
| Hepatitis Delta Virus ribozyme [10] | 1 | Naturally occurring ribozyme |
| Newt hammerhead [11] | 1 | Naturally occurring ribozyme |
| Cricket hammerhead [12] | 13 | Naturally occurring ribozyme |
| Schisto hammerhead [13] | 1 | Naturally occurring ribozyme |
| Schisto with new loop-III | 19 | Naturally occurring ribozyme |

The above ribozymes can be found in the following references: 1) Zillmann, et al., RNA 3, 734-47 (1997); 2) Conaty, et al., Nucleic Acids Res 27, 2400-7 (1999); 3) Salehi-Ashtiani, et al., Nature 414, 82-4 (2001); 4) Yuyama, et al., Nucleic Acids Res 22, 5060-7 1994); 5) Chowrira, et al., J Biol Chem 269, 25856-64 (1994); 6) Clouet-d'Orval, et al., Biochemistry 36, 9087-92 (1997); 7) Hutchins, et al., Nucleic Acids Res 14, 3627-40 (1986); 8) Buzayan, et al., Virology 151, 186-199 (1986); 9) Rastogi, et al., Embo J 15, 2820-5 (1996); 10) Been, et al., Eur J Biochem 247, 741-53 (1997); 11) Zhang, et al., Gene 172, 183-90 (1996); 12) Rojas, et al., Nucleic Acids Res 28, 4037-43 (2000); 13) Ferbeyre, et al., Mol Cell Biol 18, 3880-8 (1998).

Based on its apparent higher level of self-cleavage activity, the Sml rz was chosen for further study and manipulation. In an effort to improve the efficiency of the Sm 1 rz self-cleavage activity, a series of modifications of the Sml rz structure were made and evaluated. As shown in FIG. 1d, specific modification at nucleotide 7 (C to U) in the conserved catalytic core (Hertel, et al., 1992, Nucleic Acids Res 20, 3252), and changes in distal stem III led to a significant increase in the extent of self-cleavage (the modified Sml rz was termed 'N73', up to 62-fold difference between functional and inactive rz). Transfer of the N73 rz from position A to E of the vector enhanced the activity to 225-fold (this rz was termed 'N79' and was used in the subsequent studies). Additional modifications of stem I near the catalytic core and near the restriction insertion site led to further increases in activity, resulting ultimately in an overall 1401-fold difference in expression levels between functional vs. inactive rz (FIG. 1e).

In addition to modifications that led to improved self-cleavage activity, several modifications, notably those involving the shortening of stem I (FIG. 1f), and alteration of nucleotides within the internal loop of stem I (FIG. 1g), dramatically reduced the level of self-cleavage. Interestingly, neither of those modifications affect conserved core sequences known to be required for rz cleavage in vitro (Ruffner, et al., 1990, Biochemistry 29, 10695-702). Under standard in vitro conditions of 10 mM $Mg^{++}$, measurement of the catalytic activity of the N79 rz and the N107 (U to G) rz, which carries a single base U to G change in the loop I and is inactive in mammalian cells (FIG. 1g), indicated that both rzs were equally functional in vitro ($K_{obs}$ values of $0.84^{-min}$ and, $1.06^{-min}$ respectively, see Supplementary Methods). Intriguingly, however, determination of the cleavage rate at 0.5 mM $Mg^{++}$ indicated that only the N79 enzyme possessed significant activity under low $Mg^{++}$ conditions (N79 rz $K_{obs}=0.84^{-min}$ vs. N107 (U to G) rz $K_{obs}=0.014^{-min}$). These results suggest that sequences within the unique loop structure of stem-I of the Sml rz may enable efficient self-cleavage in mammalian cells in part because they facilitate self-cleavage at physiological $Mg^{++}$ concentrations. Consistent with this idea, measurement of the $K_{obs}$ of another well-characterized hammerhead rz ("McSwiggen's hammerhead", Table 1) previously shown by others to function in mammalian cells, yet shown in our transfection assay to possess no appreciable activity, indicated that significant in vitro cleavage activity occurred only under high $Mg^{++}$ conditions ($0.32^{-min}$ at 10 mM $Mg^{++}$ vs. $0.015^{-min}$ at 0.5 mM $Mg^{++}$). To what extent the ability to function at low $Mg^{++}$ concentration per se contributes to the ability of a rz to function efficiently in mammalian cells remains unclear, however, since several rzs engineered by others to efficiently function in vitro under low $Mg^{++}$ conditions[13-14] were amongst the many rzs that were found to be non-functional in our transient transfection assay.

Applicants also found that the efficiency of *schistosoma* ribozymes was independent of the amount of plasmid DNA transfected in mammalian cells. A wide range of plasmid DNA concentration was tested in the transfection assay. It was found that the efficiency of the *schistosoma* ribozymes remained unchanged with increasing amounts of transfected DNA. This suggests that the function of *schistosoma* ribozymes is largely independent of the cellular resource and can be coupled to a strong promoter to produce high copy numbers of regulatable mRNA. Applicants tested four kinds of promoters (CMV promoter, EFI-alfa promoter, Ubiquitin C promoter, and Lenti viral promoter) and found that they all worked well with the *Schistosoma* ribozymes. Since the ribozyme mechanism should be independent of the promoter systems, Applicants believe that the *schistosoma* ribozymes should work with all different promoters. Applicants also tested four kinds of reporter genes (Lac-Z, GFP, dsRED, and Luciferase) and they all worked well with the *Schistosoma* ribozymes. Applicants believe that *schistosoma* ribozymes should work with other reporter genes. Applicants further found that *schistosoma* ribozymes worked not only in transiently transfected cells, but also in stably transfected cells. Several stable HEK-293 cell lines containing *schistosoma* ribozymes were generated. These cell lines were later used to screen libraries of small compounds that eventually led to the discovery of drugs for ribozyme inhibition and thus the regulation of gene expression (see below).

Figures 2A, 2B, 2C:
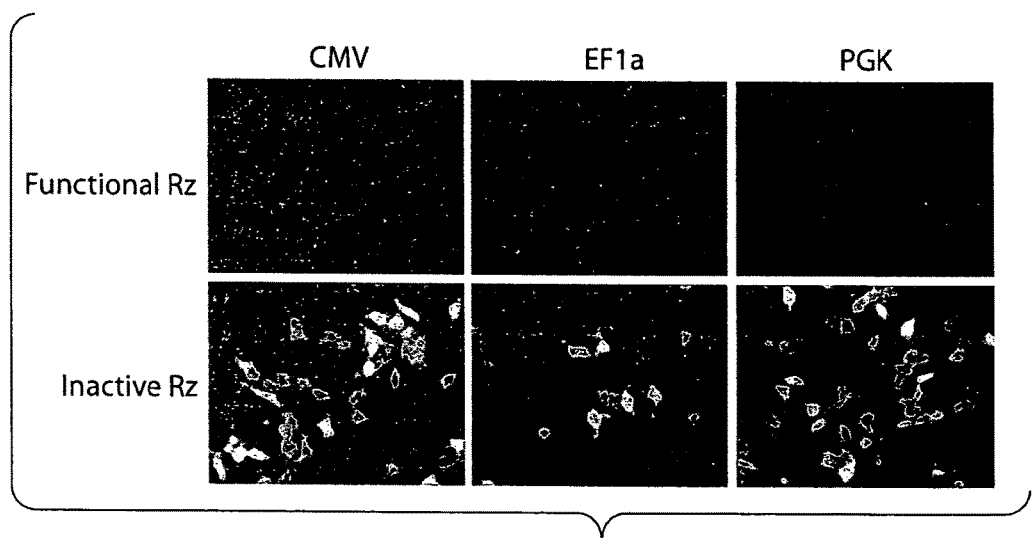
FIGS. 2a-2c show that efficient self-cleavage can occur in different cells, with different vectors, and with rz sequences positioned in different locations. (a) and (b) N79 functioned efficiently in a variety of cell types. Numbers are the measurements of β-gal expressed. (c) N79 functioned efficiently at some but not all positions within the vector. Numbers are 'fold decrease' in β-gal expression (functional vs. inactive rz). The ±signs indicate standard deviation from mean of at least four independent measurements.

For example, in addition to functioning in 293 cells within the context of the original CMV-based pMD vector tested, the N79 rz also dramatically reduced B-gal expression in a variety of other commonly used cell lines after transfection (FIG. 2a). In addition, the N79 rz was able to function efficiently when placed within other transcriptional units which made use of different promoters and a different reporter gene (eGFP) (FIG. 2b). As Applicants had observed in the primary screen of different rz motifs for activity in mammalian cells, N79 was able to function when placed in several, but not all locations of the pMD transcriptional unit, albeit at different efficiencies (FIG. 2c). Importantly, placement of two rz sequences in tandem, in some cases (e.g., E position) led to a dramatic suppression of reporter gene expression (FIG. 2c).

An essential requirement for the development of a gene regulation system based on modulation of self-cleavage activity is the availability of small inducer molecules capable of efficient inhibition of rz activity in mammalian cells. In an effort to identify such molecules, Applicants first surveyed a large number of common antibiotics that had been shown to inhibit rz cleavage in vitro (Table 1 above) (Hermann, et al., 1998, J Mol Biol 276, 903-12; Jenne, et al., 2001, Nat Biotechnol 19, 56-61; Murray, et al., 1996, Biochem J 317 (Pt 3), 855-60; Stage, et al., 1995, RNA 1, 95-101; Tor, et al., 1998, Chem Biol 5, R277-83; von Ahsen, et al., 1991, Nature 353, 368-70). In no case was significant inhibition of self-cleavage by these antibiotics observed in our transient transfection assay.

Applicants next surveyed the ability of different types of antisense oligonucleotides (Braasch, et al., 2002, Biochemistry 41, 4503-10) to inhibit rz cleavage (see FIG. 1e for targeted sequence, SEQ ID NO: 50). While transfection with PNAs, LNAs, and "grip" NAs had no measurable effects on self-cleavage activity, and phosphorothioate, 2'-O-methyl, and phosphorothioate 2'-O-methyl derived RNAs led to modest inhibition of self-cleavage (<10-fold induction), transfection of a morpholino oligonucleotide (Morcos, et al., 2001, Genesis 30, 94-102) led to a strong inhibition of rz self-cleavage, as revealed by a dramatic increase in reporter gene expression (FIG. 3a). While the 'fold' induction afforded by this method was somewhat variable from experiment to experiment (110-2000-fold in the case of double N79 construct) most likely due to the variability of efficiency of oligo delivery and toxicity associated with transfection of the oligo, the extent of induction of gene expression was nonetheless comparable to that achieved with other gene regulation systems, and clearly represents a range that would be useful for a variety of experimental and clinical settings. In some cases, the absolute levels of gene expression achieved after morpholino administration approached 50% of the theoretical maximum induction possible (i.e., the level of gene expression produced by the inactive rz), suggesting that rz cleavage can be very efficiently inhibited in mammalian cells.

Applicants generated stable cell lines carrying an integrated expression construct in which a luciferase reporter was placed under the control of two copies of the N79 rz, and made use of the cells in high-throughput screening studies to identify small molecule compounds capable of inhibiting rz self-cleavage. Of the compounds identified (Table 1 below), toyocamycin (Aszalos, et al., 1966, J Antibiot (Tokyo) 19, 285), a nucleoside analogue, was found to be one of the most potent inhibitors of rz function. As shown in FIG. 3b, administration of 1.5 µm toyocamycin to the same cells led to a dramatic increase in luciferase protein expression. A parallel analysis of luciferase mRNA expression demonstrated that in the absence of drug, little if any luciferase mRNA was produced in the nucleus or cytoplasm, while in drug-treated cells, the amount of luciferase mRNA was increased to a level comparable to that of cells carrying inactive rz (FIG. 3c). The lack of detectable mRNA in untreated cells suggests that cleaved mRNAs are rapidly degraded, presumably because the cleaved fragments lack conventional sequences at the ends of mRNAs.

TABLE 2

Compounds found to inhibit ribozyme activity in cells

| Compound name | $EC_{50}$ (µM) | $Fold_{max}$ | Class |
|---|---|---|---|
| Toyocamycin | 0.4 | 365 | ribo-nucleoside |
| 8-Azaadenosine | 4 | 45 | ribo-nucleoside |
| Sangivamycin | 1 | 38 | ribo-nucleoside |
| Tubercidin | 2.5 | 58 | ribo-nucleoside |
| Tubercidin-cyclic monophosphate | 34 | 35 | ribo-nucleoside |
| Tubercidin-monophosphate | 2 | 39 | ribo-nucleoside |
| Tubercidin-triphosphate | 2 | 35 | ribo-nucleoside |
| Nebularine | 10 | 8 | ribo-nucleoside |
| Tricyclic Nucleoside | 40 | 12 | ribo-nucleoside |
| 5-FluoroUridine | 5.9 | 120 | ribo-nucleoside |
| 5-BromoUridine | 267 | 16 | ribo-nucleoside |
| 5-FluoroUracil | 200 | 377 | pyrimidine |
| Syto-83 | 7 | 26 | RNA-binding dye |
| Homidium bromide | 2 | 8 | RNA-binding dye |
| Acridine orange | 7 | 4 | RNA-binding dye |

Figure 9A:
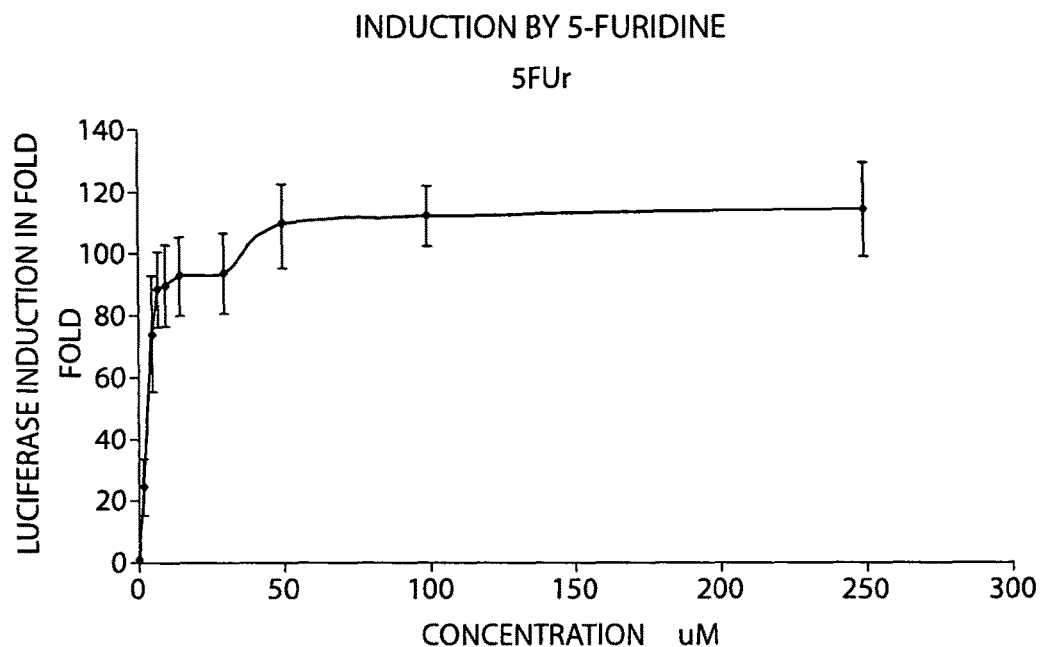
FIGS. 9A-9B show that 5'-FUridine (A) and 5'-FUracil (B) induced gene expression via inhibition of rz self-cleavage in a dose-dependent manner.
Figure 9B:
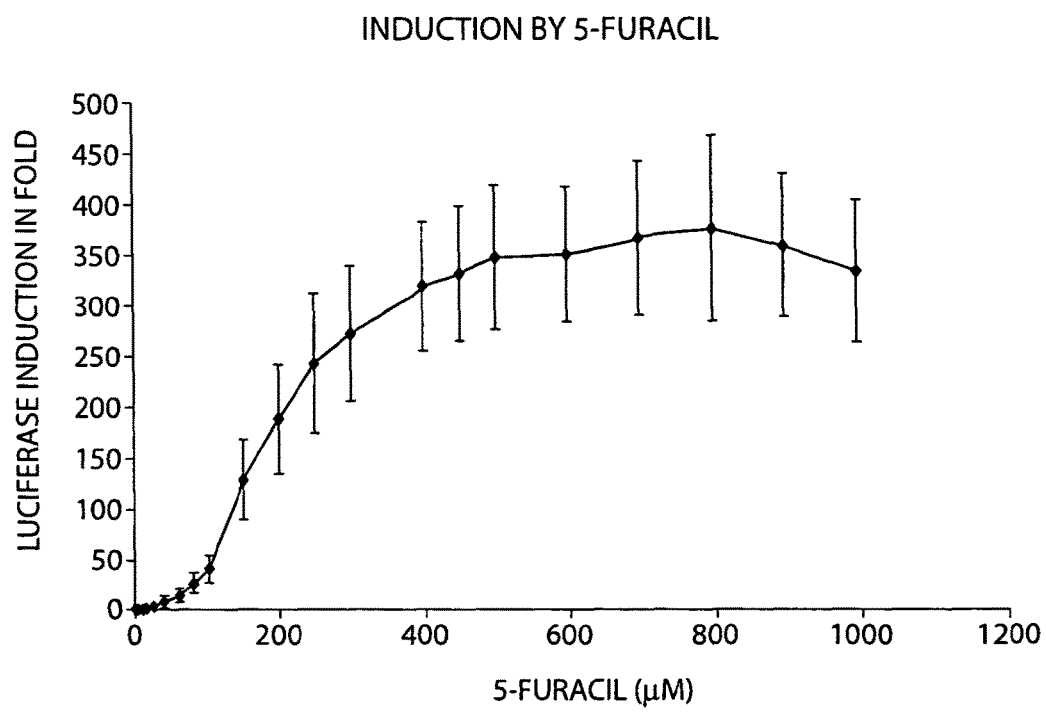
Figure 10A:
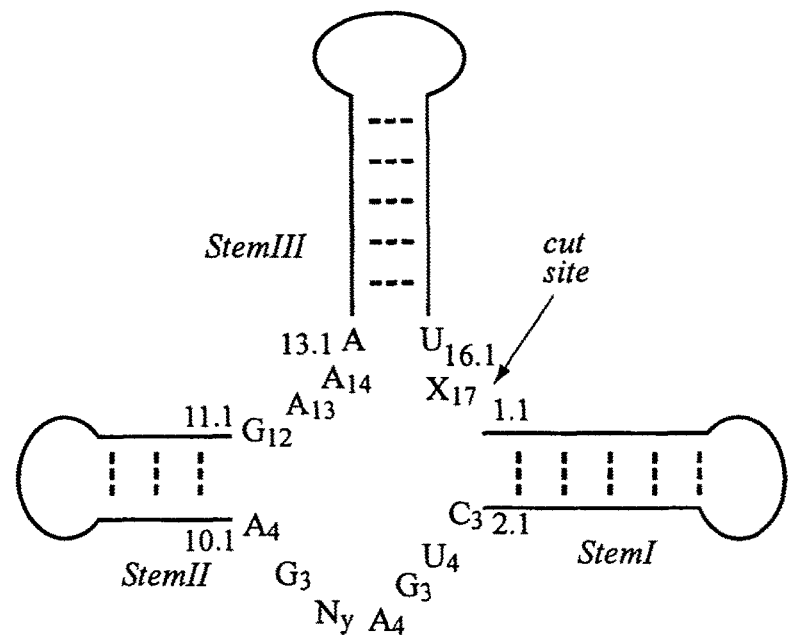
FIGS. 10A-10D shows structures of four small ribozymes: (a) the hammerhead; (b) hairpin; (c) hepatitis delta virus; and (d) *Neurospora* VS ribozymes (SEQ ID NO: 51). Hammerhead ribozymes (a) are composed of three stem helices designated I, II, and III. The core region comprises unpaired nucleotides. Loop structures can be present branching off stems I, II, and III.
Figure 10B:
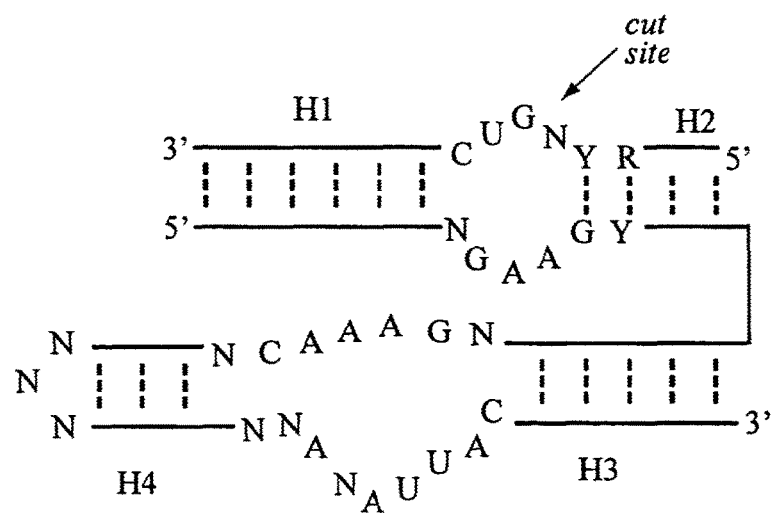
Figure 10C:
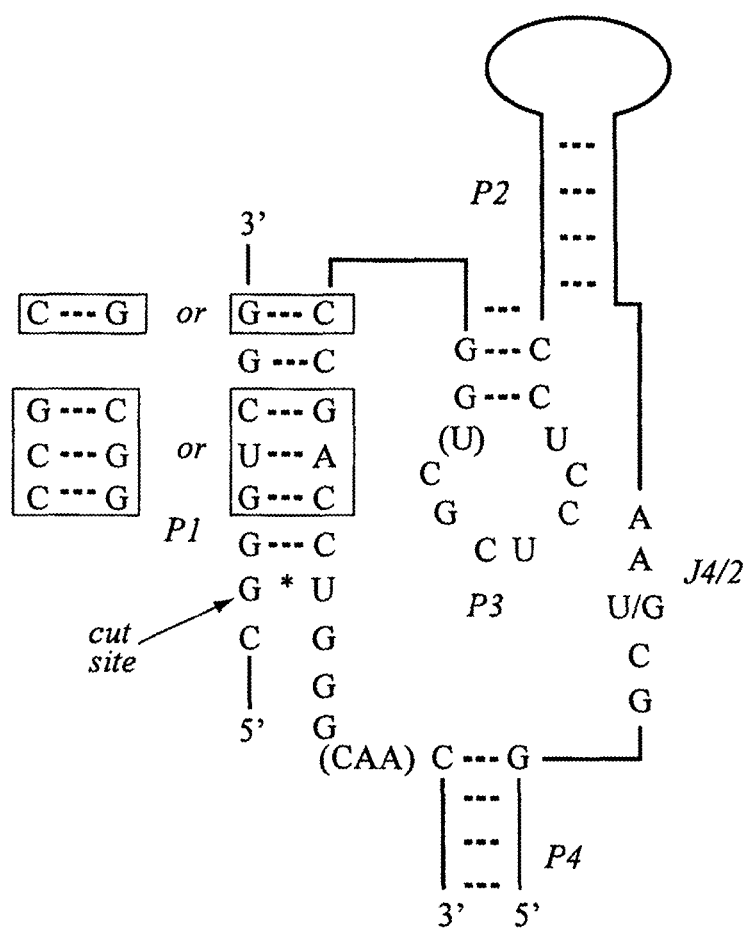
Figure 10D:
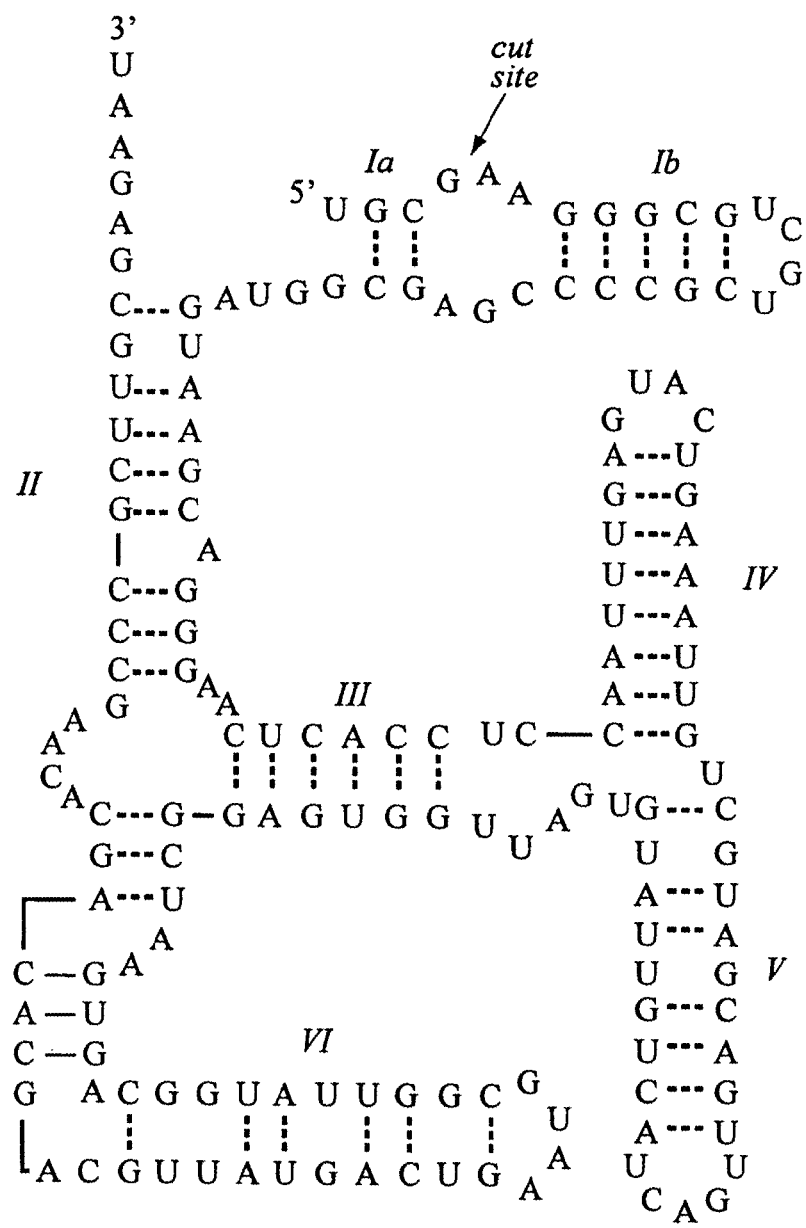
Figure 11:
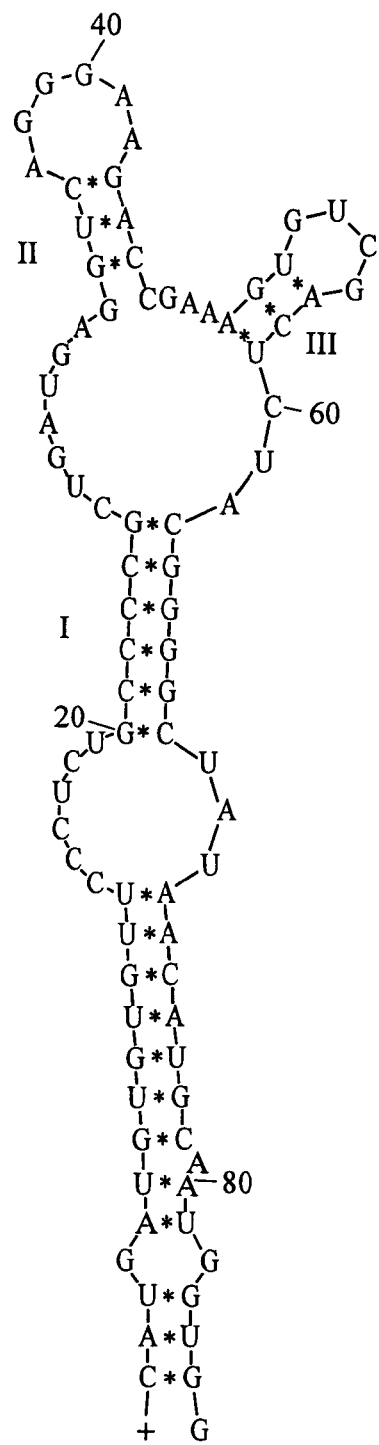
FIG. 11 shows the secondary structure and nucleotide sequence of Cricket ribozyme (SEQ ID NO: 52).
Figure 12:
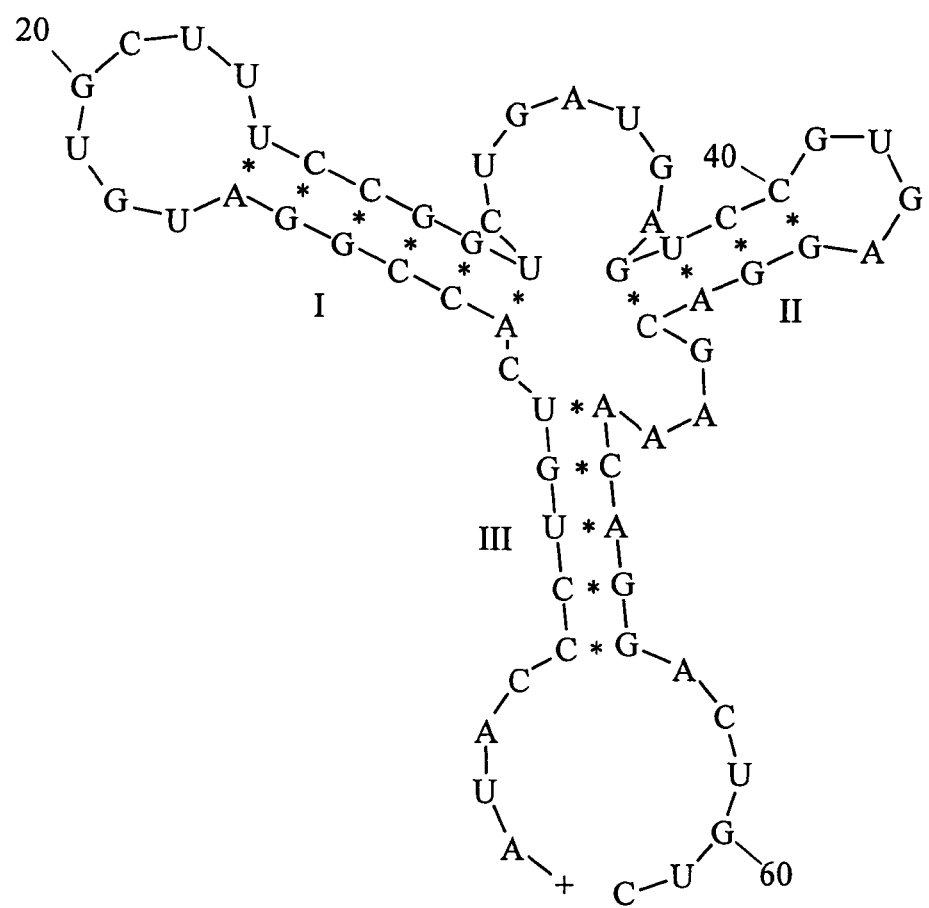
FIG. 12 shows the secondary structure and nucleotide sequence of TRSV ribozyme (SEQ ID NO: 53).
Figure 13:
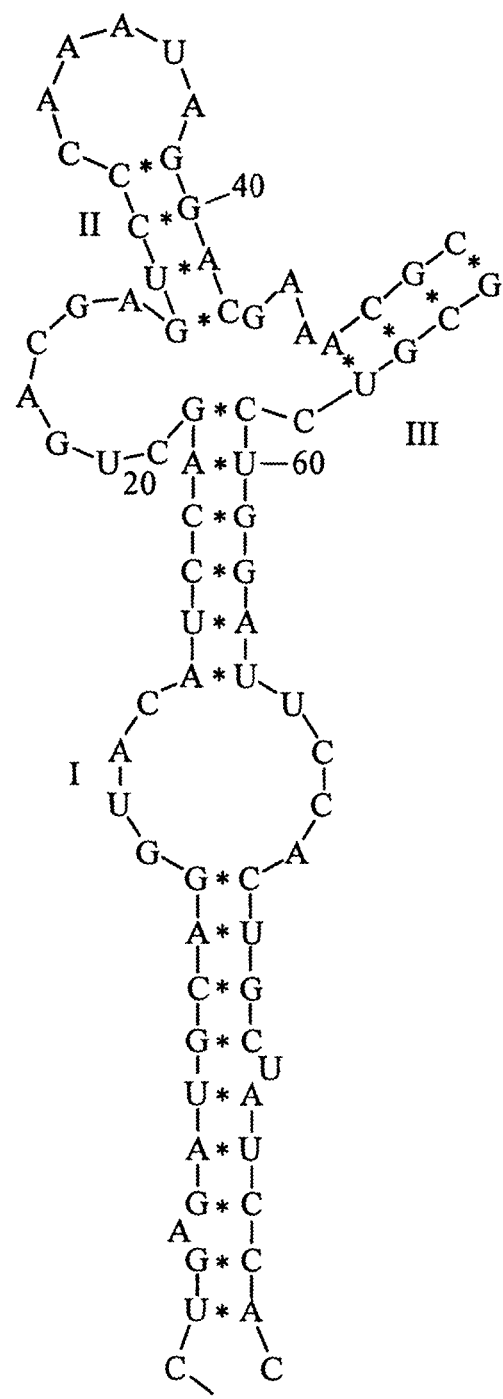
FIG. 13 shows the secondary structure and nucleotide sequence of the naturally-occurring (wildtype) schistosome ribozyme and the location of the initial modifications (SEQ ID NO: 2). Stems I, II, and III are noted.

In addition to toyocamycin, 5'-FU compounds (such as 5'-FluoroUridine and 5'-FluoroUracil) are two other potent inhibitors of rz function (Table 2). These two 5'-FU compounds are also nucleoside analogues. FIGS. 9A-9B show that 5'-FUridine (A) and 5'-FUracil (B) induced gene expression via inhibition of rz self-cleavage in a dose-dependent manner. As shown in FIGS. 9A and 9B, administration of the two 5'-FU compounds to the cells led to a dramatic increase in luciferase protein expression in a dose-dependent manner.

In contrast to toyocamycin, adenosine, a related compound, possessed no ability to inhibit rz self-cleavage. While the above assays indicate that self-cleavage is highly efficient in the stable cell line, sensitive measurement of luciferase activity by photon emission indicates that there is, nevertheless, an extremely low but detectable amount of luciferase expression above the background emission level of control cells that carry no luciferase gene (see legend to FIG. 3).

Figure 4:
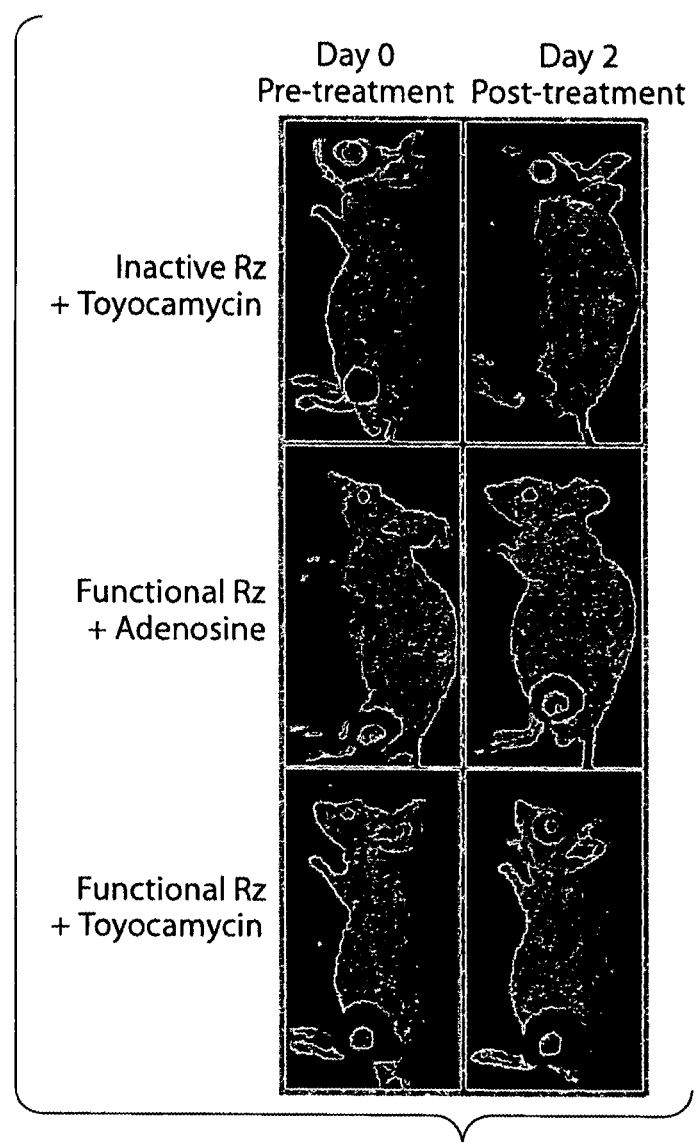
FIG. 4 show effective control of gene expression in vivo using rz-based gene regulation system. Upper panel shows the animal in which retina was injected with AAV carrying double inactive N79 and treated with toyocamycin. Middle panel shows the animal in which retina was injected with AAV carrying double functional N79 and treated with adenosine. Lower panel shows the same as middle panel but treated with toyocamycin. A strong induction in luciferase expression at day 2 was observed in lower panel. Animals were also injected in the hamstring muscles of the hind limb with AAV carrying double inactive N79 as internal control. AAV injection was done 3 weeks prior to the first imaging day (day 0). Drug-releasing pellets were implanted subcutaneously in the dorsal neck immediately after the first imaging, and released the drug over 7 days. The toyocamycin pellet contains 10 μg of drug; adenosine pellet 50 μg.
Figure 6:
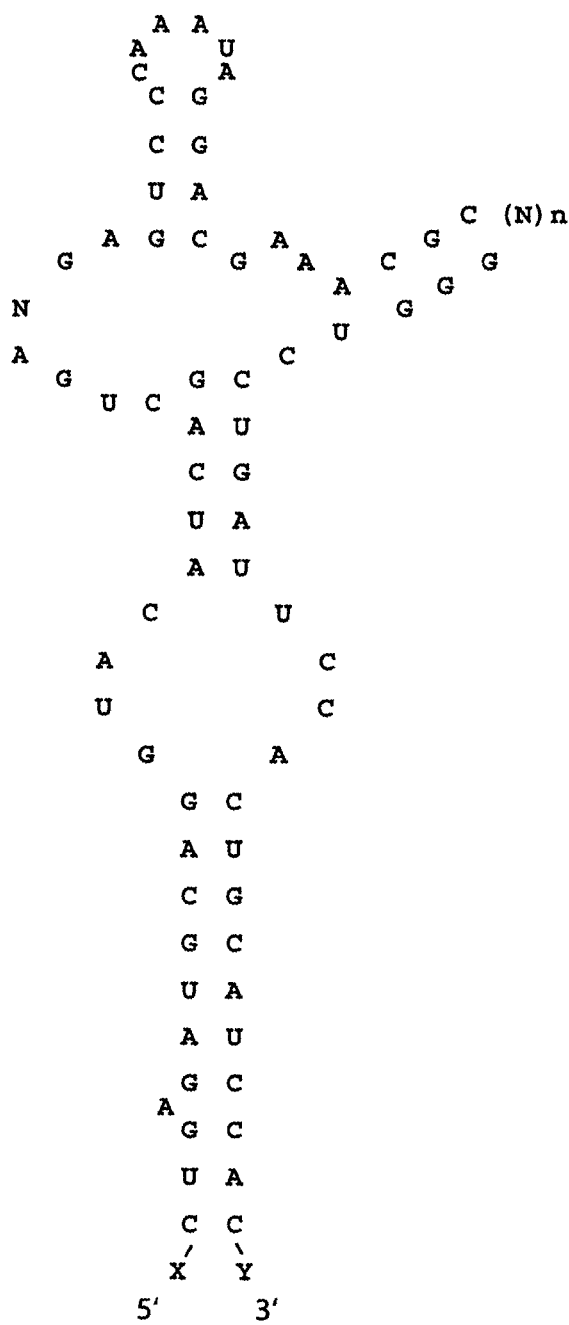
FIG. 6 is a diagram illustrating the partial nucleotide sequence of a self-cleaving schistosome RNA motif and sites for loop Ill and core modification; SEQ ID NO: 47.
Figure 7:
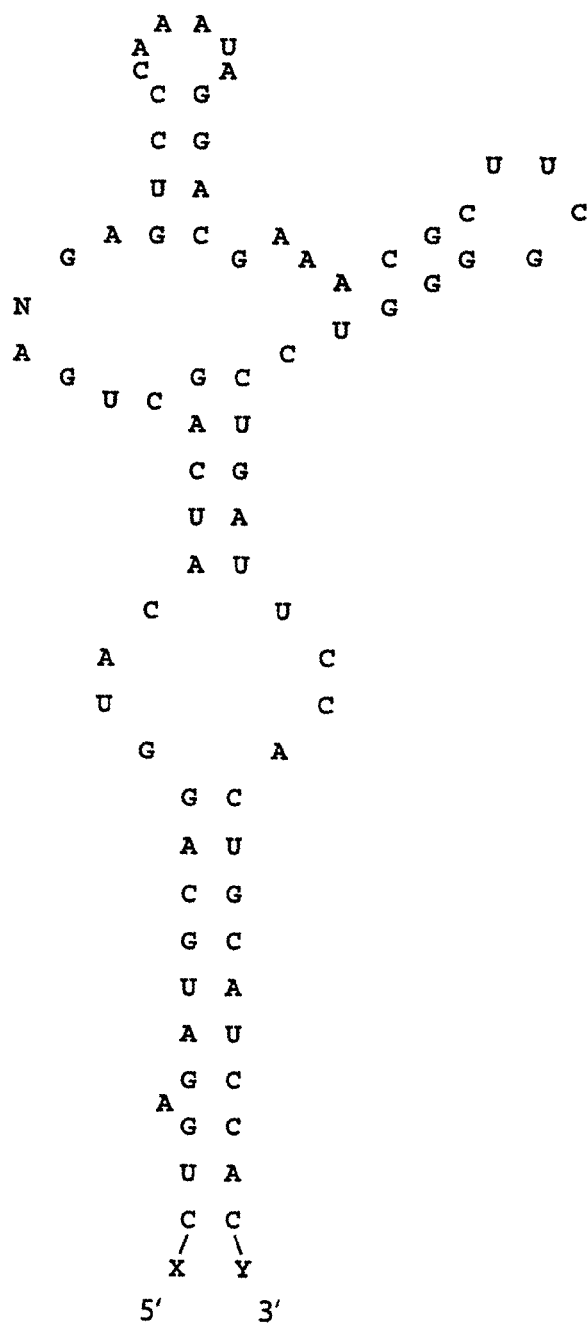
FIG. 7 is a diagram illustrating the partial nucleotide sequence of a self-cleaving schistosome RNA motif with a four-nucleotide loop III and a site for core modification; SEQ ID NO: 48.

Having documented the ability of the rz-based regulation system to function in mammalian cell culture, a final important issue to be addressed was whether the intracellular machinery and 'environment' necessary for self-cleavage was operable in primary cells in vivo. To address this issue, Applicants generated recombinant adeno-associated virus (AAV) genomes carrying transcription units derived from pMD rz-luciferase vectors possessing two copies of functional or inactive N79 rz at the E position and prepared high titer virus possessing the host range of AAV serotype 5. The two viruses were then used to inject nude mice subretinally as described under "Methods." To provide a means of normalization for differences in the capacity to measure luciferase activity on different days (such as variations due to the delivery of the luciferin substrate), all animals were also injected in the hamstring muscles of the hind limb with AAV viruses carrying the inactive N79 rzs. After 21 days, the injected animals were imaged for luciferase gene expression using the Xenogen IVIS imager, which provides a quantitative measure of luciferase expression based on single-photon detection (Contag, et al., 1998, Nat Med 4, 245-7). Immediately after imaging, cohorts of mice injected with virus carrying the functional rz sequences were implanted under the dorsal skin with seven day 'time-release' pellets of either toyocamycin or adenosine (Innovative Research of America, Inc), while another cohort of mice injected with virus carrying the inactive rz sequences were implanted with toyocamycin pellets. Two days later, all animals were then imaged for luciferase expression. Representative images of mice in each treatment group, taken before and after drug treatment, are shown in FIG. 4. The images demonstrate that, as expected, mice injected with virus carrying inactive rzs showed robust luciferase expression in the retina, and the expression was independent of the administration of toyocamycin (FIG. 4, upper panel). Mice injected with virus carrying two functional rzs and implanted with adenosine pellets showed little if any gene expression before or after adenosine treatment (FIG. 4, middle panel), consistent with the inability of adenosine to inhibit rz self-cleavage. Impontly, mice injected with virus carrying the functional rzs showed readily detectable expression only after toyocamycin treatment (FIG. 4, lower panel). Quantification of the photon output indicated gene expression was 'induced' 39, 185, and 191-fold in the three mice infected with virus carrying the functional rzs and treated with toyocamycin. In the last case (animal showing 191-fold induction) the induced gene expression reached a level within 40% of the gene expression of virus carrying inactive rzs. These results indicate that significant rz-mediated gene regulation can be accomplished in the in vivo setting. While the retina may be particularly accessible to 'inducer' due to its extensive vascularization, Applicants have shown in preliminary experiments that gene regulation can be accomplished at a number of other anatomical sites in vivo (e.g., muscle and ear).

Overall, the studies reported here provide an important 'proof-of-principle' for gene regulation strategies based on the modulation of RNA processing. Specifically, the fact that efficient rz 'self-cleavage' can be made to occur in a variety of different mammalian cell lines, and in primary cells in vivo suggests that mammalian cells may in general be 'permissive' for efficient ribozyme self-cleavage and therefore that rz-based regulation systems may be generally applicable to the manipulation of gene expression in cells and animals. In addition to implications for the development of gene regulation strategies, the studies also provide a compelling rationale for determining whether 'naturally occurring' RNA-only mechanisms for gene regulation exist in mammalian cells exist.

The most commonly used systems for controlling gene expression, which rely on the regulation of transcription (Gossen, et al., 1992, Proc Natl Acad Sci USA 89, 5547-51; Rivera, et al., 1996, Nat Med 2, 1028-32; Suhr, et al., 1998, Proc Natl Acad Sci USA 95, 7999-8004; Wang, et al., 1994, Proc Natl Acad Sci USA 91, 8180-4) have proved to be extremely powerful experimental tools. However, despite their utility, such systems possess at least some practical and theoretical limitations due to their reliance on chimeric transcriptional transactivators and specialized promoter elements. These limitations include the need to co-introduce expression constructs for both the transactivator and the transgene to be regulated, the potential toxicities due to expression of a chimeric transactivator, difficulties in application of such systems to the regulation of endogenous cellular genes due to the requirement of a specialized promoter, and the limited number of small inducer molecules available for experimental and therapeutic applications. In contrast to systems based on the regulation of transcription, the rz-based system Applicants have described does not require the expression of any protein transactivator products and is not dependent upon the use of any specialized promoter elements, and therefore, in theory, represents a 'portable' regulation system that could be 'embedded' into any endogenous gene or engineered vector transcription unit. Although the two inhibitors of rz self-cleavage Applicants have described may not be ideal for many experimental applications, it is likely that additional inducers with more desirable pharmacokinetic properties and toxicity profiles can be identified via high-throughput screening, further evaluation of specific antisense oligonucleotides and methods for their in vivo delivery to cells, or through the application of several emerging technologies. In this latter regard, recent studies have shown that it is possible to generate rzs whose in vitro self-cleavage activity is controlled by a specific ligand, either by the 'judicious' linkage of RNA aptamer sequences to specific regions of hammerhead rz (Breaker, et al., 2002, Curr Opin Biotechnol 13, 31-9), or through the use of in vitro evolution technologies {Wilson, et a., 1999, Annu Rev Biochem 68, 611-47). Application of these technologies to the strategy for controlling gene expression described here should make it possible in the future to 'tailor' specific rz-based gene regulation systems to any small molecule ligand. Such an approach would provide a general methodology for developing gene regulation systems which rely on ligands with desirable and/or specific pharmacokinetic properties. In addition, the combined technologies should provide the means to independently and simultaneously control the expression of multiple gene products, and to express gene products in response to the concentration of any intracellular molecule or combinations of molecules. Such a form of 'biological sensing' could have broad experimental and therapeutic applications.

Methods:

1) Transfection Protocol:

1.5 µl Fugene-6 (Roche, Basel, Switzerland) was diluted in 100 µl OPTIMEM (Gibco, Carlsbad, Calif.) and incubated for 5 minutes at room temperature. This solution was added dropwise to 0.45 µg plasmid DNA and incubated for 15 minutes. The plasmid DNA contains either a wildtype or a mutant ribozyme and a Lacz reporter gene. The DNA mixture was then added dropwise to $3 \times 10^5$ HEK 293 cells (plated the previous day in a 35 mm dish). Cells were harvested for β-galactosidase assay 24 hours following transfection.

2) Transient Reporter Expression Assay:

Plasmids carrying different ribozymes were transfected into HEK293T cells and lysed 24 h later. The cell extracts were incubated with ONPG, and the amount of B-galactosidase in cell extracts was measured by quantifying the processed ONPG using a luminometer.

3) Assays for Ribozyme Activity:

Cleaving activity was determined by comparing the level of –galactosidase measured in the test sample to a control comprising a point mutation (A-+G) at position 14 which attenuates ribozyme activity. Briefly, transfected HEK293 cells were lysed with a lysis solution and the extracts of cells were separated from cell debris. The extracts were then incubated with ONPG, a chromogenic substrate of β-galactosidase. Cleavage of ONPG by β-galactosidase resulted in a yellow color. The intensity of yellow light emission was measured with a luminometer (Miller J., *Experiments in Molecular Genetics*, Cold Spring Harbor Laboratory, Cold Spring Harbor, N.Y. (1972)).

Most of Applicants' assays on ribozyme activity were performed at protein level. The active ribozymes (the wild-type) produced little or no proteins while the inactive ribozymes (the mutant) enabled high protein production. Applicants also performed Northern analyses to compare the mRNA level. It was found that the cell line containing the active ribozymes had no detectable level of mRNA in both the nucleus and cytoplasm, as compared to the high level of mRNA found in the cells with inactive ribozymes. This is consistent with the idea that the ribozymes acted at the transcriptional level.

4) Catalytic Rate Measurement:

Ribozymes were generated by in vitro transcription in the presence of 50 uM blocking antisense oligos. Full length ribozymes were purified and the cleavage rate determined in 50 mM Tris-HCl, pH7.5 at 23° C. $K_{obs}$ was calculated according to the equation $F_1=F_0+F_\infty(1-e^{kt})$.

5) Non-Invasive Bioluminescent Imaging:

Prior to imaging, the anesthetized mice were injected with 150 μl of luciferin (30 mg/ml) and the pupils were moistened and dilated with 1% tropicamide. A series of bioluminescent images were taken for up to 30 minutes using the Xenogen IVIS imager. Photon output was quantified at the plateau of the time course using the LivingImage software. Induction in fold was calculated based on the photon output in the retina before and after drug treatment, and was normalized to the photon output from the leg muscles. Adenosine was purchased from Innovative Research of America.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A nucleic acid encoding a schistosome ribozyme mutant comprising:

(i) a sequence of a wildtype *Schistosoma mansoni* ribozyme of SEQ ID NO: 2; and (ii) an additional loop of 5'-UUCG-3', 5'-CUUCGG-3', or 5'-GCUUCGGU-3' inserted between nucleotide positions 49 and 50 in SEQ ID NO: 2; and optionally (iii) one or both of:

a substitution of C at nucleotide position 26 of SEQ ID NO: 2 with an U, A, or G; and one of three different sets of four substitutions in SEQ ID NO: 2:

a substitution of A at nucleotide position 20 with C, substitution of G at nucleotide position 21 with A, substitution of C at nucleotide position 55 with U, and a substitution of U at nucleotide position 56 with G;

a substitution of A at nucleotide position 20 with C, substitution of G at nucleotide position 21 with U, substitution of C at nucleotide position 55 with A, and a substitution of U at nucleotide position 56 with G; or a substitution of A at nucleotide position 20 with G, substitution of G at nucleotide position 21 with U, substitution of C at nucleotide position 55 with A, and a substitution of U at nucleotide position 56 with C.

2. The nucleic acid of claim 1, wherein the schistosome ribozyme mutant comprises a nucleotide sequence selected from the group consisting of: SEQ ID NO: 17, SEQ ID NO: 19, SEQ ID NO: 35, SEQ ID NO: 51, SEQ ID NO: 54, SEQ ID NO: 56, SEQ ID NO: 59, SEQ ID NO: 60, and SEQ ID NO: 61.

3. The nucleic acid of claim 2, wherein the schistosome ribozyme mutant comprises the sequence of SEQ ID NO: 17.

4. The nucleic acid of claim 2, wherein the schistosome ribozyme mutant comprises the sequence of SEQ ID NO: 19.

5. The nucleic acid of claim 2, wherein the schistosome ribozyme mutant comprises the sequence of SEQ ID NO: 51.

6. The nucleic acid of claim 2, wherein the schistosome ribozyme mutant comprises the sequence of SEQ ID NO: 54.

7. The nucleic acid of claim 2, wherein the schistosome ribozyme mutant comprises the sequence of SEQ ID NO: 56.

8. The nucleic acid of claim 2, wherein the schistosome ribozyme mutant comprises the sequence of SEQ ID NO: 59.

9. A host cell comprising the nucleic acid of claim 1.

10. The host cell of claim 9, wherein the host cell is a mammalian cell.

11. The host cell of claim 10, wherein the mammalian cell is a human cell.

12. A nucleic acid comprising:
(a) a promoter;
(b) a sequence encoding a nucleic acid product; and
(c) a sequence encoding a schistosome ribozyme mutant comprising:
   (i) a sequence of a wildtype *Schistosoma mansoni* ribozyme of SEQ ID NO: 2; and
   (ii) an additional loop of 5'-UUCG-3', 5'-CUUCGG-3', or 5'-GCUUCGGU-3' inserted between nucleotide positions 49 and 50 in SEQ ID NO: 2; and
   optionally (iii) one or both of:
      a substitution of C at nucleotide position 26 of SEQ ID NO: 2 with an U, A, or G; and
      one of three different sets of four substitutions in SEQ ID NO: 2:
         a substitution of A at nucleotide position 20 with C, substitution of G at nucleotide position 21 with A, substitution of C at nucleotide position 55 with U, and a substitution of U at nucleotide position 56 with G;
         a substitution of A at nucleotide position 20 with C, substitution of G at nucleotide position 21 with U, substitution of C at nucleotide position 55 with A, and a substitution of U at nucleotide position 56 with G; or
         a substitution of A at nucleotide position 20 with G, substitution of G at nucleotide position 21 with U, substitution of C at nucleotide position 55 with A, and a substitution of U at nucleotide position 56 with C;
wherein:
the sequence of (b) and the sequence of (c) are operably linked to the promoter;
transcription of the sequence of (b) and the sequence of (c) produces a RNA molecule comprising the schistosome ribozyme mutant and a mRNA encoding the nucleic acid product; and
the schistosome ribozyme mutant is capable of cleaving the RNA molecule intramolecularly.

13. The nucleic acid of claim 12, wherein the schistosome ribozyme mutant comprises a nucleotide sequence selected from the group consisting of: SEQ ID NO: 17, SEQ ID NO: 19, SEQ ID NO: 35, SEQ ID NO: 51, SEQ ID NO: 54, SEQ ID NO: 56, SEQ ID NO: 59, SEQ ID NO: 60, and SEQ ID NO: 61.

14. The nucleic acid of claim 13, wherein the schistosome ribozyme mutant comprises the sequence of SEQ ID NO: 17.

15. The nucleic acid of claim 13, wherein the schistosome ribozyme mutant comprises the sequence of SEQ ID NO: 19.

16. The nucleic acid of claim 13, wherein the schistosome ribozyme mutant comprises the sequence of SEQ ID NO: 51.

17. The nucleic acid of claim 13, wherein the schistosome ribozyme mutant comprises the sequence of SEQ ID NO: 54.

18. The nucleic acid of claim 13, wherein the schistosome ribozyme mutant comprises the sequence of SEQ ID NO: 56.

19. The nucleic acid of claim 13, wherein the schistosome ribozyme mutant comprises the sequence of SEQ ID NO: 59.

20. The nucleic acid of claim 12, wherein the nucleic acid is present in the genome of a cell.

21. The nucleic acid of claim 12, wherein the nucleic acid is present in a vector.

22. The nucleic acid of claim 21, wherein the vector is a viral vector.

23. A host cell comprising the nucleic acid of claim 12.

24. The host cell of claim 23, wherein the cell is a mammalian cell.

25. The host cell of claim 24, wherein the mammalian cell is a human cell.

26. The host cell of claim 23, wherein the cell further comprises an inhibitor of the schistosome ribozyme mutant.

27. The host cell of claim 26, wherein the inhibitor of the schistosome ribozyme mutant is an antibiotic.

28. The host cell of claim 27, wherein the antibiotic is toyocamycin.

29. A method of inducing expression of a nucleic acid product in a host cell comprising contacting the host cell of claim 23 with an agent that inhibits cleavage of the schistosome ribozyme mutant, thereby inducing the expressing of the nucleic acid product in the host cell.

30. The method of claim 29, wherein the agent that inhibits cleavage of the schistosome ribozyme mutant is an antibiotic.

31. The method of claim 30, wherein the antibiotic is toyocamycin.

32. A method of inducing expression of a nucleic acid product in an individual comprising the steps of:
(a) obtaining cells from the individual under conditions appropriate for cell growth and cell division;
(b) introducing into the cells obtained in step (a) the nucleic acid of claim 12;
(c) returning the cells produced in step (b) to the individual; and
(d) administering to the individual an agent that inhibits cleavage of the schistosome ribozyme mutant, thereby inducing expression of the nucleic acid product in the individual.

33. The method of claim 32, wherein the agent that inhibits cleavage of the schistosome ribozyme mutant is an antibiotic.

34. The method of claim 33, wherein the antibiotic is toyocamycin.

* * * * *